(12) United States Patent
Momose et al.

(10) Patent No.: US 7,241,785 B2
(45) Date of Patent: Jul. 10, 2007

(54) FIVE-MEMBERED HETEROCYCLIC ALKANOIC ACID DERIVATIVE

(75) Inventors: Yu Momose, Takarazuka (JP); Tsuyoshi Maekawa, Nara (JP); Hiroshi Imoto, Kusatsu (JP); Hiroyuki Odaka, Kobe (JP); Hiroyuki Kimura, Sakai (JP)

(73) Assignee: Takeda Pharmaceutical Company Limited (JP)

(*) Notice: Subject to any disclaimer, the term of this patent is extended or adjusted under 35 U.S.C. 154(b) by 223 days.

(21) Appl. No.: 10/472,159

(22) PCT Filed: Mar. 22, 2002

(86) PCT No.: PCT/JP02/02741

§ 371 (c)(1),
(2), (4) Date: Sep. 22, 2003

(87) PCT Pub. No.: WO02/076959

PCT Pub. Date: Oct. 3, 2002

(65) Prior Publication Data

US 2004/0063775 A1    Apr. 1, 2004

(30) Foreign Application Priority Data

Mar. 23, 2001  (JP) ............................ 2001-085572

(51) Int. Cl.
C07D 413/10 (2006.01)
C07D 413/12 (2006.01)
A61K 31/422 (2006.01)

(52) U.S. Cl. ...................................... 514/374; 548/235
(58) Field of Classification Search ................ 548/235; 514/374

See application file for complete search history.

(56) References Cited

U.S. PATENT DOCUMENTS 6,967,212 B2 * 11/2005 Cheng et al. ................ 514/365

FOREIGN PATENT DOCUMENTS

| CA | 2031974 | 6/1991 |
| EP | 0612743 | 8/1994 |
| EP | 0629624 | 12/1994 |
| EP | 0710659 | 5/1996 |
| EP | 1067109 | 1/2001 |
| EP | 1 357 115 A1 | 10/2003 |
| WO | WO 92/20350 | 11/1992 |
| WO | WO 96/13264 | 5/1996 |
| WO | WO 99/58510 | 11/1999 |
| WO | WO 00/01679 | 1/2000 |
| WO | WO 00/08002 | 2/2000 |
| WO | WO 00/64876 | 11/2000 |
| WO | WO 01/17994 | 3/2001 |
| WO | WO 01/21602 | 3/2001 |
| WO | WO 01/38325 | 5/2001 |
| WO | WO 02/053547 | 7/2002 |

OTHER PUBLICATIONS

Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*

* cited by examiner

*Primary Examiner*—Laura L. Stockton
(74) *Attorney, Agent, or Firm*—Finnegan, Henderson, Farabow, Garrett & Dunner, LLP

(57) ABSTRACT

The present invention relates to a compound represented by the formula

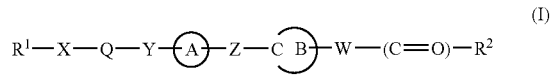

(I)

wherein $R^1$ is an optionally substituted 5-membered heterocyclic group; X is a bond etc.; Q is a divalent hydrocarbon group having 1 to 20 carbon atoms; Y is a bond etc.; ring A is an aromatic ring optionally further having 1 to 3 substituents; Z is —$(CH_2)_n$—$Z^1$— (n is an integer of 0 to 8 and $Z^1$ is a bond etc.) and the like; ring B is a 5-membered heterocycle optionally further having 1 to 3 substituents; W is a divalent saturated hydrocarbon group having 1 to 20 carbon atoms; $R^2$ is —OH etc., or a salt thereof. A pharmaceutical composition containing this compound is useful as a prophylactic or therapeutic agent of diseases such as diabetes mellitus and the like.

12 Claims, No Drawings

SEQUENCE LISTING

```
<160> NUMBER OF SEQ ID NOS: 10

<210> SEQ ID NO 1
<211> LENGTH: 34
<212> TYPE: DNA
<213> ORGANISM: Artificial Sequence
<220> FEATURE:
<223> OTHER INFORMATION: primer

<400> SEQUENCE: 1
```
aacggtacct cagccatgga gcagcctcag gagg                                    34

<210> SEQ ID NO 2
<211> LENGTH: 34
<212> TYPE: DNA
<213> ORGANISM: Artificial Sequence
<220> FEATURE:
<223> OTHER INFORMATION: primer

<400> SEQUENCE: 2
taagtcgacc cgttagtaca tgtccttgta gatc                                    34

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
ttagaattcg acatggacac caaacatttc ctg                                     33

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
cccctcgagc taagtcattt ggtgcggcgc ctc                                     33

<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5
tcgacagggg accaggacaa aggtcacgtt cgggag                                  36

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
tcgactcccg aacgtgacct ttgtcctggt cccctg                                  36

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
cccagatctc cccagcgtct tgtcattg                                           28

<210> SEQ ID NO 8
<211> LENGTH: 28
<212> TYPE: DNA
<213> ORGANISM: Artificial Sequence

```
<220> FEATURE:
<223> OTHER INFORMATION: primer

<400> SEQUENCE: 8
tcaccatggt caagcttta agcgggtc                                    28

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
gtgggtaccg aaatgaccat ggttgacaca gag                             33

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
ggggtcgacc aggactctct gctagtacaa gtc                             33
```

FIVE-MEMBERED HETEROCYCLIC ALKANOIC ACID DERIVATIVE

This application is the National Phase filing of International Patent Application No. PCT/JP02/02741, filed Mar. 22, 2002.

TECHNICAL FIELD

The present invention relates to a novel 5-membered heterocyclic alkanoic acid derivative having a superior hypoglycemic action and a superior hypolipidemic action and useful as a prophylactic or therapeutic agent of diabetes mellitus, hyperlipidemia, impaired glucose tolerance and the like.

BACKGROUND ART

As alkanoic acid derivatives, the compounds described in the following references are known.

(1) WO 00/64876 describes, as a PPAR ligand-receptor binder, a compound represented by the formula:

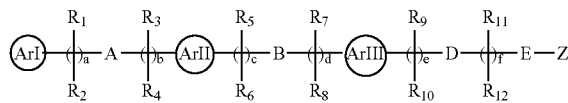

wherein

are each independently an aryl and the like; A is —O— and the like; B is —O— and the like; D is —O— and the like; E is a bond or an ethylene group; a, b, c and e are each 0–4; d is 0–5; f is 0–6; $R_1$, $R_3$, $R_5$, $R_7$, $R_9$ and $R_{11}$, are each independently a hydrogen and the like; $R_2$, $R_4$, $R_6$, $R_8$, $R_{10}$ and $R_{12}$ are each independently —(CH)$_q$—X; q is 0–3; X is hydrogen and the like; Z is $R_{21}O_2C$— and the like; $R_{21}$ is hydrogen and the like.

(2) WO 92/20350 describes, as a substance capable of mimicking the action of physiologically active natural polymer, a compound represented by the formula: Mi—(Mn)n—Mt wherein n is the number of 2 to about 50; Mi, Mn and Mt are

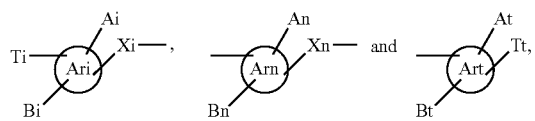

respectively;
wherein

are each independently an aromatic carbocycle or an aromatic heterocycle; Ai, Bi, An, Bn, At, Bt, Ti and Tt are each independently hydrogen or a substituent; and Xi and Xn are each independently a bond and the like.

(3) JP-A-4-217668 describes, as an antibacterial agent for agriculture and horticulture and an intermediate therefor, compounds respectively represented by the formula:

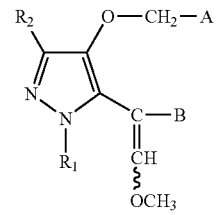

and the formula:

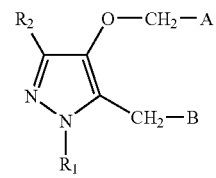

wherein $R_1$ and $R_2$ are each independently a hydrogen atom or a $C_1$–$C_5$ alkyl group, A is

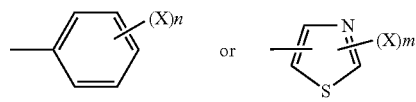

wherein X is a $C_1$–$C_{10}$ alkyl group optionally having one or more substituents selected from a $C_1$–$C_5$ alkoxy group, a halogen atom, a nitro group, a cyano group and a trifluoromethyl group and the like and B is a methoxycarbonyl group or a cyano group.

Peroxisome proliferator-activated receptor gamma (PPARγ), a member of the intranuclear hormone receptor superfamily, which is typically exemplified by steroid hormone receptors and thyroid hormone receptors, plays an important role as a master regulator in the differentiation of adipocytes with its expression induced in the very early stage of adipocyte differentiation. PPARγ forms a dimer with the retinoid X receptor (RXR) by binding to a ligand, and binds to a responsive site of the target gene in the nucleus to directly control (activate) transcription efficiency. In recent years, the possibility that 15-deoxy-$\Delta^{12,14}$ prostaglandin $J_2$, which is a metabolite of prostaglandin $D_2$, serves as an endogenous ligand for PPARγ, has been suggested, and it has been shown that a class of insulin resistance enhancers, typically exemplified by thiazolidinedione derivatives, possess ligand activity for PPARγ, and that its potency is proportional to its hypoglycemic action or adipocyte differentiation-promoting action [*Cell*, vol. 83, p. 803 (1995): *The Journal of Biological Chemistry*, vol. 270, p. 12953 (1995); *Journal of Medicinal Chemistry*, vol. 39, p. 655 (1996)]. Furthermore, in recent years, it has been shown that 1) PPARγ is expressed in cultured cells of human liposarcoma origin, whose proliferation is ceased by the addition of a PPARγ ligand [*Proceedings of the National Academy of Sciences of the United States of America*, vol. 94, p. 237 (1997)], 2) nonsteroidal anti-inflammatory drugs, typically exemplified by indomethacin and fenoprofen, have PPARγ ligand activity [*The Journal of Biological Chemistry*, vol. 272, p. 3406 (1997)], 3) PPARγ is expressed at high levels in activated macrophages, with the transcription of a gene involved in inflammation inhibited by the addition of a ligand therefor [*Nature*, vol. 391, p. 79 (1998)], and 4) PPARγ ligands suppress the production of inflammatory cytokines (TNFα, IL-1β, IL-6) by monocytes [*Nature*, vol. 391, p. 82 (1998)].

DISCLOSURE OF THE INVENTION

The development of a novel compound useful as a prophylactic or therapeutic agent of diabetes mellitus, hyperlipidemia, impaired glucose tolerance and the like and having superior properties as a pharmaceutical agent, such as fewer side effects and the like has been demanded. Accordingly, the present invention relates to (1) a compound represented by the formula:

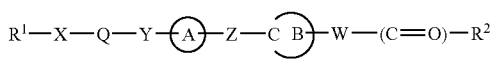

(I)

wherein
$R^1$ is an optionally substituted 5-membered heterocyclic group;
X is a bond, an oxygen atom, a sulfur atom, —CO—, —CS—, —$CR^3(OR^4)$— or —$NR^5$— ($R^3$ is a hydrogen atom or an optionally substituted hydrocarbon group, $R^4$ is a hydrogen atom or a hydroxy-protecting group and $R^5$ is a hydrogen atom, an optionally substituted hydrocarbon group or an amino-protecting group);
Q is a divalent hydrocarbon group having 1 to 20 carbon atoms;
Y is a bond, an oxygen atom, a sulfur atom, —SO—, —$SO_2$—, —$NR^6$—, —$CONR^6$— or —$NR^6CO$— ($R^6$ is a hydrogen atom or an optionally substituted hydrocarbon group);
ring A
is an aromatic ring optionally further having 1 to 3 substituents;
Z is —$(CH_2)_n$—$Z^1$— or —$Z^1$—$(CH_2)_n$— (n is an integer of 0 to 8, $Z^1$ is a bond, an oxygen atom, a sulfur atom, —SO—, —$SO_2$—, —$NR^7$—, —$CONR^7$— or —$NR^7CO$— ($R^7$ is a hydrogen atom or an optionally substituted hydrocarbon group));
ring B
is a 5-membered heterocycle optionally further having 1 to 3 substituents;
W is a divalent saturated hydrocarbon group having 1 to 20 carbon atoms; and
$R^2$ is —$OR^8$ ($R^8$ is a hydrogen atom or an optionally substituted hydrocarbon group) or —$NR^9R^{10}$ ($R^9$ and $R^{10}$ are the same or different and each is a hydrogen atom, an optionally substituted hydrocarbon group, an optionally substituted heterocyclic group, or an acyl group, or $R^9$ and $R^{10}$ may be linked to form an optionally substituted ring together with the adjacent nitrogen atom),
provided that, when ring B is a nitrogen-containing 5-membered heterocycle, then the nitrogen-containing 5-membered heterocycle does not have, on the ring-constituting N atom, a substituent represented by the formula:

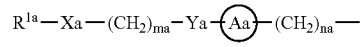

wherein
$R^{1a}$ is an optionally substituted hydrocarbon group or an optionally substituted heterocyclic group;
Xa is a bond, an oxygen atom, a sulfur atom, —CO—, —CS—, —$CR^{2a}(OR^{3a})$— or —$NR^{4a}$— ($R^{2a}$ and $R^{4a}$ are each a hydrogen atom or an optionally substituted hydrocarbon group and $R^{3a}$ is a hydrogen atom or a hydroxy-protecting group);
ma is an integer of 0 to 3;
Ya is an oxygen atom, a sulfur atom, —SO—, —$SO_2$—, —$NR^{5a}$—, $CONR^{5a}$— or —$NR^{5a}CO$— ($R^{5a}$ is a hydrogen atom or an optionally substituted hydrocarbon group);
ring Aa
is an aromatic ring optionally further having 1 to 3 substituents; and
na is an integer of 1 to 8,
or a salt thereof;
(2) the compound of the above-mentioned (1), wherein $R^2$ is —$OR^8$ ($R^8$ is a hydrogen atom or an optionally substituted hydrocarbon group) or —$NR^9R^{10}$ ($R^9$ and $R^{10}$ are the same or different and each is a hydrogen atom, an optionally substituted hydrocarbon group, an optionally substituted heterocyclic group or an acyl group, or $R^9$ and $R^{10}$ may be linked to form a ring together with the adjacent nitrogen atom);
(3) the compound of the above-mentioned (1), wherein the 5-membered heterocyclic group for $R^1$ is a 5-membered aromatic heterocyclic group;
(4) the compound of the above-mentioned (3), wherein the 5-membered aromatic heterocyclic group is oxazolyl, thiazolyl or triazolyl;
(5) the compound of the above-mentioned (1), wherein X is a bond or —$NR^5$— ($R^5$ is a hydrogen atom, an optionally substituted hydrocarbon group or an amino-protecting group);
(6) the compound of the above-mentioned (1), wherein Q is $C_{1-6}$ alkylene or $C_{2-6}$ alkenylene;
(7) the compound of the above-mentioned (1), wherein Y is an oxygen atom or —$NR^6$— ($R^6$ is a hydrogen atom or an optionally substituted hydrocarbon group);
(8) the compound of the above-mentioned (1), wherein the aromatic ring represented by the ring A is a benzene ring or a pyridine ring;
(9) the compound of the above-mentioned (1), wherein n is an integer of 0 to 3, $Z^1$ is a bond, an oxygen atom, a sulfur atom, —$NR^7$—, —$CONR^7$— or —$NR^7CO$— ($R^7$ is a hydrogen atom or an optionally substituted hydrocarbon group);
(10) the compound of the above-mentioned (1), wherein the ring B is a pyrazole ring, an oxazole ring or a thiazole ring, each optionally further having 1 to 3 substituents;
(11) the compound of the above-mentioned (1), wherein W is a divalent saturated hydrocarbon group having 1 to 6 carbon atoms;
(12) the compound of the above-mentioned (1), wherein $R^2$ is —$OR^8$ ($R^8$ is a hydrogen atom or an optionally substituted hydrocarbon group);

(13) the compound of the above-mentioned (1), wherein the substituent that the ring B optionally further has is a hydrocarbon group;
(14) the compound of the above-mentioned (1), which is
[1-methyl-3-[4-(5-methyl-2-phenyl-4-oxazolylmethoxy) benzyloxy]-1H-pyrazol-4-yl]acetic acid,
[1-methyl-3-[6-(5-methyl-2-phenyl-4-oxazolylmethoxy)-3-pyridylmethoxy]-1H-pyrazol-4-yl]acetic acid,
[1-methyl-3-[6-(2-phenyl-4-thiazolylmethoxy)-3-pyridylmethoxy]-1H-pyrazol-4-yl]acetic acid,
[1-benzyl-3-[6-(5-methyl-2-phenyl-4-oxazolylmethoxy)-3-pyridylmethoxy]-1H-pyrazol-4-yl]acetic acid,
[3-[4-(5-methyl-2-phenyl-4-oxazolylmethoxy)benzyloxy]-1-phenyl-1H-pyrazol-4-yl]acetic acid,
[3-[6-(5-methyl-2-phenyl-4-oxazolylmethoxy)-3-pyridylmethoxy]-1-phenyl-1H-pyrazol-4-yl]acetic acid,
3-[3-[3-methoxy-4-(5-methyl-2-phenyl-4-oxazolylmethoxy)benzyloxy]-1-phenyl-1H-pyrazol-5-yl]propionic acid,
3-[3-[4-(5-methyl-2-phenyl-4-oxazolylmethoxy)benzyloxy]-1-phenyl-1H-pyrazol-5-yl]propionic acid, or
3-[3-[3-(5-methyl-2-phenyl-4-oxazolylmethoxy)benzyloxy]-1-phenyl-1H-pyrazol-5-yl]propionic acid;
(15) a prodrug of the compound of the above-mentioned (1) or a salt thereof;
(16) a pharmaceutical composition comprising the compound of the above-mentioned (1) or a salt thereof or a prodrug thereof;
(17) the pharmaceutical composition of the above-mentioned (16), which is a prophylactic or therapeutic agent of diabetes mellitus;
(18) the pharmaceutical composition of the above-mentioned (16), which is a prophylactic or therapeutic agent of hyperlipidemia;
(19) the pharmaceutical composition of the above-mentioned (16), which is a prophylactic or therapeutic agent of impaired glucose tolerance;
(20) a retinoid-related receptor function regulating agent, which comprises the compound of the above-mentioned (1) or a salt thereof or a prodrug thereof;
(21) the agent of the above-mentioned (20), which is a peroxisome proliferator-activated receptor ligand;
(22) the agent of the above-mentioned (20), which is a retinoid X receptor ligand;
(23) an agent for improving insulin resistance, which comprises the compound of the above-mentioned (1) or a salt thereof or a prodrug thereof;
(24) a method for the prophylaxis or treatment of diabetes mellitus in a mammal, which comprises administering the compound of the above-mentioned (1) or a salt thereof or a prodrug thereof to the mammal;
(25) use of the compound of the above-mentioned (1) or a salt thereof or a prodrug thereof for the production of a prophylactic or therapeutic agent of diabetes mellitus;
(26) a production method of a compound represented by the formula

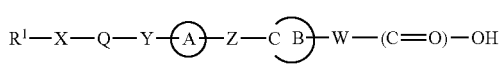

(I-4)

wherein
R¹ is an optionally substituted 5-membered heterocyclic group;

X is a bond, an oxygen atom, a sulfur atom, —CO—, —CS—, —CR³(OR⁴)— or —NR⁵— (R³ is a hydrogen atom or an optionally substituted hydrocarbon group, R⁴ is a hydrogen atom or a hydroxy-protecting group, and R⁵ is a hydrogen atom, an optionally substituted hydrocarbon group or an amino-protecting group);
Q is a divalent hydrocarbon group having 1 to 20 carbon atoms;
Y is a bond, an oxygen atom, a sulfur atom, —SO—, —SO₂—, —NR⁶—, —CONR⁶— or —NR⁶CO— (R⁶ is a hydrogen atom or an optionally substituted hydrocarbon group);
ring A
is an aromatic ring optionally further having 1 to 3 substituents;
Z is —(CH₂)ₙ—Z¹— or —Z¹—(CH₂)ₙ— (n is an integer of 0 to 8, Z¹ is a bond, an oxygen atom, a sulfur atom, —SO—, —SO₂—, —NR⁷—, —CONR⁷— or —NR⁷CO— (R⁷ is a hydrogen atom or an optionally substituted hydrocarbon group));
ring B
is a 5-membered heterocycle optionally further having 1 to 3 substituents; and
W is a divalent saturated hydrocarbon group having 1 to 20 carbon atoms,
or a salt thereof, which comprises subjecting a compound represented by the formula

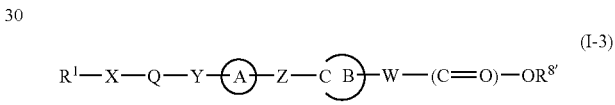

(I-3)

wherein R⁸' is an optionally substituted hydrocarbon group and other symbols are as defined above, or a salt thereof, to a hydrolysis reaction;

and the like.

In the formula (I), the "5-membered heterocyclic group" for R¹ is, for example, a 5-membered heterocyclic group containing, as ring-constituting atom(s) besides carbon atoms, 1 to 4 hetero atoms selected from an oxygen atom, a sulfur atom and a nitrogen atom.

Preferable examples of the "5-membered heterocyclic group" include 5-membered non-aromatic heterocyclic groups such as pyrrolidinyl (2-pyrrolidinyl, 3-pyrrolidinyl), imidazolidinyl (2-imidazolidinyl, 4-imidazolidinyl), pyrazolidinyl (2-pyrazolidinyl, 3-pyrazolidinyl, 4-pyrazolidinyl) and the like; and 5-membered aromatic heterocyclic groups such as furyl (2-furyl, 3-furyl), thienyl (2-thienyl, 3-thienyl), pyrrolyl (1-pyrrolyl, 2-pyrrolyl, 3-pyrrolyl), imidazolyl (1-imidazolyl, 2-imidazolyl, 4-imidazolyl, 5-imidazolyl), pyrazolyl (1-pyrazolyl, 3-pyrazolyl, 4-pyrazolyl), isoxazolyl (3-isoxazolyl, 4-isoxazolyl, 5-isoxazolyl), isothiazolyl (3-isothiazolyl, 4-isothiazolyl, 5-isothiazolyl), thiazolyl (2-thiazolyl, 4-thiazolyl, 5-thiazolyl), oxazolyl (2-oxazolyl, 4-oxazolyl, 5-oxazolyl), oxadiazolyl (1,2,4-oxadiazol-5-yl, 1,3,4-oxadiazol-2-yl), thiadiazolyl (1,3,4-thiadiazol-2-yl), triazolyl (1,2,4-triazol-1-yl, 1,2,4-triazol-3-yl, 1,2,3-triazol-1-yl, 1,2,3-triazol-2-yl, 1,2,3-triazol-4-yl), tetrazolyl (tetrazol-1-yl, tetrazol-5-yl) and the like.

The "5-membered heterocyclic group" for R¹ is preferably a 5-membered aromatic heterocyclic group, which is more preferably oxazolyl, thiazolyl, pyrazolyl or triazolyl. Of these, oxazolyl, thiazolyl and triazolyl are preferable.

The "5-membered heterocyclic group" for $R^1$ may have 1 to 4, preferably 1 to 3, substituents at substitutable position(s). Examples of the substituents include "a halogen atom", "a nitro group", "an optionally substituted aliphatic hydrocarbon group", "an optionally substituted alicyclic hydrocarbon group", "an optionally substituted aromatic hydrocarbon group", "an optionally substituted aromatic heterocyclic group", "an optionally substituted non-aromatic heterocyclic group", "an acyl group", "an optionally substituted amino group", "an optionally substituted hydroxy group", "an optionally substituted thiol group", and "an optionally esterified or amidated carboxyl group"

Examples of the "halogen atom" include fluorine, chlorine, bromine and iodine, with preference given to fluorine and chlorine.

The aliphatic hydrocarbon group of the "optionally substituted aliphatic hydrocarbon group" is exemplified by straight-chain or branched aliphatic hydrocarbon groups having 1 to 15 carbon atoms, such as an alkyl group, an alkenyl group and an alkynyl group.

Preferable examples of the alkyl group include alkyl groups having 1 to 10 carbon atoms, such as methyl, ethyl, propyl, isopropyl, butyl, isobutyl, sec.-butyl, t.-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl and decyl.

Preferable examples of the alkenyl group include alkenyl groups having 2 to 10 carbon atoms, such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl and 1-octenyl.

Preferable examples of the alkynyl group include alkynyl groups having 2 to 10 carbon atoms, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl and 1-octynyl.

Examples of the substituent of the "optionally substituted aliphatic hydrocarbon group" include cycloalkyl groups having 3 to 10 carbon atoms, aryl groups having 6 to 14 carbon atoms (e.g., phenyl, naphthyl), aromatic heterocyclic groups (e.g., thienyl, furyl, pyridyl, oxazolyl, thiazolyl etc.), non-aromatic heterocyclic groups (e.g., tetrahydrofuryl, morpholino, thiomorpholino, piperidino, pyrrolidinyl, piperazinyl etc.), an amino group, an amino group mono- or di-substituted by an alkyl group having 1 to 4 carbon atoms or an acyl group having 2 to 8 carbon atoms (e.g., alkanoyl groups etc.), an amidino group, an acyl group having 2 to 8 carbon atoms (e.g., alkanoyl groups etc.), a carbamoyl group, a carbamoyl group mono- or di-substituted by an alkyl group having 1 to 4 carbon atoms, a sulfamoyl group, a sulfamoyl group mono- or di-substituted by an alkyl group having 1 to 4 carbon atoms, a carboxyl group, alkoxycarbonyl groups having 2 to 8 carbon atoms, a hydroxy group, alkoxy groups having 1 to 6 carbon atoms which may be substituted by 1 to 3 halogen atoms (e.g., fluorine, chlorine, bromine, iodine etc.), alkenyloxy groups having 2 to 5 carbon atoms optionally substituted by 1 to 3 halogen atoms (e.g., fluorine, chlorine, bromine, iodine), cycloalkyloxy groups having 3 to 7 carbon atoms, aralkyloxy groups having 7 to 9 carbon atoms, aryloxy groups having 6 to 14 carbon atoms (e.g., phenyloxy, naphthyloxy etc.), a thiol group, alkylthio groups having 1 to 6 carbon atoms optionally substituted by 1 to 3 halogen atoms (e.g., fluorine, chlorine, bromine, iodine etc.), aralkylthio groups having 7 to 9 carbon atoms, arylthio groups having 6 to 14 carbon atoms (e.g., phenylthio, naphthylthio etc.), a sulfo group, a cyano group, an azide group, a nitro group, a nitroso group, halogen atoms (e.g., fluorine, chlorine, bromine, iodine) and the like. The number of the substituents is, for example, 1 to 3.

The alicyclic hydrocarbon group of the "optionally substituted alicyclic hydrocarbon group" is exemplified by saturated or unsaturated alicyclic hydrocarbon groups having 3 to 12 carbon atoms, such as a cycloalkyl group, a cycloalkenyl group and a cycloalkadienyl group.

Preferable examples of the cycloalkyl group include cycloalkyl groups having 3 to 10 carbon atoms, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl.

Preferable examples of the cycloalkenyl group include cycloalkenyl groups having 3 to 10 carbon atoms, such as 2-cyclopenten-1-yl, 3-cyclopenten-1-yl, 2-cyclohexen-1-yl and 3-cyclohexen-1-yl.

Preferable examples of the cycloalkadienyl group include cycloalkadienyl groups having 4 to 10 carbon atoms, such as 2,4-cyclopentadien-1-yl, 2,4-cyclohexadien-1-yl and 2,5-cyclohexadien-1-yl.

Preferable examples of the aromatic hydrocarbon group of the "optionally substituted aromatic hydrocarbon group" include aromatic hydrocarbon groups having 6 to 14 carbon atoms (e.g., aryl groups etc.), such as phenyl, naphthyl, anthryl, phenanthryl, acenaphthylenyl and biphenylyl, with preference given to phenyl, 1-naphthyl, 2-naphthyl and the like. The aromatic hydrocarbon group may be partially hydrogenated, and the partially hydrogenated aromatic hydrocarbon group is exemplified by tetrahydronaphthalenyl and the like.

As the aromatic heterocyclic group of the "optionally substituted aromatic heterocyclic group", for example, a monocyclic, bicyclic or tricyclic aromatic heterocyclic group containing, as ring-constituting atom(s) besides carbon atoms, 1 to 5 hetero atoms selected from an oxygen atom, a sulfur atom and a nitrogen atom and the like can be mentioned.

As preferable examples of the monocyclic aromatic heterocyclic group, for example, furyl, thienyl, pyrrolyl, oxazolyl, isoxazolyl, thiazolyl, isothiazolyl, imidazolyl, pyrazolyl, oxadiazolyl (1,2,3-oxadiazolyl, 1,2,4-oxadiazolyl, 1,3,4-oxadiazolyl), furazanyl, thiadiazolyl (1,2,3-thiadiazolyl, 1,2,4-thiadiazolyl, 1,3,4-thiadiazolyl), triazolyl (1,2,3-triazolyl, 1,2,4-triazolyl), tetrazolyl, pyridyl, pyrimidinyl, pyridazinyl, pyrazinyl and triazinyl can be mentioned.

As preferable examples of the bicyclic or tricyclic aromatic heterocyclic group, for example, benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthylidinyl, purinyl, pteridinyl, carbazolyl, α-carbonylyl, β-carbonylyl, γ-carbonylyl, acridinyl, phenoxazinyl, phenothiazinyl, phenazinyl, phenoxathiinyl, thianthrenyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl can be mentioned.

Preferable examples of the non-aromatic heterocyclic groups of the "optionally substituted non-aromatic heterocyclic group" include non-aromatic heterocyclic groups having 2 to 10 carbon atoms and containing 1 to 3 hetero atoms selected from an oxygen atom, a sulfur atom and a nitrogen atom, as ring constituting atom(s) besides carbon atoms, such as oxyranyl, azetidinyl, oxetanyl, thietanyl, pyrrolidinyl, tetrahydrofuryl, tetrahydropyranyl, morpholinyl, thiomorpholinyl, piperazinyl, pyrrolidinyl, piperidino, morpholino and thiomorpholino.

Examples of the substituents of the aforementioned "optionally substituted alicyclic hydrocarbon group", "optionally substituted aromatic hydrocarbon group", "optionally substituted aromatic heterocyclic group" and "optionally substituted non-aromatic heterocyclic group" include alkyl groups having 1 to 6 carbon atoms optionally substituted by 1 to 3 halogen atoms (e.g., fluorine, chlorine, bromine, iodine etc.), alkenyl groups having 2 to 6 carbon atoms optionally substituted by 1 to 3 halogen atoms (e.g., fluorine, chlorine, bromine, iodine), cycloalkyl groups having 3 to 10 carbon atoms, aryl groups having 6 to 14 carbon atoms (e.g., phenyl, naphthyl etc.), aromatic heterocyclic groups (e.g., thienyl, furyl, pyridyl, oxazolyl, thiazolyl etc.), non-aromatic heterocyclic groups (e.g., tetrahydrofuryl, morpholino, thiomorpholino, piperidino, pyrrolidinyl, piperazinyl etc.), aralkyl groups having 7 to 9 carbon atoms, an amino group, an amino group mono- or di-substituted by an alkyl group having 1 to 4 carbon atoms or an acyl group having 2 to 8 carbon atoms (e.g., alkanoyl group), an amidino group, acyl groups having 2 to 8 carbon atoms (e.g., alkanoyl group etc.), a carbamoyl group, a carbamoyl group mono- or di-substituted by an alkyl group having 1 to 4 carbon atoms, a sulfamoyl group, a sulfamoyl group mono- or di-substituted by an alkyl group having 1 to 4 carbon atoms, a carboxyl group, alkoxycarbonyl groups having 2 to 8 carbon atoms, a hydroxy group, alkoxy groups having 1 to 6 carbon atoms optionally substituted by 1 to 3 halogen atoms (e.g., fluorine, chlorine, bromine, iodine etc.), alkenyloxy groups having 2 to 5 carbon atoms optionally substituted by 1 to 3 halogen atoms (e.g., fluorine, chlorine, bromine, iodine etc.), cycloalkyloxy groups having 3 to 7 carbon atoms, aralkyloxy groups having 7 to 9 carbon atoms, aryloxy groups having 6 to 14 carbon atoms (e.g., phenyloxy, naphthyloxy), a thiol group, alkylthio groups having 1 to 6 carbon atoms optionally substituted by 1 to 3 halogen atoms (e.g., fluorine, chlorine, bromine, iodine etc.), aralkylthio groups having 7 to 9 carbon atoms, arylthio groups having 6 to 14 carbon atoms (e.g., phenylthio, naphthylthio etc.), a sulfo group, a cyano group, an azide group, a nitro group, a nitroso group, and halogen atoms (e.g., fluorine, chlorine, bromine, iodine), and the like. The number of the substituents is, for example, 1 to 3.

The acyl group is exemplified by acyl groups having 1 to 13 carbon atoms, specifically formyl and groups of the formulas: —$COR^{11}$, —$SO_2R^{11}$, —$SOR^{11}$ and —$PO_3R^{11}R^{12}$ wherein $R^{11}$ and $R^{12}$ may be the same or different and each is an optionally substituted hydrocarbon group or an optionally substituted aromatic heterocyclic group.

As the hydrocarbon group of the "optionally substituted hydrocarbon group" for $R^{11}$ or $R^{12}$, for example, an aliphatic hydrocarbon group, an alicyclic hydrocarbon group, an alicyclic-aliphatic hydrocarbon group, an aromatic aliphatic hydrocarbon group and an aromatic hydrocarbon group can be mentioned. The number of carbon atoms of these hydrocarbon groups is preferably 1 to 15.

As used herein, as the aliphatic hydrocarbon group, alicyclic hydrocarbon group and aromatic hydrocarbon group, those exemplified as the substituent of the aforementioned $R^1$ can be mentioned.

The alicyclic-aliphatic hydrocarbon group is exemplified by those resulting from the binding of the aforementioned alicyclic hydrocarbon group and aliphatic hydrocarbon group (e.g., cycloalkyl-alkyl groups, cycloalkenyl-alkyl groups), with preference given to alicyclic-aliphatic hydrocarbon groups having 4 to 9 carbon atoms. Examples of the alicyclic-aliphatic hydrocarbon group include cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl.

The aromatic-aliphatic hydrocarbon group is preferably aromatic-aliphatic hydrocarbon group having 7 to 13 carbon atoms (e.g., an aralkyl group having 7 to 13 carbon atoms, an arylalkenyl group having 8 to 13 carbon atoms). Examples of the aromatic-aliphatic hydrocarbon group include phenylalkyl having 7 to 9 carbon atoms, such as benzyl, phenethyl, 1-phenylethyl, 1-phenylpropyl, 2-phenylpropyl and 3-phenylpropyl; naphthylalkyl having 11 to 13 carbon atoms, such as α-naphthylmethyl, α-naphthylethyl, β-naphthylmethyl and β-naphthylethyl; phenylalkenyl having 8 to 10 carbon atoms, such as styryl; and naphthylalkenyl having 12 to 13 carbon atoms, such as 2-(2-naphthylvinyl).

The hydrocarbon group is preferably an alkyl group having 1 to 10 carbon atoms, an alkenyl group having 2 to 10 carbon atoms, a cycloalkyl group having 3 to 10 carbon atoms, a cycloalkenyl group having 3 to 10 carbon atoms, an aryl group having 6 to 14 carbon atoms and the like.

As the aromatic heterocyclic group of the "optionally substituted aromatic heterocyclic group" for $R^{11}$ or $R^{12}$, for example, a 5- to 7-membered monocyclic aromatic heterocyclic group containing, as ring-constituting atom(s) besides carbon atoms, 1 to 4 hetero atoms selected from an oxygen atom, a sulfur atom and a nitrogen atom, and a fused ring group thereof can be mentioned. As the fused ring group, for example, a group wherein these 5- to 7-membered monocyclic aromatic heterocyclic groups are condensed with a 6-membered ring containing 1 or 2 nitrogen atoms (e.g., pyridine), a benzene ring or a 5-membered ring having one sulfur atom, and the like can be mentioned.

Preferable examples of the aromatic heterocyclic group include pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyridazinyl (3-pyridazinyl, 4-pyridazinyl), pyrazinyl (2-pyrazinyl), pyrrolyl (1-pyrrolyl, 2-pyrrolyl, 3-pyrrolyl), thienyl (2-thienyl, 3-thienyl), furyl (2-furyl, 3-furyl), imidazolyl (1-imidazolyl, 2-imidazolyl, 4-imidazolyl, 5-imidazolyl), pyrazolyl (1-pyrazolyl, 3-pyrazolyl, 4-pyrazolyl), isoxazolyl (3-isoxazolyl, 4-isoxazolyl, 5-isoxazolyl), isothiazolyl (3-isothiazolyl, 4-isothiazolyl, 5-isothiazolyl), thiazolyl (2-thiazolyl, 4-thiazolyl, 5-thiazolyl), oxazolyl (2-oxazolyl, 4-oxazolyl, 5-oxazolyl), oxadiazolyl (1,2,4-oxadiazol-5-yl, 1,3,4-oxadiazol-2-yl), thiadiazolyl (1,3,4-thiadiazol-2-yl), triazolyl (1,2,4-triazol-1-yl, 1,2,4-triazol-3-yl, 1,2,3-triazol-1-yl, 1,2,3-triazol-2-yl, 1,2,3-triazol-4-yl), tetrazolyl (tetrazol-1-yl, tetrazol-5-yl), quinolyl (2-quinolyl, 3-quinolyl, 4-quinolyl), quinazolyl (2-quinazolyl, 4-quinazolyl), quinoxalyl (2-quinoxalyl), benzoxazolyl (2-benzoxazolyl), benzothiazolyl (2-benzothiazolyl), benzimidazolyl (benzimidazol-1-yl, benzimidazol-2-yl), indolyl (indol-1-yl, indol-3-yl), indazolyl (1H-indazol-3-yl), pyrrolopyrazinyl (1H-pyrrolo[2,3-b]pyrazin-2-yl), pyrrolopyridinyl (1H-pyrrolo[2,3-b]pyridin-6-yl), imidazopyridinyl (imidazo[1,2-a]pyridin-2-yl, 1H-imidazo[4,5-b]pyridin-2-yl, 1H-imidazo[4,5-c]pyridin-2-yl), imidazopyrazinyl (1H-imidazo[4,5-b]pyrazin-2-yl), oxophthalazinyl (1-oxo-2(1H)-phthalazinyl) and the like. Of these, thienyl, furyl, pyridyl and the like are preferable.

The hydrocarbon group or aromatic heterocyclic group for $R^{11}$ or $R^{12}$ may have 1 to 3 substituents at substitutable position(s). Examples of such substituents include $C_{1-6}$ alkyl groups optionally substituted by 1 to 3 halogen atoms (e.g., fluorine, chlorine, iodine etc.), $C_{1-6}$ alkoxy groups optionally substituted by 1 to 3 halogen atoms (e.g., fluorine, chlorine, bromine, iodine etc.), halogen atoms (e.g., fluorine, chlorine, bromine, iodine etc.), nitro, hydroxy, amino and the like.

Preferable examples of the acyl group include acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, isonicotinoyl and the like.

The "optionally substituted amino group" is exemplified by an amino group optionally mono- or di-substituted by an alkyl group having 1 to 10 carbon atoms, an alkenyl group having 2 to 10 carbon atoms, a cycloalkyl group having 3 to 10 carbon atoms, a cycloalkenyl group having 3 to 10 carbon atoms, an aryl group having 6 to 14 carbon atoms or an acyl group having 1 to 13 carbon atoms. As these groups, those exemplified as the substituent of the aforementioned $R^1$ can be mentioned. Here, the acyl group having 1 to 13 carbon atoms is preferably an alkanoyl group having 2 to 10 carbon atoms, an arylcarbonyl group having 7 to 13 carbon atoms, and the like.

Examples of the substituted amino group include methylamino, dimethylamino, ethylamino, diethylamino, propylamino, dibutylamino, diallylamino, cyclohexylamino, acetylamino, propionylamino, benzoylamino, phenylamino, N-methyl-N-phenylamino and the like.

As the "optionally substituted hydroxy group", for example, a hydroxy group optionally substituted by an optionally substituted alkyl group having 1 to 10 carbon atoms, an optionally substituted alkenyl group having 2 to 10 carbon atoms, an optionally substituted aralkyl group having 7 to 13 carbon atoms, an optionally substituted acyl group having 1 to 13 carbon atoms or an optionally substituted aryl group having 6 to 14 carbon atoms can be mentioned. As these alkyl group, alkenyl group, acyl group and aryl group, those exemplified as the substituent for the aforementioned $R^1$ can be mentioned. As the "aralkyl group having 7 to 13 carbon atoms", that exemplified as the aforementioned hydrocarbon group for $R^{11}$ and $R^{12}$ can be mentioned.

Examples of the substituents which may be possessed by these alkyl, alkenyl, aralkyl, acyl and aryl groups include halogen atoms (e.g., fluorine, chlorine, bromine, iodine etc.), alkoxy groups having 1 to 3 carbon atoms and the like. The number of the substituents is, for example, 1 to 2.

Examples of the substituted hydroxy group include an alkoxy group, an alkenyloxy group, an aralkyloxy group, an acyloxy group and an aryloxy group, each of which is optionally substituted.

Preferable examples of the alkoxy group include alkoxy groups having 1 to 10 carbon atoms, such as methoxy, ethoxy, propoxy, isopropoxy, butoxy, isobutoxy, sec.-butoxy, t.-butoxy, pentyloxy, isopentyloxy, neopentyloxy, hexyloxy, heptyloxy, nonyloxy, cyclobutoxy, cyclopentyloxy, cyclohexyloxy and the like.

Preferable examples of the alkenyloxy group include alkenyloxy groups having 2 to 10 carbon atoms, such as allyloxy, crotyloxy, 2-pentenyloxy, 3-hexenyloxy, 2-cyclopentenylmethoxy, 2-cyclohexenylmethoxy and the like.

Preferable examples of the aralkyloxy group include aralkyloxy groups having 7 to 10 carbon atoms, such as phenyl-$C_{1-4}$ alkyloxy (e.g., benzyloxy, phenethyloxy) and the like.

Preferable examples of the acyloxy group include acyloxy groups having 2 to 13 carbon atoms, with more preference given to alkanoyloxy groups having 2 to 4 carbon atoms (e.g., acetyloxy, propionyloxy, butyryloxy, isobutyryloxy).

Preferable examples of the aryloxy group include aryloxy groups having 6 to 14 carbon atoms, such as phenoxy, naphthyloxy and the like.

The aforementioned alkoxy group, alkenyloxy group, aralkyloxy group, acyloxy group and aryloxy group may have 1 or 2 substituents at substitutable position(s). Examples of such substituent include halogen atoms (e.g., fluorine, chlorine, bromine, iodine etc.), $C_{1-6}$ alkoxy groups optionally substituted by 1 to 3 halogen atoms (e.g., fluorine, chlorine, bromine, iodine etc.), hydroxy, nitro, amino and the like. For example, examples of the substituted aryloxy groups include 4-chlorophenoxy and 2-methoxyphenoxy.

The optionally substituted thiol group is exemplified by a thiol group optionally substituted by an alkyl group having 1 to 10 carbon atoms, a cycloalkyl group having 3 to 10 carbon atoms, an aralkyl group having 7 to 13 carbon atoms, an acyl group having 2 to 13 carbon atoms, an aryl group having 6 to 14 carbon atoms, a heteroaryl group or the like. As the alkyl group, cycloalkyl group, acyl group or aryl group, those exemplified as the aforementioned substituent for the aforementioned $R^1$ can be mentioned. As the aralkyl group, those exemplified as the aforementioned hydrocarbon group for $R^{11}$ and $R^{12}$ can be mentioned. Preferable examples of the heteroaryl group include pyridyl (e.g., 2-pyridyl, 3-pyridyl), imidazolyl (e.g., 2-imidazolyl), triazolyl (e.g., 1,2,4-triazol-5-yl) and the like.

Examples of the substituted thiol group include an alkylthio, a cycloalkylthio, an aralkylthio, an acylthio, an arylthio, a heteroarylthio and the like.

Preferable examples of the alkylthio group include alkylthio groups having 1 to 10 carbon atoms, such as methylthio, ethylthio, propylthio, isopropylthio, butylthio, isobutylthio, sec.-butylthio, t.-butylthio, pentylthio, isopentylthio, neopentylthio, hexylthio, heptylthio, nonylthio and the like.

Preferable examples of the cycloalkylthio group include cycloalkylthio groups having 3 to 10 carbon atoms, such as cyclobutylthio, cyclopentylthio, cyclohexylthio and the like.

Preferable examples of the aralkylthio group include aralkylthio groups having 7 to 10 carbon atoms, such as phenyl-$C_{1-4}$ alkylthio (e.g., benzylthio, phenethylthio etc.) and the like.

Preferable examples of the acylthio group include acylthio groups having 2 to 13 carbon atoms, with greater preference given to alkanoylthio groups having 2 to 4 carbon atoms (e.g., acetylthio, propionylthio, butyrylthio, isobutyrylthio etc.) and the like.

Preferable examples of the arylthio group include arylthio groups having 6 to 14 carbon atoms, such as phenylthio, naphthylthio and the like.

Preferable examples of the heteroarylthio group include pyridylthio (e.g., 2-pyridylthio, 3-pyridylthio), imidazolylthio (e.g., 2-imidazolylthio) and triazolylthio (e.g., 1,2,4-triazol-5-ylthio).

Esterified carboxyl group of the optionally esterified carboxyl group is exemplified by alkoxycarbonyl groups having 2 to 5 carbon atoms (e.g., methoxycarbonyl, ethoxycarbonyl, propoxycarbonyl, butoxycarbonyl), aralkyloxycarbonyl groups having 8 to 10 carbon atoms (e.g., benzyloxycarbonyl) and aryloxycarbonyl groups having 7 to 15 carbon atoms (e.g., phenoxycarbonyl, p-tolyloxycarbonyl) which may be substituted by 1 or 2 alkyl groups having 1 to 3 carbon atoms.

Amidated carboxyl group of the optionally amidated carboxyl group is exemplified by groups of the formula: —CON($R^{13}$)($R^{14}$) wherein $R^{13}$ and $R^{14}$ may be the same or different and each is a hydrogen atom, an optionally substituted hydrocarbon group or an optionally substituted heterocyclic group.

Here, the hydrocarbon group of the "optionally substituted hydrocarbon group" for $R^{13}$ and $R^{14}$ is exemplified by those mentioned to exemplify the above-mentioned $R^{11}$ and $R^{12}$. In addition, the heterocyclic group of the "optionally substituted heterocyclic group" for $R^{13}$ and $R^{14}$ is exemplified by the aromatic heterocyclic groups and non-aromatic heterocyclic groups mentioned as examples of the substituent for $R^1$. The heterocyclic group may have 1 to 3 substituents at substitutable position(s). Examples of such substituent include halogen atoms (e.g., fluorine, chlorine, bromine, iodine etc.), $C_{1-6}$ alkyl groups optionally substituted by 1 to 3 halogen atoms (e.g., fluorine, chlorine, bromine, iodine etc.), $C_{1-6}$ alkoxy groups optionally substituted by 1 to 3 halogen atoms (e.g., fluorine, chlorine, bromine, iodine etc.), nitro, hydroxy, amino and the like.

The substituent for $R^1$ is preferably
1) an alkyl group having 1 to 10 (preferably 1 to 4) carbon atoms, which may have 1 to 3 substituents selected from alkoxy groups having 1 to 6 carbon atoms optionally substituted by 1 to 3 halogen atoms (e.g., fluorine, chlorine, bromine, iodine etc.), halogen atoms (e.g., fluorine, chlorine, bromine, iodine etc.), nitro, hydroxy and amino;
2) a cycloalkyl group having 3 to 10 (preferably 3 to 7) carbon atoms, which may have 1 to 3 substituents selected from alkyl groups having 1 to 6 carbon atoms optionally substituted by 1 to 3 halogen atoms (e.g., fluorine, chlorine, bromine, iodine etc.), alkoxy groups having 1 to 6 carbon atoms optionally substituted by 1 to 3 halogen atoms (e.g., fluorine, chlorine, bromine, iodine etc.), halogen atoms (e.g., fluorine, chlorine, bromine, iodine etc.), nitro, hydroxy and amino;
3) an aryl group having 6 to 14 carbon atoms (preferably phenyl, naphthyl etc.) which may have 1 to 3 substituents selected from alkyl groups having 1 to 6 carbon atoms optionally substituted by 1 to 3 halogen atoms (e.g., fluorine, chlorine, bromine, iodine etc.), alkoxy groups having 1 to 6 carbon atoms optionally substituted by 1 to 3 halogen atoms (e.g., fluorine, chlorine, bromine, iodine etc.), halogen atoms (e.g., fluorine, chlorine, bromine, iodine etc.), nitro, hydroxy and amino;
4) an aromatic heterocyclic group (preferably furyl, thienyl, pyridyl, pyrazinyl etc.) which may have 1 to 3 substituents selected from alkyl groups having 1 to 6 carbon atoms optionally substituted by 1 to 3 halogen atoms (e.g., fluorine, chlorine, bromine, iodine etc.), alkoxy groups having 1 to 6 carbon atoms optionally substituted by 1 to 3 halogen atoms (e.g., fluorine, chlorine, bromine, iodine etc.), halogen atoms (e.g., fluorine, chlorine, bromine, iodine etc), nitro, hydroxy and amino; and the like. The number of the substituents for $R^1$ is preferably 1 to 3, more preferably 1 or 2.

The substituent for $R^1$ is more preferably an alkyl group having 1 to 4 carbon atoms, furyl, thienyl, phenyl, naphthyl and the like.

$R^1$ is preferably oxazolyl, thiazolyl, pyrazolyl or triazolyl, each optionally having 1 to 3 substituents selected from
1) alkyl groups having 1 to 10 (preferably 1 to 4) carbon atoms, which may have 1 to 3 substituents selected from alkoxy groups having 1 to 6 carbon atoms optionally substituted by 1 to 3 halogen atoms (e.g., fluorine, chlorine, bromine, iodine etc.), halogen atoms (e.g., fluorine, chlorine, bromine, iodine etc.), nitro, hydroxy and amino;
2) cycloalkyl groups having 3 to 10 (preferably 3 to 7) carbon atoms, which may have 1 to 3 substituents selected from alkyl groups having 1 to 6 carbon atoms optionally substituted by 1 to 3 halogen atoms (e.g., fluorine, chlorine, bromine, iodine etc.), alkoxy groups having 1 to 6 carbon atoms optionally substituted by 1 to 3 halogen atoms (e.g., fluorine, chlorine, bromine, iodine etc.), halogen atoms (e.g., fluorine, chlorine, bromine, iodine etc.), nitro, hydroxy and amino;
3) aryl groups having 6 to 14 carbon atoms (preferably phenyl, naphthyl etc.) which may have 1 to 3 substituents selected from alkyl groups having 1 to 6 carbon atoms optionally substituted by 1 to 3 halogen atoms (e.g., fluorine, chlorine, bromine, iodine etc.), alkoxy groups having 1 to 6 carbon atoms optionally substituted by 1 to 3 halogen atoms (e.g., fluorine, chlorine, bromine, iodine etc.), halogen atoms (e.g., fluorine, chlorine, bromine, iodine etc.), nitro, hydroxy and amino;
4) aromatic heterocyclic groups (preferably furyl, thienyl, pyridyl, pyrazinyl etc.) which may have 1 to 3 substituents selected from alkyl groups having 1 to 6 carbon atoms optionally substituted by 1 to 3 halogen atoms (e.g., fluorine, chlorine, bromine, iodine etc.), alkoxy groups having 1 to 6 carbon atoms optionally substituted by 1 to 3 halogen atoms (e.g., fluorine, chlorine, bromine, iodine etc.), halogen atoms (e.g., fluorine, chlorine, bromine, iodine etc.), nitro, hydroxy and amino; and the like.

$R^1$ is more preferably oxazolyl, thiazolyl or triazolyl, each optionally having 1 or 2 substituents selected from alkyl groups having 1 to 3 carbon atoms, cycloalkyl groups having 3 to 7 carbon atoms, furyl, thienyl, phenyl and naphthyl.

In the formula (I), X is a bond, an oxygen atom, a sulfur atom, —CO—, —CS—, —$CR^3(OR^4)$— or —$NR^5$— ($R^3$ is a hydrogen atom or an optionally substituted hydrocarbon group, $R^4$ is a hydrogen atom or a hydroxy-protecting group, $R^5$ is a hydrogen atom, an optionally substituted hydrocarbon group or an amino-protecting group). X is preferably a bond or —$NR^5$— ($R^5$ is as defined above), more preferably a bond.

Here, the "optionally substituted hydrocarbon group" for $R^3$ or $R^5$ is exemplified by that mentioned as examples of $R^{11}$ and $R^{12}$ above. Said "optionally substituted hydrocarbon group" is preferably optionally substituted alkyl groups having 1 to 4 carbon atoms, such as methyl, ethyl, propyl, isopropyl, butyl, isobutyl, sec.-butyl, t.-butyl and the like. Said alkyl groups may have 1 to 3 substituents at substitutable position(s). Examples of such substituents include halogen atoms (e.g., fluorine, chlorine, bromine, iodine), alkoxy groups having 1 to 4 carbon atoms (e.g., methoxy, ethoxy, propoxy, isopropoxy, butoxy, isobutoxy, sec.-butoxy, t.-butoxy etc.), hydroxy, nitro, amino and acyl groups having 1 to 4 carbon atoms (e.g., alkanoyl groups having 1 to 4 carbon atoms, such as formyl, acetyl and propionyl).

$R^3$ and $R^5$ are preferably hydrogen atoms or alkyl groups having 1 to 4 carbon atoms.

Examples of the hydroxy-protecting group for $R^4$ include $C_{1-6}$ alkyl (e.g., methyl, ethyl, propyl, isopropyl, butyl, t.-butyl etc.), phenyl, trityl, $C_{7-10}$ aralkyl (e.g., benzyl etc.), formyl, $C_{1-6}$ alkyl-carbonyl (e.g., acetyl, propionyl etc.), benzoyl, $C_{7-10}$ aralkyl-carbonyl (e.g., benzylcarbonyl etc.), 2-tetrahydropyranyl, 2-tetrahydrofuranyl, silyl (e.g., trimethylsilyl, triethylsilyl, dimethylphenylsilyl, t.-butyldimethylsilyl, t.-butyldiethylsilyl etc.), $C_{2-6}$ alkenyl (e.g., 1-allyl etc.), and the like. These groups may be substituted by 1 to 3 halogen atoms (e.g., fluorine, chlorine, bromine, iodine etc.), $C_{1-6}$ alkyl (e.g., methyl, ethyl, propyl etc.), $C_{1-6}$ alkoxy (e.g., methoxy, ethoxy, propoxy etc.), nitro etc., and the like.

As the amino-protecting group for $R^5$, for example, formyl, $C_{1-6}$ alkyl-carbonyl (e.g., acetyl, propionyl etc.), $C_{1-6}$ alkoxy-carbonyl (e.g., methoxycarbonyl, ethoxycarbonyl, t.-butoxycarbonyl etc.), benzoyl, $C_{7-10}$ aralkyl-carbonyl (e.g., benzylcarbonyl etc.), $C_{7-14}$ aralkyloxy-carbonyl (e.g., benzyloxycarbonyl, 9-fluorenylmethoxycarbonyl etc.), trityl, phthaloyl, N,N-dimethylaminomethylene, silyl (e.g., trimethylsilyl, triethylsilyl, dimethylphenylsilyl, t.-butyldimethylsilyl, tert-butyldiethylsilyl and the like), $C_{2-6}$ alkenyl (e.g., 1-allyl etc.) and the like can be mentioned. These groups may be substituted by 1 to 3 halogen atoms (e.g., fluorine, chlorine, bromine, iodine etc.), $C_{1-6}$ alkoxy (e.g., methoxy, ethoxy, propoxy etc.), nitro and the like.

In the formula (I), the "divalent hydrocarbon group having 1 to 20 carbon atoms" for Q is exemplified by "divalent non-cyclic hydrocarbon groups", "divalent cyclic hydrocarbon groups", and divalent groups obtained by combining one or more "divalent non-cyclic hydrocarbon groups" and one or more "divalent cyclic hydrocarbon groups".

Here, examples of the "divalent non-cyclic hydrocarbon groups" include alkylenes having 1 to 20 carbon atoms, alkenylenes having 2 to 20 carbon atoms, and alkynylenes having 2 to 20 carbon atoms.

Examples of the "divalent cyclic hydrocarbon groups" include divalent groups obtained by removing two optional hydrogen atoms from cycloalkanes having 5 to 20 carbon atoms, cycloalkenes having 5 to 20 carbon atoms, or aromatic hydrocarbons having 6 to 20 carbon atoms (e.g., benzene, naphthalene, indene, anthracene etc.). Specifically, there may be mentioned 1,2-cyclopentylene, 1,3-cyclopentylene, 1,2-cyclohexylene, 1,3-cyclohexylene, 1,4-cyclohexylene, 1,2-cycloheptylene, 1,3-cycloheptylene, 1,4-cycloheptylene, 3-cyclohexen-1,4-ylene, 3-cyclohexen-1,2-ylene, 2,5-cyclohexadien-1,4-ylene, 1,2-phenylene, 1,3-phenylene, 1,4-phenylene, 1,4-naphthylene, 1,6-naphthylene, 2,6-naphthylene, 2,7-naphthylene, 1,5-indenylene, 2,5-indenylene and the like.

Q is preferably a divalent hydrocarbon group having 1 to 6 carbon atoms. Particularly, (1) $C_{1-6}$ alkylene (e.g., —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$(CH(CH_3))_2$—, —$(CH_2)_2C(CH_3)_2$—, —$(CH_2)_3C(CH_3)_2$— etc.);

(2) $C_{2-6}$ alkenylene (e.g., —CH=CH—; —$CH_2$—CH=CH—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$— etc.);

(3) $C_{2-6}$ alkynylene (e.g., —C≡C—, —$CH_2$—C≡C—, —$CH_2$—C≡C—$CH_2$—$CH_2$— etc.) and the like are preferable.

Q is more preferably $C_{1-6}$ alkylene or $C_{2-6}$ alkenylene, of which —$CH_2$—, —$(CH_2)_2$—, —$(CH_2)_3$—, —$(CH_2)_4$—, —CH=CH— and the like are preferable. Q is particularly preferably —$CH_2$—, —$(CH_2)_2$— and the like.

In the formula (I), Y is a bond, an oxygen atom, a sulfur atom, —SO—, —$SO_2$—, —$NR^6$—, —$CONR^6$— or —$NR^6CO$— ($R^6$ is a hydrogen atom or an optionally substituted hydrocarbon group). Y is preferably an oxygen atom or —$NR^6$— ($R^6$ is as defined above), more preferably an oxygen atom.

As the "optionally substituted hydrocarbon group" for $R^6$, those exemplified for the aforementioned $R^{11}$ and $R^{12}$ can be mentioned. Of these, alkyl groups having 1 to 6 carbon atoms are preferable.

As the "aromatic ring" of the "aromatic ring optionally further having 1 to 3 substituents" represented by ring A in the formula (I), for example, a benzene ring, a fused aromatic hydrocarbon ring, a 5- or 6-membered aromatic heterocycle, a fused aromatic heterocycle and the like can be mentioned.

Here, as the "fused aromatic hydrocarbon ring", for example, a fused aromatic hydrocarbon having 9 to 14 carbon atoms and the like can be mentioned. Specifically, naphthalene, indene, fluorene, anthracene and the like can be mentioned.

As the "5- or 6-membered aromatic heterocycle", for example, a 5- or 6-membered aromatic heterocycle containing, besides carbon atoms, 1 to 3 hetero atoms selected from a nitrogen atom, a sulfur atom and an oxygen atom, and the like can be mentioned. Specifically, thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, furazan and the like can be mentioned.

As the "fused aromatic heterocycle", for example, a 9- to 14-membered (preferably 9- or 10-membered) fused aromatic heterocycle containing, besides carbon atoms, 1 to 4 hetero atoms selected from a nitrogen atom, a sulfur atom and an oxygen atom, and the like can be mentioned. Specifically, benzofuran, benzothiophene, benzimidazole, benzoxazole, benzothiazole, benzisothiazole, naphtho[2,3-b]thiophene, isoquinoline, quinoline, indole, quinoxaline, phenanthridine, phenothiazine, phenoxazine, phthalazine, naphthyridine, quinazoline, cinnoline, carbazole, β-carboline, acridine, phenazine, phthalimide and the like can be mentioned.

The "aromatic ring" is preferably a benzene ring, a fused aromatic hydrocarbon ring having 9 to 14 carbon atoms (preferably naphthalene etc.), a 5- or 6-membered aromatic heterocycle (preferably pyridine, oxazole, isoxazole, thiazole, oxadiazole etc.) and the like. The "aromatic ring" is more preferably a benzene ring, a pyridine ring or an isoxazole ring, specifically preferably a benzene ring or a pyridine ring.

When the aromatic ring represented by ring A in the formula (I) is a benzene ring or a pyridine ring, the relationship between Y and Z, which are substituents on the ring A, is preferably para position.

That is, when the aromatic ring represented by ring A in the formula (I) is a benzene ring,

is preferably

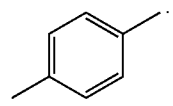

When the aromatic ring represented by ring A is a pyridine ring,

is preferably

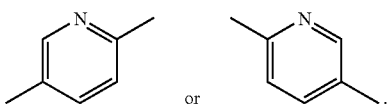

As the "substituent" of the "aromatic ring optionally further having 1 to 3 substituents" represented by ring A, an optionally substituted aliphatic hydrocarbon group (preferably alkyl group), an optionally substituted hydroxy group, a halogen atom, an acyl group, a nitro group, an optionally substituted amino group and the like can be mentioned. As these substituents, those exemplified as the substituent for $R^1$ can be used. The substituent of the ring A is preferably an alkyl group having 1 to 4 carbon atoms, a hydroxy group, an alkoxy group having 1 to 4 carbon atoms (preferably methoxy), an aralkyloxy group having 7 to 10 carbon atoms or a halogen atom.

In the formula (I), Z is —$(CH_2)_n$—$Z^1$— or —$Z^1$—$(CH_2)_n$— (n is an integer of 1 to 8 and $Z^1$ is a bond, an oxygen atom, a sulfur atom, —SO—, —$SO_2$—, —$NR^7$—, —$CONR^7$— or —$NR^7CO$— ($R^7$ is a hydrogen atom or an optionally substituted hydrocarbon group).

As used herein, as the "optionally substituted hydrocarbon group" for $R^7$, those exemplified for the aforementioned $R^{11}$ and $R^{12}$ can be mentioned, with preference given to an alkyl having 1 to 4 carbon atoms (e.g., methyl, ethyl, propyl and the like).

$R^7$ is preferably a hydrogen atom or an alkyl having 1 to 4 carbon atoms (e.g., methyl, ethyl, propyl and the like).

n is preferably an integer of 0 to 3, more preferably an integer of 1 to 3.

$Z^1$ is preferably a bond, an oxygen atom, a sulfur atom, —$NR^7$—, —$CONR^7$— or —$NR^7CO$— ($R^7$ is as defined above). As used herein, $R^7$ is preferably a hydrogen atom or an alkyl having 1 to 4 carbon atoms.

In the formula (I), when n is an integer of 1 to 8, then $Z^1$ is preferably a bond, an oxygen atom, a sulfur atom, —$NR^7$—, —$CONR^7$— or —$NR^7CO$— ($R^7$ is as defined above), and when n is 0, then $Z^1$ is preferably an oxygen atom, a sulfur atom, —SO—, —$SO_2$— or —$NR^7$— ($R^7$ is as defined above).

Z is preferably —$(CH_2)_n$—$Z^1$—. As used herein, n is preferably an integer of 0 to 2 (preferably 1), and $Z^1$ is preferably a bond, an oxygen atom or a sulfur atom (preferably an oxygen atom).

In the formula (I), as the "5-membered heterocycle" represented by ring B, for example, a 5-membered heterocycle containing, as ring-constituting atom(s) besides carbon atoms, 1 to 4 hetero atoms selected from an oxygen atom, a sulfur atom and a nitrogen atom can be mentioned.

Preferable examples of the "5-membered heterocycle" include 5-membered non-aromatic heterocycles such as pyrrolidine, imidazolidine, pyrazolidine and the like; and 5-membered aromatic heterocycles such as furan, thiophene, pyrrole, imidazole, pyrazole, isoxazole, isothiazole, thiazole, oxazole, oxadiazole, thiadiazole, triazole, tetrazole and the like.

The "5-membered heterocycle" for ring B is preferably a 5-membered aromatic heterocycle, more preferably nitrogen-containing 5-membered heterocycles such as an imidazole ring, a pyrazole ring, an oxazole ring, a thiazole ring, a triazole ring and the like. Of these, a pyrazole ring, an oxazole ring, a thiazole ring and the like are preferable, in particular, a pyrazole ring is preferable.

The ring B may have 1 to 3, preferably 1 or 2, substituents at substitutable position(s). As such substituents, for example, "a halogen atom", "nitro group", "an optionally substituted aliphatic hydrocarbon group", "an optionally substituted alicyclic hydrocarbon group", "an optionally substituted aromatic hydrocarbon group", "an optionally substituted aromatic heterocyclic group", "an optionally substituted non-aromatic heterocyclic group", "an acyl group", "an optionally substituted amino group", "an optionally substituted hydroxy group", "an optionally substituted thiol group", "an optionally esterified or amidated carboxyl group" and the like can be mentioned. As these substituents, those exemplified as the substituent for $R^1$ can be used.

In the formula (I), when ring B is a nitrogen-containing 5-membered heterocycle, the nitrogen-containing 5-membered heterocycle does not have, on the ring-constituting N atom, a substituent represented by the formula:

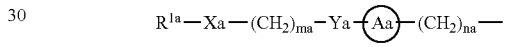

wherein $R^{1a}$ is an optionally substituted hydrocarbon group or an optionally substituted heterocyclic group;

Xa is a bond, an oxygen atom, a sulfur atom, —CO—, —CS—, —$CR^{2a}(OR^{3a})$— or —$NR^{4a}$— ($R^{2a}$ and $R^{4a}$ are each a hydrogen atom or an optionally substituted hydrocarbon group, $R^{3a}$ is a hydrogen atom or a hydroxy-protecting group);

ma is an integer of 0 to 3;

Ya is an oxygen atom, a sulfur atom, —SO—, —$SO_2$—, —$NR^{5a}$—, —$CONR^{5a}$— or —$NR^{5a}CO$— ($R^{5a}$ is a hydrogen atom or an optionally substituted hydrocarbon group);

ring Aa is an aromatic ring optionally having 1 to 3 substituents; and na is an integer of 1 to 8.

The "substituent" of the ring B is preferably a hydrocarbon group, more preferably an alkyl group having 1 to 10 carbon atoms (preferably methyl and the like), an aryl group having 6 to 14 carbon atoms—alkyl group having 1 to 10 carbon atoms (e.g., benzyl and the like), an optionally partially hydrogenated aryl group having 6 to 14 carbon atoms (preferably phenyl, naphthyl, tetrahydronaphthalenyl etc.) and the like.

In the formula (I), as the "divalent saturated hydrocarbon group having 1 to 20 carbon atoms" for W, saturated ones from those exemplified as the aforementioned Q can be mentioned.

W is preferably a divalent saturated hydrocarbon group having 1 to 6 carbon atoms, more preferably a $C_{1-6}$ alkylene, particularly preferably —$CH_2$—, —$(CH_2)_2$— and the like.

In the formula (I), $R^2$ is —$OR^8$ ($R^8$ is a hydrogen atom or an optionally substituted hydrocarbon group) or —$NR^9R^{10}$ ($R^9$ and $R^{10}$ are the same or different and each is a hydrogen atom, an optionally substituted hydrocarbon group, an optionally substituted heterocyclic group or an acyl group, or $R^9$ and $R^{10}$ may be linked to form an optionally substituted ring together with the adjacent nitrogen atom).

As the "optionally substituted hydrocarbon group" for $R^8$, those exemplified as the aforementioned $R^{11}$ and $R^{12}$ can be mentioned.

The "optionally substituted hydrocarbon group" is preferably an "alkyl group having 1 to 4 carbon atoms" and the like. As used herein, as the "alkyl group having 1 to 4 carbon atoms", for example, methyl, ethyl, propyl, butyl, isobutyl, sec.-butyl, t.-butyl and the like can be mentioned, with particular preference given to methyl and ethyl.

As the "optionally substituted hydrocarbon group" for $R^9$ or $R^{10}$, those exemplified as $R^{11}$ and $R^{12}$ can be mentioned. As the "optionally substituted heterocyclic group" for $R^9$ or $R^{10}$, those exemplified as $R^{13}$ and $R^{14}$ can be mentioned.

As the "acyl group" for $R^9$ or $R^{10}$, the "acyl group" exemplified as the substituent for $R^1$ can be mentioned.

As the ring formed by $R^9$ and $R^{10}$ in combination together with the adjacent nitrogen atom, for example, a 5- to 7-membered nitrogen-containing heterocycle can be mentioned. As preferable examples of the 5- to 7-membered nitrogen-containing heterocycle, pyrrolidine, piperidine, hexamethylenimine, morpholine, thiomorpholine, piperazine and the like can be mentioned.

The "ring formed by $R^9$ and $R^{10}$ in combination together with the adjacent nitrogen atom" may be a ring (optionally substituted ring), which may have 1 to 3 substituents at substitutable position(s). As such substituent, for example, a halogen atom (e.g., fluorine, chlorine, bromine, iodine etc.), a $C_{1-6}$ alkyl group optionally substituted by 1 to 3 halogen atoms (e.g., fluorine, chlorine, bromine, iodine etc.), a $C_{1-6}$ alkoxy group optionally substituted by 1 to 3 halogen atoms (e.g., fluorine, chlorine, bromine, iodine etc.), nitro, hydroxy, amino and the like can be mentioned.

$R^2$ is preferably —$OR^8$ (the symbol is as defined above), and $R^8$ is preferably a hydrogen atom or an alkyl group having 1 to 4 carbon atoms (e.g., methyl, ethyl). $R^2$ is particularly preferably —OH.

As preferable examples of the compound represented by the formula (I), the following compounds can be mentioned.

[Compound A]
A compound wherein
$R^1$ is oxazolyl, thiazolyl, pyrazolyl or triazolyl, each optionally having 1 to 3 substituents selected from
1) an alkyl group having 1 to 10 carbon atoms, which may have 1 to 3 substituents selected from an alkoxy group having 1 to 6 carbon atoms optionally substituted by 1 to 3 halogen atoms, a halogen atom, a nitro, a hydroxy and an amino;
2) a $C_{3-10}$ cycloalkyl group optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro, a hydroxy and an amino;
3) an aryl group having 6 to 14 carbon atoms (preferably, phenyl, naphthyl etc.), which may have 1 to 3 substituents selected from an alkyl group having 1 to 6 carbon atoms optionally substituted by 1 to 3 halogen atoms, an alkoxy group having 1 to 6 carbon atoms optionally substituted by 1 to 3 halogen atoms, a halogen atom, a nitro, a hydroxy and an amino; and
4) an aromatic heterocyclic group (preferably furyl, thienyl, pyridyl, pyrazinyl and the like) optionally having 1 to 3 substituents selected from an alkyl group having 1 to 6 carbon atoms optionally substituted by 1 to 3 halogen atoms, an alkoxy group having 1 to 6 carbon atoms optionally substituted by 1 to 3 halogen atoms, a halogen atom, a nitro, a hydroxy and an amino;

X is a bond or —$NR^5$—, wherein $R^5$ is a hydrogen atom or an alkyl group having 1 to 4 carbon atoms;
Q is $C_{1-6}$ alkylene or $C_{2-6}$ alkenylene;
Y is an oxygen atom or —$NR^6$— wherein $R^6$ is a hydrogen atom or an alkyl group having 1 to 4 carbon atoms;
ring A is a benzene ring, a fused aromatic hydrocarbon ring having 9 to 14 carbon atoms (preferably naphthalene etc.), or a 5- or 6-membered aromatic heterocycle (preferably pyridine, oxazole, isoxazole, thiazole, oxadiazole etc.), each optionally further having 1 to 3 substituents selected from an alkyl group having 1 to 4 carbon atoms, a hydroxy group, an alkoxy group having 1 to 4 carbon atoms, an aralkyloxy group having 7 to 10 carbon atoms and a halogen atom;
Z is —$(CH_2)_n$—$Z^1$— or —$Z^1$—$(CH_2)_n$— wherein n is an integer of 0 to 3, $Z^1$ is a bond, an oxygen atom, a sulfur atom, —$NR^7$—, —$CONR^7$— or —$NR^7CO$— wherein $R^7$ is a hydrogen atom or an alkyl having 1 to 4 carbon atoms;
ring B is an imidazole ring, a pyrazole ring, an oxazole ring, a thiazole ring or a triazole ring, each optionally further having 1 to 3 substituents selected from an alkyl group having 1 to 10 carbon atoms (preferably methyl etc.), an aryl group having 6 to 14 carbon atoms—alkyl group having 1 to 10 carbon atoms (e.g., benzyl etc.) and an optionally partially hydrogenated aryl group having 6 to 14 carbon atoms (preferably phenyl, naphthyl, tetrahydronaphthalenyl etc.);
W is $C_{1-6}$ alkylene; and
$R^2$ is —$OR^8$ wherein $R^8$ is a hydrogen atom or an alkyl group having 1 to 4 carbon atoms.

[Compound B]
A compound wherein
$R^1$ is oxazolyl or triazolyl, each optionally having 1 or 2 substituents selected from an alkyl group having 1 to 3 carbon atoms (preferably methyl), an aryl group having 6 to 14 carbon atoms (preferably phenyl) and an aromatic heterocyclic group (preferably furyl, thienyl);
X is a bond;
Q is $C_{1-6}$ alkylene (preferably —$CH_2$—);
Y is an oxygen atom;
ring A is a benzene ring or a 5- or 6-membered aromatic heterocycle (preferably pyridine, isoxazole), each optionally substituted by an alkoxy group having 1 to 4 carbon atoms (preferably methoxy);
Z is —$(CH_2)_n$—$Z^1$— wherein n is an integer of 0 to 2 (preferably 1), $Z^1$ is a bond, an oxygen atom or a sulfur atom (preferably an oxygen atom);
ring B is a pyrazole ring optionally substituted by an alkyl group having 1 to 10 carbon atoms (preferably methyl), an aryl group having 6 to 14 carbon atoms—alkyl group having 1 to 10 carbon atoms (preferably benzyl) or an aryl group having 6 to 14 carbon atoms (preferably phenyl);
W is $C_{1-6}$ alkylene (preferably —$CH_2$—, —$(CH_2)_2$—); and
$R^2$ is —$OR^8$ wherein $R^8$ is a hydrogen atom or an alkyl group having 1 to 4 carbon atoms (preferably methyl, ethyl).

[Compound C]
[1-methyl-3-[4-(5-methyl-2-phenyl-4-oxazolylmethoxy) benzyloxy]-1H-pyrazol-4-yl]acetic acid,
[1-methyl-3-[6-(5-methyl-2-phenyl-4-oxazolylmethoxy)-3-pyridylmethoxy]-1H-pyrazol-4-yl]acetic acid,
[1-methyl-3-[6-(2-phenyl-4-thiazolylmethoxy)-3-pyridylmethoxy]-1H-pyrazol-4-yl]acetic acid,

[1-benzyl-3-[6-(5-methyl-2-phenyl-4-oxazolylmethoxy)-3-pyridylmethoxy]-1H-pyrazol-4-yl]acetic acid,
[3-[4-(5-methyl-2-phenyl-4-oxazolylmethoxy)benzyloxy]-1-phenyl-1H-pyrazol-4-yl]acetic acid,
[3-[6-(5-methyl-2-phenyl-4-oxazolylmethoxy)-3-pyridylmethoxy]-1-phenyl-1H-pyrazol-4-yl]acetic acid,
3-[3-[3-methoxy-4-(5-methyl-2-phenyl-4-oxazolylmethoxy)benzyloxy]-1-phenyl-1H-pyrazol-5-yl]propionic acid,
3-[3-[4-(5-methyl-2-phenyl-4-oxazolylmethoxy)benzyloxy]-1-phenyl-1H-pyrazol-5-yl]propionic acid, or
3-[3-[3-(5-methyl-2-phenyl-4-oxazolylmethoxy)benzyloxy]-1-phenyl-1H-pyrazol-5-yl]propionic acid.

The salt of a compound of the formula (I) (hereinafter also referred to as Compound (I)) is preferably a pharmacologically acceptable salt, and is exemplified by salts with inorganic bases, salts with organic bases, salts with inorganic acids, salts with organic acids, and salts with basic or acidic amino acids, and the like.

Preferable examples of the salts with inorganic bases include alkali metal salts such as sodium salts and potassium salts; alkaline earth metal salts such as calcium salts and magnesium salts; aluminum salts and ammonium salts; and the like.

Preferable examples of the salts with organic bases include salts with trimethylamine, triethylamine, pyridine, picoline, ethanolamine, diethanolamine, triethanolamine, dicyclohexylamine, N,N-dibenzylethylenediamine and the like.

Preferable examples of the salts with inorganic acids include salts with hydrochloric acid, hydrobromic acid, nitric acid, sulfuric acid, phosphoric acid and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with basic amino acids include salts with arginine, lysine, ornithine and the like.

Preferable examples of the salts with acidic amino acids include salts with aspartic acid, glutamic acid and the like.

Of the aforementioned salts, sodium salts, potassium salts, hydrochlorides and the like are preferable.

A prodrug of Compound (I) refers to a compound capable of being converted to Compound (I) by reactions of an enzyme, gastric juice and the like, under physiological conditions in vivo, i.e., a compound capable of being converted to Compound (I) upon enzymatic oxidation, reduction, hydrolysis and the like, or a compound capable of being converted to Compound (I) upon hydrolysis and the like by gastric juice and the like. Examples of the prodrugs of Compound (I) include compounds derived by acylation, alkylation or phosphorylation of the amino group of Compound (I) (e.g., compounds derived by eicosanoylation, alanylation, pentylaminocarbonylation, (5-methyl-2-oxo-1,3-dioxolen-4-yl)methoxycarbonylation, tetrahydrofuranylation, tetrahydropyranylation, pyrrolidylmethylation, pivaloyloxymethylation or t.-butylation of the amino group of Compound (I)); compounds derived by acylation, alkylation, phosphorylation or boration of the hydroxyl group of Compound (I) (e.g., compounds derived by acetylation, palmitoylation, propanoylation, pivaloylation, succinylation, fumarylation, alanylation, dimethylaminomethylcarbonylation or tetrahydropyranylation of the hydroxyl group of Compound (I)); compounds derived by esterification or amidation of the carboxyl group of Compound (I) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation of the carboxyl group of Compound (I)); etc. These compounds can be produced from Compound (I) by methods known per se.

The prodrug of Compound (I) may be one capable of being converted to Compound (II) under physiological conditions, as described in "Iyakuhin No Kaihatsu (Development of Drugs)", vol. 7, Molecular Designing, published by Hirokawa Shoten, 1990, pages 163–198.

In addition, Compound (I) may be labeled with an isotope (e.g., $^3H$, $^{14}C$, $^{35}S$, $^{125}I$ etc.).

Furthermore, Compound (I) may be anhydrides or hydrates.

Compound (I) and a salt thereof (hereinafter also referred to as "compound of the present invention") have low toxicity and can be used as a prophylactic or therapeutic agent of various diseases mentioned below in mammals (e.g., humans, mice, rats, rabbits, dogs, cats, bovines, horses, swine, monkeys etc.), as such or in the form of pharmaceutical compositions prepared by admixing with a pharmacologically acceptable carrier and the like.

Here, the pharmacologically acceptable carriers are exemplified by various organic or inorganic carrier substances in common use as materials for pharmaceutical preparations, and they are formulated as excipients, lubricants, binders, and disintegrants for solid preparations; solvents, solubilizers, suspending agents, isotonizing agents, buffers, soothing agents for liquid preparations; etc. In addition, other additives for pharmaceutical preparations, such as antiseptics, antioxidants, coloring agents, and sweetening agents, may be also used as necessary.

Preferable examples of the excipients include lactose, saccharose, D-mannitol, D-sorbitol, starch, gelatinized starch, dextrin, crystalline cellulose, low-substituted hydroxypropylcellulose, carboxymethylcellulose sodium, gum arabic, pullulan, light silicic anhydride, synthetic aluminum silicate, magnesium metasilicate aluminate and the like.

Preferable examples of the lubricants include magnesium stearate, calcium stearate, talc, colloidal silica and the like.

Preferable examples of the binders include gelatinized starch, sucrose, gelatin, gum arabic, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like.

Preferable examples of the disintegrants include lactose, saccharose, starch, carboxymethylcellulose, carboxymethylcellulose calcium, croscarmellose sodium, carboxymethyl starch sodium, light silicic anhydride, low-substituted hydroxypropylcellulose and the like.

Preferable examples of the solvents include water for injection, physiological saline, Ringer's solution, alcohol, propylene glycol, polyethylene glycol, sesame oil, corn oil, olive oil, cottonseed oil and the like.

Preferable examples of the solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferable examples of the suspending agents include surfactants such as stearyltriethanolamine, sodium lauryl sulfate, laurylaminopropionic acid, lecithin, benzalkonium chloride, benzethonium chloride, monostearic glycerol etc.; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose etc.; polysorbates, polyoxyethylene-hardened castor oil and the like.

Preferable examples of the isotonizing agents include sodium chloride, glycerol, D-mannitol, D-sorbitol, glucose and the like.

Preferable examples of the buffers include buffer solutions of phosphates, acetates, carbonates, citrates and the like.

Preferable examples of the soothing agents include benzyl alcohol and the like.

Preferable examples of the antiseptics include p-oxybenzoic acid esters, chlorobutanol, benzyl alcohol, phenethyl alcohol, dehydroacetic acid, sorbic acid and the like.

Preferable examples of the antioxidants include sulfites, ascorbates and the like.

Preferable examples of the coloring agents include food colors such as water-soluble tar colors for food (e.g., Food Color Red Nos. 2 and 3, Food Color Yellow Nos. 4 and 5, Food Color Blue Nos. 1 and 2 etc.), water-insoluble lake colors (e.g., aluminum salts of the aforementioned water-soluble tar colors for food etc.), and natural colors (e.g., β-carotene, chlorophyll, red oxide etc.).

Preferable examples of the sweetening agents include saccharin sodium, dipotassium glycyrrhetinate, aspartame, stevia and the like.

Examples of the dosage forms of the pharmaceutical composition include oral preparations such as tablets, capsules (including soft capsules and microcapsules), granules, powders, syrups, emulsions, suspensions etc.; and parenteral preparations such as injections (e.g., subcutaneous injections, intravenous injections, intramuscular injections, intraperitoneal injections etc.), external preparations (e.g., preparations for nasal administration, dermal preparations, ointments etc.), suppositories (e.g., rectal suppositories, vaginal suppositories etc.), pellets, drip infusions, and sustained-release preparations (e.g., sustained-release microcapsules etc.), eye drops and the like. These preparations can each be orally or parenterally administered safely.

The pharmaceutical composition can be prepared by conventional methods in the fields of pharmaceutical manufacturing techniques, such as the methods described in the Japanese Pharmacopoeia. Specific production methods for such preparations are hereinafter described in detail.

An oral preparation, for instance, is produced by adding to the active ingredient, an excipient (e.g., lactose, saccharose, starch, D-mannitol etc.), a disintegrant (e.g., carboxymethylcellulose calcium etc.), a binder (e.g., gelatinized starch, gum arabic, carboxymethylcellulose, hydroxypropylcellulose, polyvinylpyrrolidone etc.) or a lubricant (e.g., talc, magnesium stearate, polyethyleneglycol 6000 etc.), compression molding the obtained mixture, and, if necessary, coating by a method known per se using a coating base for the purpose of taste masking, enteric coating or sustained release.

Examples of the coating base include a sugar coating base, a water-soluble film coating base, an enteric film coating base, a sustained-release film coating base and the like.

As the sugar coating base, saccharose is employed. Further, one or more kinds selected from talc, precipitated calcium carbonate, gelatin, gum arabic, pullulan, carnauba wax and the like may be used in combination.

Examples of the water-soluble film coating base include cellulose polymers such as hydroxypropylcellulose, hydroxypropylmethylcellulose, hydroxyethylcellulose, methylhydroxyethylcellulose; synthetic polymers such as polyvinylacetal diethylaminoacetate, aminoalkyl methacrylate copolymer E [Eudragit E (trademark), Rhom Pharma] and polyvinylpyrrolidone; and polysaccharides such as pullulan.

Examples of the enteric film coating base include cellulose polymers such as hydroxypropylmethylcellulose phthalate, hydroxypropylmethylcellulose acetate succinate, carboxymethylethylcellulose, cellulose acetate phthalate; acrylic acid polymers such as methacrylic acid copolymer L [Eudragit L (trademark), Rhom Pharma], methacrylic acid copolymer LD [Eudragit L-30D55 (trademark), Rhom Pharma], methacrylic acid copolymer S [Eudragit S (trademark), Rhom Pharma]; natural products such as shellac and the like.

Examples of the sustained-release film coating base include cellulose polymers such as ethylcellulose; acrylic acid polymers such as aminoalkyl methacrylate copolymer RS [Eudragit RS (trademark), Rhom Pharma] and an ethyl acrylate-methyl methacrylate copolymer suspension [Eudragit NE (trademark), Rhom Pharma].

Two or more of the above coating bases may be used in admixture in an appropriate ratio. For coating, a shading agent such as titanium oxide, red ferric oxide may be used.

Injections are produced by dissolving, suspending or emulsifying the active ingredient in an aqueous solvent (e.g. distilled water, physiological saline, Ringer's solution etc.) or an oleaginous solvent (e.g. vegetable oils such as olive oil, sesame oil, cotton seed oil, corn oil etc.; propylene glycol etc.), together with a dispersant (e.g. polysorbate 80, polyoxyethylene-hardened castor oil 60 etc.), polyethylene glycol, carboxymethylcellulose, sodium alginate etc.), a preservative (e.g. methylparaben, propylparaben, benzyl alcohol, chlorobutanol, phenol etc.), an isotonizing agent (e.g. sodium chloride, glycerol, D-mannitol, D-sorbitol, glucose etc.) and the like. If desirable, additives such as a solubilizer (e.g. sodium salicylate, sodium acetate etc.), a stabilizer (e.g. human serum albumin etc.), a soothing agent (e.g. benzyl alcohol etc.) and the like, may be used.

The compound of the present invention can be used as an agent for improving insulin resistance, an insulin sensitizer, a retinoid-related receptor function regulating agent, a peroxisome proliferator-activated receptor ligand, a retinoid X receptor ligand and the like. The term "function regulating agent" used here stands for both an agonist and an antagonist.

The compound of the present invention has a hypoglycemic action, a hypolipidemic action, a hypoinsulinemic action, an insulin resistance improving action, an insulin sensitivity enhancing action, and a retinoid-related receptor function regulating action. The function regulating agent may be a partial agonist or a partial antagonist. The term "retinoid-related receptor" used here is classified as a nuclear receptor, and is a DNA-binding transcription factor whose ligand is a signal molecule such as oil-soluble vitamins etc., and may be any of a monomer receptor, a homodimer receptor and a heterodimer receptor.

Here, examples of the monomer receptor include retinoid O receptor (hereinafter also abbreviated as ROR) α (GenBank Accession No. L14611), RORβ (GenBank Accession No.L14160), RORγ (GenBank Accession No. U16997); Rev-erb α (GenBank Accession No. M24898), Rev-erbβ (GenBank Accession No. L31785); ERRα (GenBank Accession No. X51416), ERRβ (GenBank Accession No. X51417); Ftz-FIα (GenBank Accession No. S65876), Ftz-FIβ (GenBank Accession No. M81385); TIx (GenBank Accession No. S77482); GCNF (GenBank Accession No. U14666) and the like.

Examples of the homodimer receptor include homodimers formed by retinoid X receptor (hereinafter also abbreviated as RXR) α (GenBank Accession No. X52733), RXRβ (GenBank Accession No. M84820), RXRγ (GenBank Accession No. U38480); COUPα (GenBank Accession No. X12795), COUPβ (GenBank Accession No. M64497), COUPγ (GenBank Accession No. X12794); TR2α (GenBank Accession No. M29960), TR2β (GenBank Accession No. L27586); or HNF4α (GenBank Accession No. X76930), HNF4γ (GenBank Accession No. Z49826) and the like.

Examples of the heterodimer receptor include heterodimers which are formed by the above-mentioned retinoid X receptor (RXRα, RXRβ or RXRγ) and one receptor selected from retinoid A receptor (hereinafter also abbreviated as RAR) α (GenBank Accession No. X06614, ), RARβ (GenBank Accession No. Y00291), RARγ (GenBank Accession No. M24857); thyroid hormone receptor (hereinafter also abbreviated as TR) α (GenBank Accession No. M24748), TRβ (GenBank Accession No. M26747); vitamin D receptor (VDR) (GenBank Accession No. J03258); peroxisome proliferator-activated receptor (hereinafter also abbreviated as PPAR) α (GenBank Accession No. L02932), PPARβ (PPARδ) (GenBank Accession No. U10375), PPARγ (GenBank Accession No. L40904); LXRα (GenBank Accession No. U22662), LXRβ (GenBank Accession No. U14534); FXR (GenBank Accession No. U18374); MB67 (GenBank Accession No. L29263); ONR (GenBank Accession No. X75163); and NURα (GenBank Accession No. L13740), NURβ (GenBank Accession No. X75918) and NURγ (GenBank Accession No. U12767).

The compound of the present invention has an excellent ligand activity, in particular to retinoid X receptors (RXRα, RXRβ, RXRγ) and to peroxisome proliferator-activated receptors (PPARα, PPARβ (PPARδ), PPARγ), among the above-mentioned retinoid-related receptors, and is useful as an agonist, a partial agonist, an antagonist or a partial antagonist.

Further, the compound of the present invention has an excellent ligand activity to peroxisome proliferator-activated receptors in heterodimer receptors formed from a retinoid X receptor and a peroxisome proliferator-activated receptor (e.g., heterodimer receptors formed from RXRα and PPARδ, heterodimer receptors formed from RXRα and PPARγ etc.).

Accordingly, the retinoid-related receptor ligand of the present invention can be used advantageously as a peroxisome proliferator-activated receptor ligand or a retinoid X receptor ligand.

The compound of the present invention can be used as, for example, a prophylactic or therapeutic agent of diabetes mellitus (e.g., type 1 diabetes mellitus, type 2 diabetes mellitus, gestational diabetes mellitus, etc.); a prophylactic or therapeutic agent of hyperlipidemia (e.g., hypertriglyceridemia, hypercholesterolemia, hypo-high-density-lipoproteinemia, postprandial hyperlipemia etc.); an agent for improving insulin resistance; an insulin sensitizer; a prophylactic or therapeutic agent of impaired glucose tolerance (IGT); and an agent for preventing progress from impaired glucose tolerance to diabetes mellitus.

Regarding diagnostic criteria of diabetes mellitus, new diagnostic criteria were reported by the Japan Diabetes Society in 1999.

According to this report, diabetes mellitus is a condition wherein the fasting blood glucose level (glucose concentration in venous plasma) is not less than 126 mg/dl, the 2-hour value (glucose concentration in venous plasma) of the 75 g oral glucose tolerance test (75 g OGTT) is not less than 200 mg/dl, or the non-fasting blood glucose level (glucose concentration in venous plasma) is not less than 200 mg/dl. In addition, a condition that does not fall within the scope of the above definition of diabetes mellitus, and which is not a "condition wherein the fasting blood glucose level (glucose concentration in venous plasma) is less than 110 mg/dl or the 2-hour value (glucose concentration in venous plasma) of the 75 g oral glucose tolerance test (75 g OGTT) is less than 140 mg/dl" (normal type), is called the "borderline type".

As regards the diagnostic criteria for diabetes mellitus, moreover, new diagnostic criteria were reported by ADA (American Diabetic Association) in 1997 and by WHO in 1998.

According to these reports, diabetes mellitus is a condition where the fasting blood glucose level (glucose concentration in venous plasma) is not less than 126 mg/dl, and the 2-hour value (glucose concentration in venous plasma) of the 75 g oral glucose tolerance test is not less than 200 mg/dl.

In addition, according to the above reports, impaired glucose tolerance is a condition where the fasting blood glucose level (glucose concentration in venous plasma) is less than 126 mg/dl, and the 2-hour value (glucose concentration in venous plasma) of the 75 g oral glucose tolerance test is not less than 140 mg/dl and less than 200 mg/dl. Furthermore, according to the ADA report, a condition where the fasting blood glucose level (glucose concentration in venous plasma) is not less than 110 mg/dl and less than 126 mg/dl, is called IFG (impaired fasting glucose). On the other hand, according to the WHO report, a condition of IFG (impaired fasting glucose) as such, where the 2-hour value (glucose concentration in venous plasma) of the 75 g oral glucose tolerance test is less than 140 mg/dl, is called IFG (impaired fasting glycemia).

The compound of the present invention can also be used as a prophylactic or therapeutic agent of diabetes mellitus, borderline type, impaired glucose tolerance, IFG (impaired fasting glucose) and IFG (impaired fasting glycemia) as defined by the foregoing new diagnostic criteria. Furthermore, the compound of the present invention can be also used to prevent the progression of the borderline type, impaired glucose tolerance, IFG (impaired fasting glucose) or IFG (impaired fasting glycemia) to diabetes mellitus.

The compound of the present invention can be also used as a prophylactic or therapeutic agent of diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, dermal soft tissue infection, lower limb infection etc.), diabetic gangrene, xerostomia, decreased sense of hearing, cerebrovascular disease, peripheral circulatory disturbance etc.), obesity, osteoporosis, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disorder etc.), muscular dystrophy, myocardiac infarction, angina pectoris, cerebrovascular disease (e.g., cerebral infarction, cerebral apoplexy), insulin resistant syndrome, syndrome X, hyperinsulinemia, hyperinsulinemia-induced sensory disorder, tumor (e.g., leukemia, breast cancer, prostate cancer, skin cancer etc.), irritable bowel syndrome, acute or chronic diarrhea, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, pancreatitis, inflammatory colitis, ulcerative colitis), visceral obesity syndrome and the like.

The compound of the present invention possesses a total cholesterol lowering action and enhances a plasma anti-arteriosclerosis index [(HDL cholesterol/total cholesterol)×

100], and therefore, can be used as a prophylactic or therapeutic agent of arteriosclerosis (e.g., atherosclerosis etc.) and the like.

Also, the compound of the present invention can be used for ameliorating bellyache, nausea, vomiting, or dysphoria in epigastrium, each of which is accompanied by gastrointestinal ulcer, acute or chronic gastritis, biliary dyskinesia, cholecystitis and the like.

Furthermore, the compound of the present invention can control (enhance or inhibit) appetite, and therefore, can be used as a therapeutic agent of leanness and cibophobia (the weight increase in administration subjects suffering from leanness or cibophobia) or a therapeutic agent of obesity.

The compound of the present invention can be also used as a prophylactic or therapeutic agent of TNF-α mediated inflammatory diseases. The TNF-α mediated inflammatory diseases mean inflammatory diseases which occur in the presence of TNF-α and can be treated by way of a TNF-α inhibitory action. Examples of such inflammatory diseases include diabetic complications (e.g., retinopathy, nephropathy, neuropathy, macroangiopathy etc.), rheumatoid arthritis, spondylitis deformans, osteoarthritis, lumbago, gout, postoperative or traumatic inflammation, remission of swelling, neuralgia, pharyngolaryngitis, cystitis, hepatitis, pneumonia, gastric mucosal injury (including aspirin-induced gastric mucosal injury) and the like.

The compound of the present invention has an apoptosis inhibitory activity, and can be used as a prophylactic or therapeutic agent of diseases mediated by promotion of apoptosis. Examples of the diseases mediated by promotion of apoptosis include viral diseases (e.g., AIDS, fulminant hepatitis etc.), neurodegenerative diseases (e.g., Alzheimer's disease, Parkinson's disease, amyotropic lateral sclerosis, retinitis pigmentosa, cerebellar degeneration etc.), myelodysplasia (e.g., aplastic anemia etc.), ischemic diseases (e.g., myocardial infarction, cerebral apoplexy etc.), hepatic diseases (e.g., alcoholic hepatitis, hepatitis B, hepatitis C etc.), joint-diseases (e.g., osteoarthritis etc.), atherosclerosis and the like.

The compound of the present invention can be used for reducing visceral fats, inhibiting accumulation of visceral fats, ameliorating glycometabolism, ameliorating lipid metabolism, ameliorating insulin resistance, inhibiting production of oxidized LDL, ameliorating lipoprotein metabolism, ameliorating coronary artery metabolism, preventing or treating cardiovascular complications, preventing or treating heart failure complications, lowering blood remnant, preventing or treating anovulation, preventing or treating hirsutism, preventing or treating hyperandrogenism and the like.

The compound of the present invention can be used for secondary prevention and for inhibition of progress of the various diseases described above (e.g., cardiovascular events such as myocardial infarction etc.).

The compound of the present invention can be used in combination with midazolam, ketoconazole and the like.

Although the dose of the compound of the present invention varies depending on the administration subject, the administration route, the target disease, the clinical condition etc., it is desirable that the compound of the present invention be administered at a usual dosage per administration of about 0.005 to 50 mg/kg body weight, preferably 0.01 to 2 mg/kg body weight, more preferably 0.025 to 0.5 mg/kg body weight, 1 to 3 times a day, for oral administration to an adult diabetic patient, for instance.

The compound of the present invention can be used in combination with a drug such as a therapeutic agent for diabetes mellitus, a therapeutic agent for diabetic complications, an antihyperlipidemic agent, a hypotensive agent, an antiobesity agent, a diuretic agent, a chemotherapeutic agent, an immunotherapeutic agent, etc. (hereinafter, abbreviated as a concomitant drug). The concomitant drug may be a compound having a low molecular weight, or may be a protein, a polypeptide or an antibody, each of which has a high molecular weight, or may be a vaccine and the like. On such occasions, the timing of administration of the compound of the present invention and that of the concomitant drug is not limited. They may be administered simultaneously or in a staggered manners to the administration subject. The dose of the concomitant drug can be appropriately selected based on a clinically employed dose. The proportion of the compound of the present invention and the concomitant drug can be appropriately determined according to the administration subject, the administration route, the target disease, the clinical condition, the combination, and other factors. In cases where the administration subject is a human, for instance, the concomitant drug may be used in an amount of 0.01 to 100 parts by weight per part by weight of the compound of the present invention.

Examples of the therapeutic agent for diabetes mellitus include insulin preparations (e.g., animal insulin preparations extracted from the bovine or swine pancreas; human insulin preparations synthesized by a genetic engineering technique using *Escherichia coli* or a yeast), fragment of insulin or derivatives thereof (e.g., INS-1 etc.), agents for improving insulin resistance (e.g., pioglitazone hydrochloride, troglitazone, rosiglitazone or its maleate, GI-262570, JTT-501, MCC-555, YM-440, KRP-297, CS-011, FK-614 etc.), α-glucosidase inhibitors (e.g., voglibose, acarbose, miglitol, emiglitate etc.), biguanides (e.g., phenformin, metformin, buformin etc.), insulin secretagogues [sulfonylureas (e.g., tolbutamide, glibenclamide, gliclazide, chlorpropamide, tolazamide, acetohexamide, glyclopyramide, glimepiride, glipizide, glybuzole etc.), repaglinide, nateglinide, mitiglinide or its calcium salt hydrate, GLP-1 etc.], dipeptidylpeptidase IV inhibitors (e.g., NVP-DPP-278, PT-100 etc.), β3 agonists (e.g., CL-316243, SR-58611-A, UL-TG-307, SB-226552, AJ-9677, BMS-196085, AZ-40140 etc.), amylin agonists (e.g., pramlintide etc.), phosphotyrosine phosphatase inhibitors (e.g., vanadic acid etc.), gluconeogenesis inhibitors (e.g., glycogen phosphorylase inhibitors, glucose-6-phosphatase inhibitors, glucagon antagonists etc.), SGLT (sodium-glucose cotransporter) inhibitors (e.g., T-1095 etc.) and the like.

Examples of the therapeutic agent for diabetic complications include aldose reductase inhibitors (e.g., tolrestat, epalrestat, zenarestat, zopolrestat, minalrestat, fidarestat (SNK-860), CT-112 etc.), neurotrophic factors (e.g., NGF, NT-3, BDNF etc.), neurotrophic factor production-secretion promoters, PKC inhibitors (e.g., LY-333531 etc.), AGE inhibitors (e.g., ALT946, pimagedine, pyratoxathine, N-phenacylthiazolium bromide (ALT766), EXO-226 etc.), active oxygen scavengers (e.g. thioctic acid etc.), and cerebral vasodilators (e.g., tiapuride, mexiletine).

Examples of the antihyperlipidemic agent include statin compounds which are cholesterol synthesis inhibitors (e.g., cerivastatin, pravastatin, simvastatin, lovastatin, atorvastatin, fluvastatin, itavastatin or their salts (e.g., sodium salt etc.) etc.), squalene synthase inhibitors or fibrate compounds (e.g., bezafibrate, clofibrate, simfibrate, clinofibrate etc.) having a triglyceride lowering action and the like.

Examples of the hypotensive agent include angiotensin converting enzyme inhibitors (e.g., captopril, enalapril, delapril), angiotensin II antagonists (e.g., candesartan cilexetil, losartan, eprosartan, valsartan, termisartan, irbesartan, tasosartan etc.), calcium antagonists (e.g., manidipine, nifedipine, nicardipine, amlodipine, efonidipine), and clonidine.

Examples of the antiobesity agent include antiobesity drugs acting on the central nervous system (e.g. dexfenfluramine, fenfluramine, phentermine, sibutramine, anfepramon, dexamphetamine, mazindol, phenylpropanolamine, clobenzorex etc.), pancreatic lipase inhibitors (e.g. orlistat etc.), β3 agonists (e.g. CL-316243, SR-58611-A, UL-TG-307, SB-226552, AJ-9677, BMS-196085, AZ-40140 etc.), anorectic peptides (e.g. leptin, CNTF (Ciliary Neurotrophic Factor) etc.) and cholecystokinin agonists (e.g. lintitript, FPL-15849 etc.).

Examples of the diuretic agent include xanthine derivatives (e.g., theobromine and sodium salicylate, theobromine and calcium salicylate etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide etc.), chlorobenzenesulfonamide preparations (e.g., chlorthalidone, mefruside, indapamide etc.), azosemide, isosorbide, ethacrynic acid, piretanide, bumetanide, furosemide and the like.

Examples of the chemotherapeutic agent include alkylating agents (e.g., cyclophosphamide, ifosfamide etc.), metabolic antagonists (e.g., methotrexate, 5-fluorouracil and a derivative thereof etc.), antitumor antibiotics (e.g., mitomycin, adriamycin etc.), plant-derived antitumor agents (e.g., vincristine, vindesine, Taxol etc.), cisplatin, carboplatin, etopoxide and the like. Of these, 5-fluorouracil derivatives such as Furtulon and Neo-Furtulon are preferable.

Examples of the immunotherapeutic agent include microorganism- or bacterium-derived components (e.g., muramyl dipeptide derivatives, Picibanil etc.), immunopotentiator polysaccharides (e.g., lentinan, schizophyllan, krestin etc.), genetically engineered cytokines (e.g., interferons, interleukins (IL) etc.), colony stimulating agents (e.g., granulocyte colony stimulating factor, erythropoietin etc.) and the like. Of these, interleukins such as IL-1, IL-2, IL-12 and the like are preferable.

Further, agents whose effects of ameliorating cachexia have been confirmed in animal models or clinically, namely cyclooxygenase inhibitors (e.g., indomethacin etc.) (*Cancer Research*, vol. 49, pp. 5935–5939, 1989), progesterone derivatives (e.g., megestrol acetate) (*Journal of Clinical Oncology*, vol. 12, pp. 213–225, 1994), glucocorticoids (e.g. dexamethasone), metoclopramide pharmaceuticals, tetrahydrocannabinol pharmaceuticals (the above references are applied to both), fat metabolism ameliorating agents (e.g., eicosapentanoic acid etc.) (*British Journal of Cancer*, vol. 68, pp. 314–318, 1993), growth hormones, IGF-1, and antibodies to the cachexia-inducing factor TNF-α, LIF, IL-6 or oncostatin M, can also be used as the concomitant drug.

As the concomitant drug, moreover, neuranagenesis promoters (e.g., Y-128, VX-853, prosaptide etc.), antidepressants (e.g., desipramine, amitriptyline, imipramine, etc.), antiepileptics (e.g., lamotrigine etc.), antiarrhythmic drug (e.g., mexiletine etc.), acetylcholine receptor ligands (e.g., ABT-594 etc.), endothelin receptor antagonists (e.g., ABT-627 etc.), monoamine uptake inhibitor (e.g., tramadol etc.), anesthetic analgesics (e.g., morphine etc.), GABA receptor agonists (e.g., gabapentin etc.), α² receptor agonists (e.g., clonidine etc.), topical analgesics (e.g., capsaicin etc.), protein kinase C inhibitors (e.g., LY-333531 etc.), antianxiety drugs (e.g., benzodiazepine etc.), phosphodiesterase inhibitors (e.g., sildenafil (citrate) etc.), dopamine agonists (e.g., apomorphine etc.), therapeutic agents for osteoporosis (e.g., alfacalcidol, calcitriol, elcatonin, calcitonin salmon, estriol, ipriflavone, pamidronate disodium, alendronate sodium hydrate, incadronate disodium etc.), antidementia agents (e.g., tacrine, donepezil, rivastigmine, galantamine etc.), therapeutic agents for incontinentia or pollakiuria (e.g., flavoxate hydrochloride, oxybutynin hydrochloride, propiverine hydrochloride etc.) and the like can be mentioned.

The concomitant drug is preferably an insulin preparation, an agent for improving insulin resistance, an α-glucosidase inhibitor, a biguanide, an insulin secretagogue (preferably sulfonylurea) and the like.

The above concomitant drugs can be used as a mixture of two or more species in an appropriate ratio. When two or more concomitant drugs are to be used, preferable combinations include the following.

1) an agent for improving insulin resistance and an insulin preparation;
2) an agent for improving insulin resistance and an insulin secretagogue;
3) an agent for improving insulin resistance and an α-glucosidase inhibitor;
4) an agent for improving insulin resistance and a biguanide;
5) an agent for improving insulin resistance, an insulin preparation and a biguanide;
6) an agent for improving insulin resistance, an insulin preparation and an insulin secretagogue;
7) an agent for improving insulin resistance, an insulin preparation and an α-glucosidase inhibitor;
8) an agent for improving insulin resistance, an insulin secretagogue and a biguanide;
9) an agent for improving insulin resistance, an insulin secretagogue and an α-glucosidase inhibitor; and
10) an agent for improving insulin resistance, a biguanide and an α-glucosidase inhibitor.

When the compound of the present invention is used in combination with a concomitant drug, the amount of each agent can be reduced within a safe range by taking their adverse effects into consideration. Particularly, the dose of an agent for improving insulin resistance, an insulin secretagogue and a biguanide can be reduced as compared with the normal dose. Accordingly, an adverse effect which may be caused by these agents can be safely prevented. In addition, the dose of an agent for diabetic complications, an antihyperlipidemic agent and a hypotensive agent can be reduced, whereby an adverse effect which may be caused by these agents can be effectively prevented.

In the following, the production method of the compound of the present invention is explained.

Compound (I) can be produced by a method known per se, such as the following Method A to Method I or a method analogous thereto. In each of the following production methods, the starting compound may be used in the form of a salt, and as such salt, those exemplified as the salt of the aforementioned Compound (I) can be used.

Compound (I-1) of the formula (I) wherein Z is $-(CH_2)_n-Z^{1a}-$ ($Z^{1a}$ is an oxygen atom, a sulfur atom or $-NR^7-$ ($R^7$ is as defined above) and n is as defined above) can be produced by, for example, the following Method A.

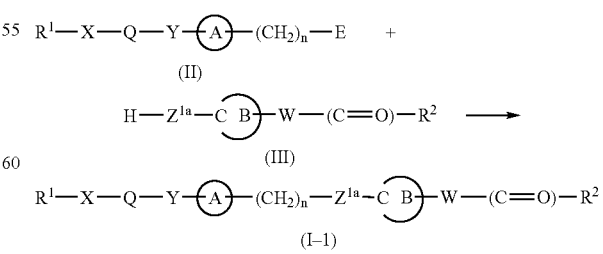

wherein E is a leaving group, and other symbols are as defined above.

As used herein, as the leaving group for E, for example, a hydroxy group, a halogen atom and —OSO$_2$R$^{15}$ wherein R$^{15}$ is an alkyl group having 1 to 4 carbon atoms or an aryl group having 6 to 10 carbon atoms which may be substituted by an alkyl group having 1 to 4 carbon atoms can be mentioned.

The alkyl group having 1 to 4 carbon atoms in the "alkyl group having 1 to 4 carbon atoms" and the "aryl group having 6 to 10 carbon atoms which may be substituted by an alkyl group having 1 to 4 carbon atoms" for R$^{15}$ is exemplified by methyl, ethyl, propyl, isopropyl, butyl, isobutyl, sec.-butyl, and t.-butyl, with preference given to methyl.

The aryl group having 6 to 10 carbon atoms in the "aryl group having 6 to 10 carbon atoms which may be substituted by an alkyl group having 1 to 4 carbon atoms" for R$^{15}$ is exemplified by phenyl and naphthyl, with preference given to phenyl.

R$^{15}$ is particularly preferably methyl, tolyl and the like.

In this method, Compound (I-1) is produced by a reaction of Compound (II) with Compound (III).

When E is a hydroxy group, this reaction is carried out by a method known per se, e.g., the method described in *Synthesis*, page 1 (1981), or a method analogous thereto. Namely, this reaction is normally carried out in the presence of an organic phosphorus compound and an electrophilic agent in a solvent which does not interfere with the reaction.

Examples of the organic phosphorus compound include triphenylphosphine and tributylphosphine.

Examples of the electrophilic agent include diethyl azodicarboxylate, diisopropyl azodicarboxylate and azodicarbonylpiperazine.

The amount of the organic phosphorus compound and electrophilic agent used is preferably about 1 to about 5 molar equivalents relative to Compound (III).

Examples of the solvent which does not interfere with the reaction include ethers such as diethyl ether, tetrahydrofuran, and dioxane; halogenated hydrocarbons such as chloroform and dichloromethane; aromatic hydrocarbons such as benzene, toluene, and xylene; amides such as N,N-dimethylformamide; and sulfoxides such as dimethyl sulfoxide. These solvents may be used in a mixture at appropriate ratios.

The reaction temperature is normally about −50 to about 150° C., preferably about −10 to about 100° C.

The reaction time is normally about 0.5 to about 20 hours.

When E is a halogen atom or —OSO$_2$R$^{15}$, this reaction is carried out by a conventional method in the presence of a base in a solvent which does not interfere with the reaction.

Examples of the base include alkali metal salts such as potassium hydroxide, sodium hydroxide, sodium hydrogen carbonate and potassium carbonate; amines such as pyridine, triethylamine, N,N-dimethylaniline and 1,8-diazobicyclo[5.4.0]undec-7-ene; metal hydrides such as potassium hydride and sodium hydride; and alkali metal alkoxides such as sodium methoxide, sodium ethoxide and potassium t.-butoxide.

The amount of these bases used is preferably about 1 to about 5 molar equivalents relative to Compound (III).

Examples of the solvent which does not interfere with the reaction include aromatic hydrocarbons such as benzene, toluene and xylene; ethers such as tetrahydrofuran, dioxane, and diethyl ether; ketones such as acetone and 2-butanone; halogenated hydrocarbons such as chloroform and dichloromethane; amides such as N,N-dimethylformamide; and sulfoxides such as dimethyl sulfoxide. These solvents may be used in a mixture at appropriate ratios.

The reaction temperature is normally about −50 to about 150° C., preferably about −10 to about 100° C.

The reaction time is normally about 0.5 to about 20 hours.

Compound (I-1) thus obtained may be isolated and purified by known means of separation and purification such as concentration, concentration under reduced pressure, solvent extraction, crystallization, recrystallization, phase transfer and chromatography.

Compound (II) and Compound (III), which are used as the starting compounds in Method A above, are known compounds. Compound (II) wherein E is a hydroxy group is, for example, described in EP-A 710659. In addition, Compound (II) is described in EP-A 629624 (JP-A 7(1995)-53555), WO 98/03505 and the like. Furthermore, Compound (II) can be also produced by methods analogous to those described in these publications.

In addition, Compound (III) is described in, for example, *Tetrahedron*, vol. 43, p. 607 (1987); *Chemical & Pharmaceutical Bulletin*, vol. 12, p. 176 (1964) and the like. The Compound (III) can be also produced by methods analogous to those described in these references.

Compound (I-2) of the formula (I) wherein Z is —Z$^{1a}$—(CH$_2$)$_n$— (wherein the symbols are as defined above) can be produced by, for example, the following Method B.

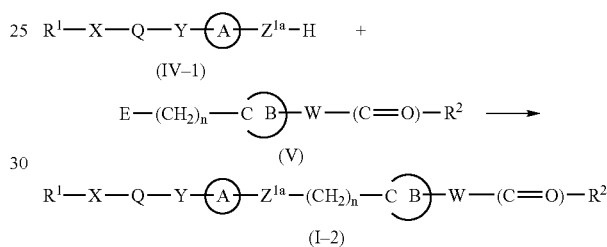

wherein the symbols are as defined above.

In this method, Compound (IV-1) is reacted with Compound (V) to produce Compound (I-2). This reaction is carried out in the same manner as the reaction of Compound (II) with Compound (III) in the aforementioned Method A.

The amount of the organic phosphoric compound and electrophilic agent to be used when E is hydroxyl is preferably about 1 to about 5 molar equivalents relative to Compound (IV-1).

The amount of the base to be used when E is a halogen atom or —OSO$_2$R$^{15}$ is preferably about 1 to about 5 molar equivalents relative to Compound (IV-1).

The Compound (I-2) thus obtained can be isolated and purified by known means of separation and purification such as concentration, concentration under reduced pressure, solvent extraction, crystallization, recrystallization, phase transfer, chromatography and the like.

The Compound (V) to be used as a starting compound in the above-mentioned Method B is a known compound and described in, for example, WO 01/14372 and the like. Moreover, Compound (V) can be also produced by methods analogous to those described in these publications.

The Compound (I-4) of the formula (I) wherein R$^2$ is —OH can be also produced by, for example, the following Method C.

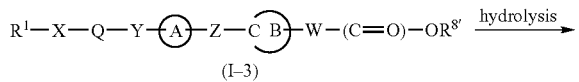

-continued

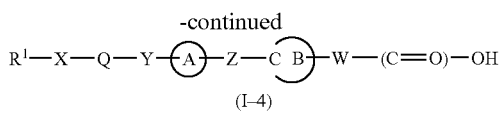

wherein R^8', is an optionally substituted hydrocarbon group and other symbols are as defined above.

In this method, Compound (I-4) is produced by subjecting Compound (I-3) to a hydrolysis reaction.

As used herein, as the "optionally substituted hydrocarbon group" for the above-mentioned $R^{8'}$, those exemplified as the "optionally substituted hydrocarbon group" for $R^8$ can be mentioned, with preference given to "an alkyl group having 1 to 4 carbon atoms" and the like.

As the "alkyl group having 1 to 4 carbon atoms" for the above-mentioned $R^{8'}$, for example, methyl, ethyl, propyl, butyl, isobutyl, sec.-butyl, t.-butyl and the like can be mentioned, with preference given to methyl and ethyl.

This reaction is carried out according to a conventional method in an aqueous solvent in the presence of an acid or a base.

As the acid, for example, inorganic acids such as hydrochloric acid, sulfuric acid, hydrobromic acid and the like; organic acids such as acetic acid and the like; and the like can be mentioned.

Examples of the base include alkali metal carbonates such as potassium carbonate, sodium carbonate and the like; alkali metal alkoxides such as sodium methoxide and the like; and alkali metal hydroxides such as potassium hydroxide, sodium hydroxide, lithium hydroxide and the like, and the like.

The amount of the acid or base used is normally in excess to Compound (I-3). Preferably, the amount of the acid used is about 2 to about 50 equivalents relative to Compound (I-3), and the amount of the base used is about 1.2 to about 5 equivalents relative to Compound (I-3).

Examples of the aqueous solvents include solvent mixtures of water and one or more solvents selected from alcohols such as methanol, ethanol and the like; ethers such as tetrahydrofuran, dioxane, diethyl ether and the like; dimethyl sulfoxide, acetone and the like, and the like.

The reaction temperature is normally about –20 to about –150° C., preferably about –10 to about 100° C.

The reaction time is normally about 0.1 to about 20 hours.

Compound (I-4) thus obtained may be isolated and purified by known means of separation and purification such as concentration, concentration under reduced pressure, solvent extraction, crystallization, recrystallization, phase transfer, chromatography and the like.

Compound (I-3), which is used as the starting compound in Method C above, is produced by, for example, Method A or Method B above.

Compound (I-5) of the formula (I) wherein $R^2$ is —$NR^9R^{10}$ (wherein $R^9$ and $R^{10}$ are as defined above) can be also produced by, for example, the following Method D.

[Method D]

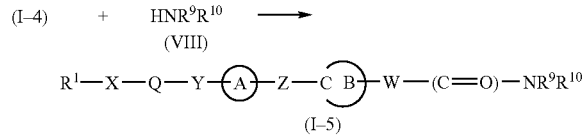

wherein the symbols are as defined above.

In this method, Compound (I-5) is produced by subjecting Compound (I-4) to an amidation reaction. This reaction is carried out by a method known per se, e.g., a method wherein Compound (I-4) and Compound (VIII) are directly condensed by means of a condensing agent (e.g., dicyclohexylcarbodiimide etc.), a method wherein a reactive derivative of Compound (I-4) and Compound (VIII) are reacted as appropriate, or the like. Here, the reactive derivative of Compound (I-4) is exemplified by acid anhydrides, acid halides (e.g., acid chlorides, acid bromides), imidazolides, or mixed acid anhydrides (e.g., anhydrides with methyl carbonate, ethyl carbonate, or isobutyl carbonate etc.) and the like.

When an acid halide is used, for example, the reaction is carried out in the presence of a base in a solvent which does not interfere with the reaction.

Examples of the base include amines such as triethylamine, N-methylmorpholine, N,N-dimethylaniline and the like; alkali metal salts such as sodium hydrogencarbonate, sodium carbonate, potassium carbonate and the like, and the like.

Examples of the solvent which does not interfere with the reaction include halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water and the like. These solvents may be used in a mixture at appropriate ratios.

The amount of Compound (VIII) used is 0.1 to 10 molar equivalents, preferably 0.3 to 3 molar equivalents, relative to Compound (I-4).

The reaction temperature is normally –30 to 100° C.

The reaction time is normally 0.5 to 20 hours.

In addition, when a mixed acid anhydride is used, Compound (I-4) and a chlorocarbonic acid ester (e.g., methyl chlorocarbonate, ethyl chlorocarbonate, isobutyl chlorocarbonate etc.) are reacted in the presence of a base (e.g., amines such as triethylamine, N-methylmorpholine, N,N-dimethylaniline and the like; alkali metal salts such as sodium hydrogencarbonate, sodium carbonate, potassium carbonate and the like, etc.), and are further reacted with Compound (VIII).

The amount of Compound (VIII) used is normally 0.1 to 10 molar equivalents, preferably 0.3 to 3 molar equivalents, relative to Compound (I-4).

The reaction temperature is normally –30° C. to 100° C.

The reaction time is normally 0.5 to 20 hours.

Compound (I-5) thus obtained may be isolated and purified by known means of separation and purification such as concentration, concentration under reduced pressure, solvent extraction, crystallization, recrystallization, phase transfer, chromatography and the like.

Compound (I-4) to be used as a starting compound in the above-mentioned Method D can be produced by, for example, the above-mentioned Methods A to C. As Compound (VIII), a known compound can be used.

Compound (IV-1) to be used as a starting compound in Method B can be produced by, for example, the following Method E.

[Method E]

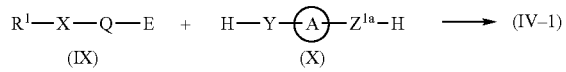

wherein the symbols are as defined above.

This method is carried out in the same manner as the reaction of Compound (II) with Compound (III) in the aforementioned Method A. In this reaction, —$Z^{1a}$—H moiety of Compound (X) may be protected with a suitable protecting group and then condensation reaction may be conducted, after which the resulting compound may be deprotected. As such protecting group, for example, benzyl group, methoxymethyl group, silyl group (e.g., trimethylsilyl group, t.-butyldimethylsilyl group and the like) and the like can be mentioned.

The Compound (IV-1) thus obtained can be isolated and purified by known means of separation and purification such as concentration, concentration under reduced pressure, solvent extraction, crystallization, recrystallization, phase transfer, chromatography and the like.

As Compound (IX) and Compound (X) to be used as starting compounds in the above-mentioned Method E, known compounds can be used.

Compound (I-7) of the formula (I) wherein Z is —$(CH_2)_{n1}$—$S(O)_m$—$(CH_2)_{n2}$— (m is 1 or 2, n1 and n2 are the same or different and each is an integer of 0 to 8 and at least one of n1 and n2 is 0) can be produced by, for example, the following Method F.

[Method F]

$R^1$—X—Q—Y—(A)—$(CH_2)_{n1}$—S—$(CH_2)_{n2}$—C B—W—(C=O)—$R^2$ (I-6)

↓

$R^1$—X—Q—Y—(A)—$(CH_2)_{n1}$—$S(O)_m$—$(CH_2)_{n2}$—C B—W—(C=O)—$R^2$ (I-7)

wherein the symbols are as defined above.

In this method, Compound (I-6) is subjected to oxidization reaction to produce Compound (I-7). This reaction is generally carried out using an oxidant in a solvent that does not adversely influence the reaction.

As the oxidant, for example, 3-chlorophenyl perbenzoate, sodium periodic acid, hydrogen peroxide, peracetic acid and the like can be mentioned.

As the solvent that does not adversely influence the reaction, for example, ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; alcohols such as ethanol, methanol and the like, and the like can be mentioned. These solvents may be used in mixture at appropriately ratios.

The reaction temperature is generally about −50° C. to about 150° C., preferably about −10° C. to about 100° C.

The reaction time is generally about 0.5 to about 20 hrs.

Compound (I-7) thus obtained can be isolated and purified by known means of separation and purification such as concentration, concentration under reduced pressure, solvent extraction crystallization, recrystallization, phase transfer, chromatography and the like.

Compound (I-6) to be used as a starting compound in the above-mentioned Method F can be produced by, for example, the above-mentioned Method A or Method B.

Compound (I-8) of the formula (I) wherein Z is —$(CH_2)_n$— (n is as defined above) can be produced by, for example, the following Method G.

[Method G]

$R^1$—X—Q—Y—(A)—$(CH_2)_n$—COOH + H—T—<(C=O)—V / W—(C=O)—$R^2$ (XI-1)   (XII)

↓ Step 1

$R^1$—X—Q—Y—(A)—$(CH_2)_n$—(C=O)—T—<(C=O)—V / W—(C=O)—$R^2$ (XIII)

↓ Step 2

$R^1$—X—Q—Y—(A)—$(CH_2)_n$—C B—W—(C=O)—$R^2$ (I-8)

wherein T is an oxygen atom, a sulfur atom or —$NR^7$— ($R^7$ is as defined above), V is a hydrogen atom or a substituent, and other symbols are as defined above.

As the substituent for V, those exemplified as the substituent of the aforementioned ring B can be mentioned.

[Step 1]

This method is carried out in the same manner as the reaction of Compound (I-4) with Compound (VIII) in the aforementioned Method D.

Compound (XIII) thus obtained can be isolated and purified by known means of separation and purification such as concentration, concentration under reduced pressure, solvent extraction, crystallization, recrystallization, phase transfer, chromatography and the like.

Compound (XI-1) and Compound (XII) to be used as starting compounds in Step 1 of the above-mentioned Method G are known compounds and Compound (XI-1) is described in, for example, WO 99/585190 and the like. In addition, Compound (XI-1) can be also produced by methods analogous to those described in these publications.

[Step 2]

In this method, Compound (XIII) is subjected to ring closure reaction to give Compound (I-8).

This reaction is carried out according to a conventional method in a solvent that does not adversely influence the reaction in the presence of an ammonium salt.

As the ammonium salt, for example, ammonium acetate and the like can be mentioned.

As the solvent that does not adversely influence the reaction, for example, ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; alcohols such as ethanol, methanol and the like; organic acids such as acetic acid and the like; and the like can be mentioned. These solvents may be used in mixture at appropriate ratios.

The reaction temperature is generally about −50° C. to about 200° C., preferably about −10° C. to about 150° C.

The reaction time is generally about 0.5 to about 20 hrs.

Compound (I-8) thus obtained can be isolated and purified by known means of separation and purification such as concentration, concentration under reduced pressure, solvent extraction, crystallization, recrystallization, phase transfer, chromatography and the like.

Compound (I-9) of the formula (I) wherein Z is —$(CH_2)_{n1}$—$CONR^7$—$(CH_2)_{n2}$— (wherein the symbols are as defined above) can be produced by, for example, the following Method H.

concentration, concentration under reduced pressure, solvent extraction, crystallization, recrystallization, phase transfer, chromatography and the like.

Compound (IV-2) to be used as a starting compound in the above-mentioned Method I can be produced by, for example, the above-mentioned Method E.

Compound (XV) to be used as a starting compound in the above-mentioned Method I can be produced by, for example, the following Method J.

[Method H]

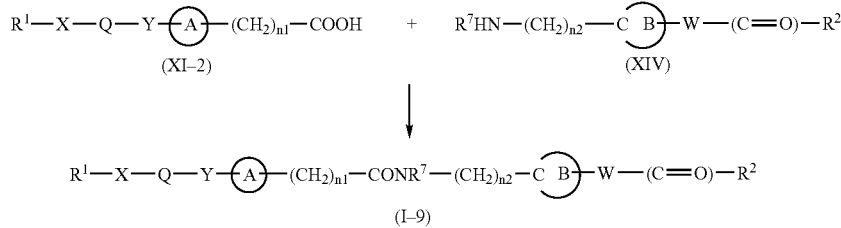

wherein the symbols are as defined above.

This method is carried out in the same manner as in the reaction of Compound (I-4) with Compound (VIII) in the aforementioned Method D.

Compound (I-9) thus obtained can be isolated and purified by known means of separation and purification such as concentration, concentration under reduced pressure, solvent extraction, crystallization, recrystallization, phase transfer, chromatography and the like.

Compound (XI-2) and Compound (XIV) to be used as starting compounds in the above-mentioned Method H are known compounds and described in, for example, WO 99/585190 and the like. Moreover, Compound (XI-2) can be produced by, for example, methods analogous to those described in these publications. In addition, Compound (XIV) is described in, for example, WO 01/14372 and the like. Compound (XIV) can be also produced by methods analogous to those described in these publications.

Compound (I-10) of the formula (I) wherein Z is —$(CH_2)_{n1}$—$NR^7CO$—$(CH_2)_{n2}$— (wherein the symbols are as defined above) can be produced by, for example, the following Method I.

[Method J]

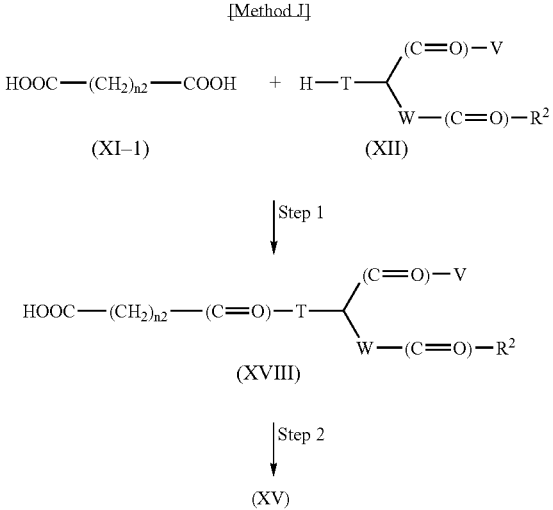

[Method I]

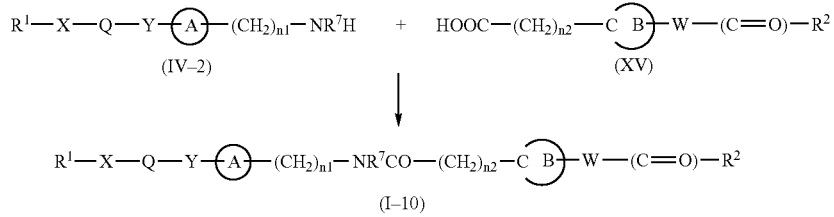

wherein the symbols are as defined above.

This method is performed in the same manner as the reaction of Compound (I-4) with Compound (VIII) in the aforementioned Method D.

Compound (I-10) thus obtained can be isolated and purified by known means of separation and purification such as wherein the symbols are as defined above.

[Step 1]

This method is performed in the same manner as the reaction of Compound (I-4) with Compound (VIII) in the aforementioned Method D.

Compound (XVIII) thus obtained can be isolated and purified by known means of separation and purification such as concentration, concentration under reduced pressure, solvent extraction, crystallization, recrystallization, phase transfer, chromatography and the like.

As Compound (XVI) and Compound (XVII) to be used as starting compounds in the above-mentioned Step 1 of Method J, known compounds can be used.

[Step 2]

This method is carried out in the same manner as Step 2 of Method G.

Compound (XV) thus obtained can be isolated and purified by known means of separation and purification such as concentration, concentration under reduced pressure, solvent extraction, crystallization, recrystallization, phase transfer, chromatography and the like.

When the starting compound has an amino group, a carboxy group, a hydroxy group, or a carbonyl group as a substituent in the respective reactions described above, a protective group in common use in peptide chemistry and other fields may be introduced therein. The desired compound can be obtained by removing the protective group after the reaction, if necessary.

Examples of the protective group for an amino group include those exemplified as the above-mentioned $R^5$.

Examples of the protective group for a carboxy group include $C_{1-6}$ alkyls (e.g., methyl, ethyl, propyl, isopropyl, butyl, t.-butyl etc.), $C_{7-11}$ aralkyls (e.g., benzyl etc.), phenyl, trityl, silyls (e.g., trimethylsilyl, triethylsilyl, dimethylphenylsilyl, t.-butyldimethylsilyl, t.-butyldiethylsilyl etc.), and $C_{2-6}$ alkenyls (e.g., 1-allyl etc.). These groups may be substituted by 1 to 3 halogen atoms (e.g., fluorine, chlorine, bromine, iodine etc.), $C_{1-6}$ alkoxys (e.g., methoxy, ethoxy, propoxy etc.), nitro and the like.

Examples of the protective groups for a hydroxy group include those exemplified as the above-mentioned $R^4$.

Examples of the protective groups for a carbonyl group include cyclic acetals (e.g., 1,3-dioxane etc.) and non-cyclic acetals (e.g., di-$C_{1-6}$ alkylacetals etc.).

In addition, these protective groups can be removed by a method known per se, e.g., the method described in *Protective Groups in Organic Synthesis*, published by John Wiley and Sons (1980). For example, methods employing an acid, a base, ultraviolet rays, hydrazine, phenylhydrazine, sodium N-methyldithiocarbamate, tetrabutylammonium fluoride, palladium acetate, a trialkylsilyl halide (e.g., trimethylsilyl iodide, trimethylsilyl bromide etc.) or the like, the reduction method, and the like may be used.

When Compound (I) contains an optical isomer, a stereomer, a position isomer or a rotation isomer, these isomers are also encompassed as Compound (I) and can be each obtained as a single substance by means of a method known per se of synthesis or separation. For example, when an optical isomer is present in Compound (I), the optical isomer separated from said compound is also included in Compound (I).

Optical isomers can be produced by a method known per se. Specifically, optical isomers are obtained by using an optically active synthesis intermediate, or optically resolving a racemate of the final product by a conventional method.

Examples of the method of optical resolution include methods known per se, such as the fractional recrystallization methods, the chiral column methods and the diastereomer methods.

1) Fractional Recrystallization Method

A method wherein a salt is formed between a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc], which salt is separated by fractional recrystallization etc., and, if desired, subjected to a neutralization process, to yield a free optical isomer.

2) Chiral Column Method

A method wherein a racemate or a salt thereof is applied to a column for optical isomer separation (chiral column). In the case of liquid chromatography, for example, optical isomers are separated by adding a mixture of the optical isomers to a chiral column such as ENANTIO-OVM (produced by Tosoh Corporation) or CHIRAL series produced by DAICEL CHEMICAL IND., and developing it in water, various buffers (e.g., phosphate buffer), an organic solvent (e.g., ethanol, methanol, isopropanol, acetonitrile, trifluoroacetic acid, diethylamine etc.), or a solvent mixture thereof. In the case of gas chromatography, for example, a chiral column such as CP-Chirasil-DeX CB (produced by GL Science) is used to separate optical isomers.

3) Diastereomer Method

A method wherein a racemate mixture and an optically active reagent are chemically reacted to yield a diastereomer mixture, which is then subjected to ordinary means of separation (e.g., fractional recrystallization, chromatography etc.) to obtain single substances, which are subjected to a chemical reaction such as a hydrolysis reaction to cut off the optically active reagent moiety, whereby the desired optical isomer is obtained. For example, when Compound (I) has hydroxy or primary or secondary amino in the molecule thereof, said compound, an optically active organic acid (e.g., MTPA [α-methoxy-α-(trifluoromethyl) phenylacetic acid], (−)-menthoxyacetic acid) and the like may be subjected to a condensing reaction to yield a diastereomer of an ester or amide, respectively. On the other hand, when Compound (I) has a carboxyl group, said compound and an optically active amine or an alcohol reagent may be subjected to a condensing reaction to yield a diastereomer of an amide or ester, respectively. The diastereomer thus separated is converted to an optical isomer of the original compound by subjecting it to an acid hydrolysis or a basic hydrolysis reaction.

BEST MODE FOR CARRYING OUT THE INVENTION

The present invention is hereinafter described in more detail by means of, but is not limited to, the following Test Examples, Reference Examples, Examples and Formulation Examples.

In addition, % in the Reference Examples and Examples below means percent by weight, unless specified otherwise. Room temperature means the temperature of 1 to 30° C.

Abbreviations for bases, amino acids and others used in the present specification are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise indicated.

The sequence numbers in the sequence listing in the present specification show the following respective sequences.

[SEQ ID NO:1]
Shows the base sequence of the primer PARD-U used in Reference Example 1a.

[SEQ ID NO:2]
Shows the base sequence of the primer PARD-L used in Reference Example 1a.

[SEQ ID NO:3]
Shows the base sequence of the primer XRA-U used in Reference Example 2a.

[SEQ ID NO:4]
Shows the base sequence of the primer XRA-L used in Reference Example 2a.

[SEQ ID NO:5]
Shows the base sequence of the PPRE-U used in Reference Example 4a.

[SEQ ID NO:6]
Shows the base sequence of the PPRE-L used in Reference Example 4a.

[SEQ ID NO:7]
Shows the base sequence of the primer TK-U used in Reference Example 4a.

[SEQ ID NO:8]
Shows the base sequence of the primer TK-L used in Reference Example 4a.

[SEQ ID NO:9]
Shows the base sequence of the primer PAG-U used in Reference Example 6a.

[SEQ ID NO:10]
Shows the base sequence of the primer PAG-L used in Reference Example 6a.

TEST EXAMPLE 1

Hypoglycemic and Hypolipidemic (Hypotriglyceridemic) Actions in Mice

Test compounds were mixed in a powdery diet (CE-2, Japan Clea) at the concentration of 0.01%, and freely given to KKA$^y$ mice (11 to 12 weeks old, 5 mice per group), a model of type 2 diabetes mellitus, for four days. During this period, water was given freely. Blood was sampled from orbital venous plexus, and glucose and triglyceride levels in plasma separated from the blood were determined enzymatically using L type Wako Glu2 (Wako Pure Chemical Industries, Ltd.) or L type Wako TG.H (Wako Pure Chemical Industries, Ltd.), respectively. The results are given in Table 1.

In the Table, "hypoglycemic action (%)" represents a percent reduction (%) of the blood glucose level in the treatment group when the blood glucose level in the non-treatment group is taken as 100%. In addition, "hypolipidemic action (%)" represents a percent reduction (%) of the blood triglyceride level in the treatment group when the blood triglyceride level in the non-treatment group is taken as 100%.

TABLE 1

| Test compound (Example No.) | Hypoglycemic action (%) | Hypolipidemic action (%) |
| --- | --- | --- |
| 2 | 45 | 52 |
| 6 | 46 | 62 |

TABLE 1-continued

| Test compound (Example No.) | Hypoglycemic action (%) | Hypolipidemic action (%) |
| --- | --- | --- |
| 8 | 43 | 56 |
| 12 | 52 | 56 |
| 24 | 50 | 22 |
| 26 | 56 | 53 |
| 38 | 47 | 36 |
| 40 | 52 | 76 |
| 44 | 53 | 68 |
| 46 | 54 | 56 |
| 50 | 46 | 81 |
| 52 | 50 | 82 |
| 54 | 52 | 89 |

These results indicate that the compounds of the present invention possess potent hypoglycemic and hypolipidemic actions. Therefore, the compounds of the present invention are useful as prophylactic or therapeutic agents of diabetes mellitus, hyperlipidemia (especially hypertriglyceridemia), impaired glucose tolerance and the like.

TEST EXAMPLE 2

Total Cholesterol Lowering Action and Plasma Anti-Arteriosclerosis Index-Enhancing Action in Mice Test compounds were mixed in a powdery diet (CE-2, Japan Clea) concentration of 0.01%, and freely given to KKA$^y$ mice (11 to 12 weeks old, 5 mice per group), a model of type 2 diabetes mellitus, for four days. During this period, water was given freely. Blood was sampled from orbital venous plexus, and components in plasma separated from the blood were determined. Total cholesterol levels were determined using L type Wako Cholesterol (Wako Pure Chemical Industries, Ltd.). Precipitation reagent for HDL cholesterol was added to a part of the plasma to precipitate non-HDL lipoprotein, and cholesterol (HDL cholesterol) in the resulting supernatant was determined. The plasma anti-arteriosclerosis index [(HDL cholesterol/total cholesterol)× 100] was calculated using these cholesterol levels. The results are given in Table 2.

In the Table, "total cholesterol lowering action (%)" represents a percent reduction (%) of the total cholesterol level in the treatment group when the total cholesterol level in the non-treatment group is taken as 100%. In addition, "plasma anti-arteriosclerosis index-enhancing action (%)" represents a percent increase (%) of the plasma anti-arteriosclerosis index in the treatment group when the plasma anti-arteriosclerosis index in the non-treatment group is taken as 100%.

TABLE 2

| Test compound (Example No.) | Total cholesterol lowering action (%) | Plasma anti-arteriosclerosis index enhancing action (%) |
| --- | --- | --- |
| 6 | 27 | 17 |
| 8 | 17 | 11 |
| 12 | 22 | 15 |
| 26 | 14 | 14 |
| 38 | 12 | 12 |
| 40 | 13 | 22 |
| 50 | 8 | 12 |
| 52 | 22 | 16 |
| 54 | 18 | 14 |

These results indicate that the compounds of the present invention possess total cholesterol lowering and plasma anti-arteriosclerosis index-enhancing actions. Therefore, the compounds are useful as prophylactic or therapeutic agents of arteriosclerosis and the like by improving plasma lipoprotein profiles of hypercholesterolemia and/or hypo-HDL-cholesterolemia.

TEST EXAMPLE 3

PPARδ-RXRα Heterodimer Ligand Activity

PPARδ:RXRα:4ERPP/CHO-K1 cells obtained in Reference Example 5a were cultured in HAM F12 medium (produced by NISSUI SEIYAKU) containing 10% fetal bovine serum (produced by Life Technologies, Inc., USA) and then seeded in a 96-well white plate (produced by Corning Costar Corporation, USA) at the density of $2\times10^4$ cells/well, and cultured in a $CO_2$ gas incubator at 37° C. overnight.

After washing the 96 well white plate with PBS (Phosphate-buffered saline), 90 µl of HAM F12 medium containing 0.1% fatty acid-free bovine serum albumin (BSA) and 10 µl of test compound were added, and the cells were cultured in a $CO_2$ gas incubator at 37° C. for 48 hrs. After removing the medium, 40 µl of PicaGene 7.5 (produced by Wako Pure Chemical Industries, Ltd.) was added. After stirring, the luciferase activity was determined using Lumistar (produced by BMG Labtechnologies GmbH, Germany).

The fold induction was calculated from the luciferase activity of each test compound when the luciferase activity in the non-treatment group is taken as 1. The values of the test compound concentration and the fold induction were analyzed using PRISM 2.01 (produced by GraphPad Software Inc. USA) to calculate the $EC_{50}$ values, the effective concentration of a test compound for 50% of the maximum fold induction. The results are shown in Table 3.

TABLE 3

| test compound (Example No.) | $EC_{50}$ (µM) |
|---|---|
| 10 | 2.1 |
| 12 | 0.67 |

These results indicate that the compounds of the present invention have potent PPAR67-RXRα heterodimer ligand activity.

TEST EXAMPLE 4

(PPARγ-RXRα Heterodimer Ligand Activity)

PPARγ:RXRα:4ERPP/CHO-K1 cells obtained in Reference Example 8a were cultured in HAM F12 medium (manufactured by NISSUI SEIYAKU) containing 10% fetal bovine serum [manufactured by Life Technologies, Inc., USA], seeded in a 96-well white plate [manufactured by Corning Coster Corporation, USA] at the density of $2\times10^4$ cells/well and cultured in a $CO_2$ gas incubator at 37° C. overnight.

After washing the 96-well white plate with PBS (Phosphate-buffered saline), 90 µl of HAM F12 medium containing 0.1% fatty acid-free bovine serum albumin (BSA) and 10 µl of test compound were added, and the cells were cultured in a $CO_2$ gas incubator at 37° C. for 48 hrs. The medium was removed and 40 µl of PicaGene 7.5 (manufactured by Wako Pure Chemical Industries, Ltd.) was added.

After stirring, the luciferase activity was determined using Lumistar [manufactured by BMG Labtechnologies GmbH, Germany].

The fold induction was calculated from the luciferase activity of each test compound when the luciferase activity of the non-treatment group is taken as 1. The values of the test compound concentration and the fold induction were analyzed using PRISM 2.01 (produced by GraphPad Software Inc. USA) to calculate the $EC_{50}$ values, the effective concentration of a test compound for 50% of the maximum fold induction. The results are shown in Table 4.

TABLE 4

| Test compound (Example No.) | $EC_{50}$ (nM) |
|---|---|
| 2 | 3.7 |
| 4 | 16 |
| 6 | 3.6 |
| 8 | 16 |
| 10 | 9.9 |
| 26 | 37 |
| 50 | 3.9 |
| 52 | 0.38 |
| 54 | 0.64 |
| 64 | 6.9 |

These results indicate that the compounds of the present invention have a superior PPARγ-RXRα heterodimer ligand activity.

TEST EXAMPLE 5

PPARδ-RXRα Heterodimer Ligand Activity

The COS-1 cells obtained in Reference Example 9a were recovered, suspended in DMEM medium containing 0.1% fatty acid-free bovine serum albumin (BSA)(manufactured by Wako Pure Chemical Industries, Ltd.) (Nikken Biomedical Laboratory) and seeded in each well of a 96-well white plate (manufactured by Corning Costar Corporation, USA) at the density of $2\times10^4$ cells/well (80 ml). Then, the test Compound (20 ml) was added and the cells were cultured at 37° C., 5% $CO_2$ for 48 hrs. The medium was removed from the 96-well white plate and PicaGine LT7.5 (40 ml, Wako Pure Chemical Industries) was added. After stirring, luciferase activity was measured using 1420 ARVO Multi-label Counter (Wallac)).

The fold induction was calculated from the luciferase activity of the test compound when the luciferase activity of the non-treatment group is taken as 1. The values of the test compound concentration and the fold induction were analyzed using PRISM 2.01 (produced by GraphPad Software Inc. USA) to calculate the $EC_{50}$ values, the effective concentration of a test compound for 50% of the maximum fold induction. The results are shown in Table 5.

TABLE 5

| Test compound (Example No.) | $EC_{50}$ (µM) |
|---|---|
| 58 | 0.68 |
| 60 | 0.26 |

These results indicate-that the compounds of the present invention have a superior PPARδ-RXRα heterodimer ligand activity.

REFERENCE EXAMPLE 1a

Cloning of Human PPARδ Gene

Human PPARδ gene was cloned by PCR using pancreas cDNA (manufactured by Toyobo Co., Ltd., QUICK-Clone cDNA) as a template and a primer set shown below which was prepared by reference to the base sequence of PPARδ gene reported by Schmidt, A. et al. (Mol Endocrinol 1992; 6:1634–1641).

```
PARD-U; 5'-AAC GGT ACC TCA GCC ATG GAG CAG CCT CAG GAG G-3'   (SEQ ID NO: 1)

PARD-L; 5'-TAA GTC GAC CCG TTA GTA CAT GTC CTT GTA GAT C-3'   (SEQ ID NO: 2)
```

The PCR reaction was performed by Hot Start method using AmpliWax PCR Gem 100 (produced by TAKARA SHUZO CO., LTD.). First, 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of human heart cDNA (1 ng/ml) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture prepared as described above, was added one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 45 times, the tube was treated at 72° C. for 8 minutes. The PCR product thus obtained was subjected to electrophoresis on agarose gel (1%), and 1.4 kb DNA fragment containing PPARδ gene was recovered from the gel, and then inserted into pT7 Blue-T vector (produced by TAKARA SHUZO CO., LTD.) to obtain plasmid pTBT-hPPARδ.

REFERENCE EXAMPLE 2a

Cloning of Human RXRα Gene

A human RXRα gene was cloned using a kidney cDNA (produced by Toyobo Co., Ltd., trade name: QUICK-Clone cDNA) as a template by means of a PCR method employing a primer set shown below which was prepared with reference to the base sequence of RXRα gene reported by Mangelsdorf, D. J. et al (*Nature*, 1990, Vol. 345 (6272), page 224–229).

```
XRA-U:
                                              (SEQ ID NO: 3)
5'-TTA GAA TTC GAC ATG GAC ACC AAA CAT TTC CTG-3'

XRA-L:
                                              (SEQ ID NO: 4)
5'-CCC CTC GAG CTA AGT CAT TTG GTG CGG CGC CTC-3'
```

The PCR reaction was performed by Hot Start method using AmpliWax PCR Gem 100 (produced by TAKARA SHUZO CO., LTD.). First, 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of human kidney cDNA (1 ng/ml) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing RXRα gene was recovered from the gel, and then inserted into pT7 Blue-T vector (produced by TAKARA SHUZO CO., LTD.) to obtain plasmid pTBT-hRXRα.

REFERENCE EXAMPLE 3a

Construction of Plasmids for Expressing Human PPARδ, RXRα

A 7.8-kb FspI-NotI fragment of plasmid pVgRXR (produced by Invitrogen, USA) was ligated to a 0.9 kb FspI-NotI fragment containing RXRα gene of plasmid pTBT-hRXRα obtained in Reference Example 2a to prepare plasmid pVgRXR2. Then, pVgRXR2 was digested with BstXI and then treated with T4DNA polymerase (produced by TAKARA SHUZO CO., LTD.) to obtain a blunt terminal. Then digestion at KpnI gave a 6.5 kb DNA fragment. On the other hand, plasmid pTBT-hPPARδ obtained in Reference Example 1a was digested with Sal I and then treated with T4DNA polymerase (produced by TAKARA SHUZO CO., LTD.) to obtain a blunt terminal. Then digestion at KpnI gave a 1.4 kb DNA fragment containing human PPARδ gene.

The both DNA fragments were ligated to construct plasmid pVgRXR2-hPPARδ.

REFERENCE EXAMPLE 4a

Construction of Reporter Plasmids

A DNA fragment containing PPAR-responding element (PPRE) of an acyl CoA oxidase was prepared using the following 5'-terminal phosphorylated synthetic DNA.

```
PPRE-U:
                                              (SEQ ID NO: 5)
5'-pTCGACAGGGGACCAGGACAAAGGTCACGTTCGGGAG-3'

PPRE-L:
                                              (SEQ ID NO: 6)
5'-pTCGACTCCCGAACGTGACCTTTGTCCTGGTCCCCTG-3'
```

First, PPRE-U and PPRE-L were annealed and inserted to Sal I site of plasmid pBlue Script SK+. By determining the base sequence of the inserted fragment, plasmid pBSS-PPRE4, in which 4 PPREs were ligated in tandem, was selected.

An HSV thymidine kinase minimum promoter (TK promoter) region was cloned using pRL-TK vector (produced by Promega, USA) as a template by means of a PCR method employing a primer set shown below which was prepared with reference to the base sequence of the promoter region of thymidine kinase reported by Luckow, B et al (*Nucleic Acids Res.*, 1987, Vol.15(13), p.5490)

```
TK-U:
5'-CCCAGATCTCCCCAGCGTCTTGTCATTG-3'  (SEQ ID NO: 7)

TK-L:
5'-TCACCATGGTCAAGCTTTTAAGCGGGTC-3'  (SEQ ID NO: 8)
```

The PCR reaction was performed by Hot Start method using AmpliWax PCR Gem 100 (TAKARA SHUZO CO., LTD.). First, 2 µl of 10×LA PCR Buffer, 3 µl of 2.5 mM dNTP solution, 2.5 µl each of 12.5 µM primer solutions and 10 µl of sterilized distilled water were mixed to obtain a bottom layer solution mixture. 1 µl of pRL-TK vector (produced by Promega, USA) as a template, 3 µl of 10×LA PCR Buffer, 1 µl of 2.5 mM dNTP solution, 0.5 µl of TaKaRa LA Taq DNA polymerase (produced by TAKARA SHUZO CO., LTD.) and 24.5 µl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 140 b DNA fragment containing TK promoter was recovered from the gel, and then inserted into pT7 Blue-T vector (produced by TAKARA SHUZO CO., LTD.). By digesting the plasmid thus obtained with the restriction enzymes Bgl II and NcoI, a fragment containing TK promoter was obtained, which was ligated to the Bgl II-NcoI fragment of plasmid pGL3-Basic vector (produced by Promega, USA) to obtain plasmid pGL3-TK.

A 4.9 kb NheI-XhoI fragment of plasmid pGL3-TK thus obtained was ligated to a 200 b NheI-XhoI fragment of plasmid pBSS-PPRE4 to obtain plasmid pGL3-4ERPP-TK.

This plasmid pGL3-4ERPP-TK thus obtained was digested with BamHI (produced by TAKARA SHUZO CO., LTD.) and then treated with T4DNA polymerase (produced by TAKARA SHUZO CO., LTD.) to form a blunt terminal, whereby obtaining a DNA fragment.

On the other hand, pGFP-C1 (produced by Toyobo Co., Ltd.) was digested with Bsu36I (NEB) and then treated with T4DNA polymerase (produced by TAKARA SHUZO CO., LTD.) to form a blunt terminal whereby obtaining a 1.6 kb of a DNA fragment.

The both DNA fragments were ligated to construct a reporter plasmid pGL3-4ERPP-TK neo.

REFERENCE EXAMPLE 5a

Introduction of Human PPARδ- and RXRα-Expression Plasmid and Reporter Plasmid into CHO-K1 Cell and Establishment of Expressed Cell After a CHO-K1 cell cultured in a tissue culture flask (750 ml) (produced by Corning Costar Corporation, USA) containing HAM F12 medium (produced by NISSUI SEIYAKU) supplemented with 10% fetal bovine serum (produced by Life Technologies, Oriental, Inc.) was scraped by treating with 0.5 g/L trypsin-0.2 g/L EDTA (produced by Life Technologies Oriental, Inc.), the cell was washed with PBS (produced by Life Technologies, Inc., USA), centrifuged (1000 rpm, 5 minutes), and then suspended in PBS. Subsequently, a DNA was introduced into the cell under the conditions shown below using GENE PULSER (produced by Bio-Rad Laboratories, USA).

Namely, to a cuvette having a 0.4 cm gap, added were $8 \times 10^6$ cells and 10 µg of plasmid pVgRXR2-hPPARδ obtained in Reference Example 3a and 10 µg of reporter plasmid pGL3-4ERPP-TK neo obtained in Reference Example 4a, which was subjected to electroporation at the voltage of 0.25 kV under the capacitance of 960 mF. Subsequently, the cell was transferred into a HAM F12 medium containing 10% fetal bovine serum and cultured for 24 hours and then the cell was scraped again and centrifuged, and then suspended in HAM F12 medium containing 10% fetal bovine serum supplemented with 500 µg/ml of GENETICIN (produced by Life Technologies Oriental, Inc.) and 250 µg /ml of ZEOCIN (produced by Invitrogen, USA). The obtained suspension was diluted to the density of $10^4$ cells/ml and inoculated to a 96-well plate (Becton Dickinson), which was cultured in a $CO_2$ gas incubator at 37° C., whereby obtaining a GENETICIN- and ZEOCIN-resistant transformant.

Subsequently, after the transformant cell line thus obtained was cultured in a 24-well plate (produced by Corning Costar Corporation, USA), selected was a cell line in which the luciferase was expressed and induced, i.e., PPARδ:RXRα:4ERPP/CHO-K1 cell by the addition of 10 mM Iloprost.

REFERENCE EXAMPLE 6a

Cloning of Human PPARγ Gene

A human PPARγ gene was cloned using a heart cDNA (produced by Toyobo Co., Ltd., trade name: QUICK-Clone cDNA) as a template by means of a PCR method employing a primer set shown below which was prepared with reference to the base sequence of PPARγ gene reported by Greene et al (*Gene Expr.*, 1995, Vol. 4 (4–5), pages 281–299).

```
PAG-U:
                                    (SEQ ID NO: 9)
5'-GTG GGT ACC GAA ATG ACC ATG GTT GAC ACA GAG-3'

PAG-L:
                                    (SEQ ID NO: 10)
5'-GGG GTC GAC CAG GAC TCT CTG CTA GTA CAA GTC-3'
```

The PCR reaction was performed by Hot Start method using Ampliwax PCR Gem 100 (produced by TAKARA SHUZO CO., LTD.). First, 2 µl of 10×LA PCR Buffer, 3 µl of 2.5 mM dNTP solution, 2.5 µl each of 12.5 µM primer solutions and 10 µl of sterilized distilled water were mixed to obtain a bottom layer solution mixture. 1 μl of human heart cDNA (1 ng/ml) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing PPARγ gene was recovered from the gel, and then inserted into pT7 Blue-T vector (produced by TAKARA SHUZO CO., LTD.) to obtain plasmid pTBT-hPPARγ.

REFERENCE EXAMPLE 7a

Construction of Plasmids for Expressing Human PPARγ, RXRα

A 7.8 kb FspI-NotI fragment of plasmid pVgRXR (produced by Invitrogen, USA) was ligated to a 0.9 kb FspI-NotI fragment containing RXRα gene of plasmid pTBT-hRXRα obtained in Reference Example 2a to prepare plasmid pVgRXR2. Then, pVgRXR2 was digested with BstXI and then treated with T4DNA polymerase (produced by TAKARA SHUZO CO., LTD.) to obtain a blunt terminal. Then digestion at KpnI gave a 6.5 kb DNA fragment.

On the other hand, plasmid pTBT-hPPARγ obtained in Reference Example 6a was digested with Sal I and then treated with T4DNA polymerase (produced by TAKARA SHUZO CO., LTD.) to obtain a blunt terminal. Then digestion at KpnI gave a 1.4 kb DNA fragment containing human PPARγ gene.

The both DNA fragments were ligated to construct plasmid pVgRXR2-hPPARγ.

REFERENCE EXAMPLE 8a

Introduction of Human PPARγ- and RXRα-Expression Plasmid and Reporter Plasmid into CHO-K1 Cell and Establishment of Expressed Cell After a CHO-K1 cell cultured in a tissue culture flask (750 ml) (produced by Corning Costar Corporation, USA) containing HAM F12 medium (produced by NISSUI SEIYAKU) supplemented with 10% fetal bovine serum (produced by Life Technologies, Inc., USA) was scraped by treating with 0.5 g/L trypsin-0.2 g/L EDTA (ethylenediaminetetraacetic acid) (produced by Life Technologies, Inc., USA), the cell was washed with PBS (phosphate-buffered saline) (produced by Life Technologies, Inc., USA), centrifuged (1000 rpm, 5 minutes), and then suspended in PBS. Subsequently, a DNA was introduced into the cell under the conditions shown below using GENE PULSER (produced by Bio-Rad Laboratories, USA).

Namely, to a cuvette having a 0.4 cm gap, added were $8 \times 10^6$ cells and 10 μg of plasmid pVgRXR2-hPPARγ obtained in Reference Example 7a and 10 μg of reporter plasmid pGL3-4ERPP-TK neo obtained in Reference Example 4a, which was subjected to electroporation at the voltage of 0.25 kV under the capacitance of 960 μF. Subsequently, the cell was transferred into a HAM F12 medium containing 10% fetal bovine serum and cultured for 24 hours and then the cell was scraped again and centrifuged, and then suspended in HAM F12 medium containing 10% fetal bovine serum supplemented with 500 μg/ml of GENETICIN, (produced by Life Technologies, Inc., USA) and 250 μg/ml of ZEOCIN (produced by Invitrogen, USA). The obtained suspension was diluted to the density of $10^4$ cells/ml and inoculated to a 96-well plate (produced by Corning Costar Corporation, USA), which was cultured in a $CO_2$ gas incubator at 37° C., whereby obtaining a GENETICIN- and ZEOCIN-resistant transformant.

Subsequently, after the transformant cell line thus obtained was cultured in a 24-well plate (produced by Corning Costar Corporation, USA), selected was a cell line in which the luciferase was expressed and induced, i.e., PPARγ:RXRα:4ERPP/CHO-K1 cell by the addition of 10 μM pioglitazone hydrochloride.

REFERENCE EXAMPLE 9a

Introduction of Plasmid and Reporter Plasmid for Expression of Human PPARδ, RXRα into COS-1 Cell COS-1 cells were seeded in a tissue culture flask 150 cm² (manufactured by Corning Costar Corporation, USA) at the density of $5 \times 10^6$ cells and cultured at 37° C. under 5% $CO_2$ conditions for 24 hrs. The cells were transfected using lipofect amine (Life Technologies, Inc.). The transfection mixture was prepared by mixing 125 ml of lipofect amine, 100 ml of PLUS Reagent, 2.5 mg of pMCMVneo-hPPARd, 2.5 mg of pMCMVneo-hRXRa, 5 mg of reporter plasmid pGL3-PPREx4-tk-luc-neo and 5 mg of pRL-CMV [manufactured by Promega, USA] with 5 ml of opti-MEM (Life Technologies, Inc.). The above-mentioned transfection mixture and 20 ml of opti-MEM were added to COS-1 cells washed with opti-MEM and the cells were cultured at 37° C., under 5% $CO_2$ conditions for 3 hrs. Then, 25 ml of DMEM medium (Nikken Biomedical Laboratories) containing 0.1% fatty acid-free bovine serum albumin (BSA)(Wako Pure Chemical Industries) was added, and the cells were cultured at 37° C., under 5% $CO_2$ conditions for 24 hrs.

REFERENCE EXAMPLE 1

To a solution of methyl 5-oxo-5-phenylpentanoate (16.1 g) in diethyl ether (100 ml) was added bromine (4.01 ml) at room temperature over 30 min. and the mixture was stirred for 30 min. An aqueous sodium sulfite solution was added to the reaction mixture and the mixture was extracted with diethyl ether. The diethyl ether layer was washed with saturated brine, dried ($MgSO_4$) and concentrated to give methyl 4-bromo-5-oxo-5-phenylpentanoate (22.1 g, yield 100%) as a pale-yellow oil.

NMR($CDCl_3$) δ: 2.30–2.67 (4H, m), 3.70 (3H, s), 5.38 (1H, dd, J=5.6, 8.2 Hz), 7.44–7.54 (2H, m), 7.56–7.66 (1H, m), 8.00–8.06 (2H, m).

REFERENCE EXAMPLE 2

A mixture of methyl 4-bromo-5-oxo-5-phenyl pentanoate (5.00 g), sodium formate (5.96 g) and methanol (100 ml) was refluxed for 24 hrs. The reaction solvent was removed under reduced pressure and the residue was dissolved in ethyl acetate. The obtained ethyl acetate solution was washed with water and then saturated brine, dried (MgSO$_4$) and concentrated. The residue was subjected to silica gel column chromatography and methyl 4-hydroxy-5-oxo-5-phenylpentanoate (2.97 g, yield 76%) was obtained as a colorless oil from a fraction eluted with ethyl acetate-hexane (1:3, volume ratio).

NMR(CDCl$_3$) δ: 1.56–1.75 (1H, m), 2.22–2.55 (2H, m), 2.63–2.81 (1H, m), 3.68–3.72 (4H, m), 5.11–5.21 (1H, m), 7.48–7.69 (3H, m), 8.01–8.08 (2H, m).

REFERENCE EXAMPLE 3

A mixture of methyl 4-bromo-5-oxo-5-phenylpentanoate (1.00 g), diformylimide sodium salt (400 mg) and acetonitrile (5 ml) was stirred at 80° C. for 10 hrs. and the reaction mixture was poured into water and the mixture was extracted with ethyl acetate. The ethyl acetate layer was washed with saturated brine, dried (MgSO$_4$) and concentrated. The residue was subjected to silica gel column chromatography, and methyl 4-diformylimide-5-oxo-5-phenylpentanoate (485 mg, yield 50%) was obtained as a colorless oil from a fraction eluted with ethyl acetate-hexane (2:3, volume ratio).

NMR(CDCl$_3$) δ: 2.10–2.40 (1H, m), 2.44 (2H, t, J=6.8 Hz), 2.55–2.73 (1H, m), 3.71 (3H, s), 5.70–5.85 (1H, m), 7.39–7.49 (2H, m), 7.51–7.62 (1H, m), 7.75–7.82 (2H, m), 8.86 (2H, br s).

REFERENCE EXAMPLE 4

A mixture of methyl 4-diformylimide-5-oxo-5-phenylpentanoate (415 mg) and a solution of 10% hydrochloric acid in methanol (5 ml) was stirred at room temperature for 15 hrs. The reaction mixture was concentrated under reduced pressure and the obtained colorless crystal was recrystallized from diethyl ether-methanol to give methyl 4-amino-5-oxo-5-phenylpentanoate hydrochloride (323 mg, yield 84%). melting point: 165–167° C.

REFERENCE EXAMPLE 5

A mixture of [4-(5-methyl-2-phenyl-4-oxazolylmethoxy) phenyl]acetic acid (1.00 g), methyl 4-hydroxy-5-oxo-5-phenylpentanoate (687 mg), 1-ethyl-3-(dimethylaminopropyl) carbodiimide hydrochloride (water-soluble carbodiimide; hereinafter to be referred to as WSC) (711 mg), 4-(N,N-dimethylamino)pyridine (75.5 mg) and N,N-dimethylformamide (10 ml) was stirred at room temperature for 18 hrs, and the reaction mixture was poured into 1N hydrochloric acid and the mixture was extracted with ethyl acetate. The ethyl acetate layer was washed with saturated brine, dried (MgSO$_4$) and concentrated. The residue was subjected to silica gel column chromatography, and methyl 4-[4-(5-methyl-2-phenyl-4-oxazolylmethoxy)phenyl]acetoxy-5-oxo-5-phenylpentanoate (1.44 g, yield 88%) was obtained as a colorless oil from a fraction eluted with ethyl acetate-hexane (1:2, volume ratio).

NMR(CDCl$_3$) δ: 1.85–2.15 (1H, m), 2.20–2.52 (6H, m), 3.68 (5H, s like), 4.98 (2H, s), 5.92–5.99 (1H, m), 6.97 (2H, d, J=8.8 Hz), 7.22 (2H, d, J=8.8 Hz), 7.38–7.50 (5H, m), 7.53–7.63 (1H, m), 7.95–8.04 (4H, m).

REFERENCE EXAMPLE 6

A mixture of methyl 4-amino-5-oxo-5-phenylpentanoate hydrochloride (1.60 g), triethylamine (0.868 ml) and N,N-dimethylformamide (15 ml) was stirred at room temperature for 5 min and [4-(5-methyl-2-phenyl-4-oxazolylmethoxy) phenyl]acetic acid (2.50 g), WSC (1.42 g) and 1-hydroxy-1H-benzotriazole hydrate (hereinafter to be referred to as HOBt) (1.14 g) were added to the reaction mixture, and the mixture was stirred at said temperature for 18 hrs. The reaction mixture was poured into dilute hydrochloric acid and the mixture was extracted with ethyl acetate. The ethyl acetate layer was washed with saturated aqueous sodium hydrogen carbonate and then saturated brine, dried (MgSO$_4$) and concentrated. The residue was subjected to silica gel column chromatography, and methyl 4-[4-(5-methyl-2-phenyl-4-oxazolylmethoxy) phenyl] acetamide-5-oxo-5-phenylpentanoate (2.67 g, yield 82%) was obtained as a pale-yellow oil from a fraction eluted with ethyl acetate-hexane (2:1, volume ratio).

NMR(CDCl$_3$) δ: 1.60–1.80 (1H, m), 2.21–2.42 (3H, m), 2.45 (3H, s), 3.58 (2H, s), 3.67 (3H, s), 5.00 (2H, s), 5.62–5.73 (1H, m), 6.47 (1H, br d, J=7.8 Hz), 7.02 (2H, d, J=8.8 Hz), 7.22 (2H, d, J=8.8 Hz), 7.39–7.66 (6H, m), 7.99–8.07 (4H, m).

REFERENCE EXAMPLE 7

To a solution of ethyl-3-ethoxy-5-(5-methyl-2-phenyl-4-oxazolylmethoxy)benzoate (5.40 g) in tetrahydrofuran (80 ml) was gradually added aluminum lithium hydride (540 mg) at 0° C. and the mixture was stirred for 1 hr. Sodium sulfate 10 hydrate (4.60 g) was added to the reaction mixture and the mixture was further stirred for 30 min. The insoluble materials were filtered off, and the filtrate was concentrated. The obtained crystals were recrystallized from ethyl acetate-isopropyl ether to give 3-ethoxy-5-(5-methyl-2-phenyl-4-oxazolylmethoxy)benzyl alcohol (4.44 g, 92%) as colorless needle-shaped crystals. melting point: 103–104° C.

REFERENCE EXAMPLE 8

To a solution of 3-ethoxy-5-(5-methyl-2-phenyl-4-oxazolylmethoxy)benzyl alcohol (4.38 g) in toluene (80 ml) was added dropwise thionyl chloride (1.69 g) at room temperature. After stirring for 90 min, ethyl acetate (100 ml) was added to the reaction mixture and the mixture was washed with aqueous sodium bicarbonate and then with water. The organic layer was dried (MgSO$_4$) and concentrated. The residue was subjected to silica gel column chromatography, and the crystals obtained from the fraction eluted with ethyl acetate-hexane (1:4, volume ratio) were recrystallized from ethyl acetate-hexane to give 4-(3-chloromethyl-5-ethoxyphenoxymethyl)-5-methyl-2-phenyloxazole (4.25 g, 92%) as colorless prism crystals. melting point: 86–87° C.

REFERENCE EXAMPLE 9

A mixture of 4-chloromethyl-2-(2-furyl)-5-methyloxazole (10.0 g), 4-hydroxyphenylmethyl acetate (8.41 g), potassium carbonate (14.0 g) and N,N-dimethylformamide (50 ml) was stirred at 70° C. for 1 hr. The reaction mixture was poured into water and the mixture was extracted with ethyl acetate. The ethyl acetate layer was washed with saturated brine, dried (MgSO$_4$) and concentrated. The residue was subjected to silica gel column chromatography, and methyl [4-[2-(2-furyl)-5-methyl-4-oxazolylmethoxy]phenyl]acetate (9.23 g, yield 56%) was obtained as a colorless oil from a fraction eluted with ethyl acetate-hexane (2:3, volume ratio).

NMR(CDCl$_3$) δ: 2.41 (3H, s), 3.57 (2H, s), 3.69 (3H, s), 4.97 (2H, s), 6.50–6.54 (1H, m), 6.93–6.99 (3H, m), 7.20 (2H, d, J=8.8 Hz), 7.52–7.55 (1H, m).

REFERENCE EXAMPLE 10

A mixture of methyl [4-[2-(2-furyl)-5-methyl-4-oxazolylmethoxy]phenyl] acetate (9.15 g), lithium hydroxide hydrate (3.52 g), tetrahydrofuran (60 ml), water (40 ml) and methanol (20 ml) was stirred at room temperature for 2 hrs. 1N Hydrochloric acid (85 ml) was added to the reaction mixture and the mixture was extracted with ethyl acetate. The ethyl acetate layer was washed with saturated brine, dried (MgSO$_4$) and concentrated to give [4-[2-(2-furyl)-5-methyl-4-oxazolylmethoxy]phenyl]acetic acid (7.88 g, yield 90%) as colorless crystals. The crystals were recrystallized from ethyl acetate-hexane. melting point: 139–140° C.

REFERENCE EXAMPLE 11

A mixture of methyl 4-amino-5-oxo-5-phenylpentanoate hydrochloride (822 mg), triethylamine (0.447 ml) and N,N-dimethylformamide (10 ml) was stirred at room temperature for 5 min, and [4-[2-(2-furyl)-5-methyl-4-oxazolylmethoxy]phenyl]acetic acid (1.00 g), WSC (734 mg) and HOBt (586 mg) were added to the reaction mixture. The mixture was stirred at said temperature for 18 hrs. The reaction mixture was poured into dilute hydrochloric acid and the mixture was extracted with ethyl acetate. The ethyl acetate layer was washed with saturated aqueous sodium hydrogen carbonate and then saturated brine, dried (MgSO$_4$) and concentrated. The residue was subjected to silica gel column chromatography, and methyl 4-[4-[2-(2-furyl)-5-methyl-4-oxazolylmethoxy]phenyl]acetamide-5-oxo-5-phenylpentanoate (1.21 g; yield 73%) was obtained as colorless crystals from a fraction eluted with ethyl acetate-hexane (3:2, volume ratio) and recrystallized from ethyl acetate-hexane. melting point: 108–110° C.

REFERENCE EXAMPLE 12

A mixture of methyl [4-[2-(2-furyl)-5-methyl-4-oxazolylmethoxy]phenyl]acetate (1.00 g), methyl 4-hydroxy-5-oxo-5-phenylpentanoate (709 mg), WSC (734 mg), 4-(N,N-dimethylamino)pyridine (77.9 mg) and N,N-dimethylformamide (10 ml) was stirred at room temperature for 6 hrs. The reaction mixture was poured into 1N hydrochloric acid and the mixture was extracted with ethyl acetate. The ethyl acetate layer was washed with saturated brine, dried (MgSO$_4$) and concentrated. The residue was subjected to silica gel column chromatography, and methyl 4-[4-[2-(2-furyl)-5-methyl-4-oxazolylmethoxy]phenyl]acetoxy-5-oxo-5-phenylpentanoate (1.56 g, yield %) was obtained as a pale-yellow oil from a fraction eluted with ethyl acetate-hexane (2:3, volume ratio).

NMR(CDCl$_3$) δ: 1.90–2.52 (7H, m), 3.68 (5H, s like), 4.97 (2H, s), 5.92–5.99 (1H, m), 6.50–6.54 (1H, m), 6.92–6.99 (3H, m), 7.21 (2H, d, J=8.8 Hz), 7.40–7.62 (4H, m), 7.95–8.00 (2H, m).

REFERENCE EXAMPLE 13

A mixture of ethyl 3-hydroxy-1-methyl-1H-pyrazole-4-carboxylate (25.50 g), benzyl bromide (17.8 ml), potassium carbonate (31.10 g) and N,N-dimethylformamide (250 ml) was stirred overnight at 50° C. The reaction mixture was poured into water and the mixture was extracted with ethyl acetate. The ethyl acetate layer was dilute hydrochloric acid, washed with saturated brine, dried (MgSO$_4$) and concentrated. The residue was subjected to silica gel column chromatography, and ethyl 3-benzyloxy-1-methyl-1H-pyrazole-4-carboxylate (31.90 g, yield 82%) was obtained as a colorless crystal from a fraction eluted with ethyl acetate-hexane (1:1, volume ratio) and recrystallized from ethyl acetate-hexane. melting point: 66–67° C.

REFERENCE EXAMPLE 14

To a solution of ethyl 3-benzyloxy-1-methyl-1H-pyrazole-4-carboxylate (18.00 g) in tetrahydrofuran (200 ml) was added aluminum lithium hydride (2.62 g) at 0° C. and the mixture was stirred at room temperature for 1 hr. To the reaction mixture was added sodium sulfate 10 hydrate (22.20 g) and the mixture was stirred at room temperature for 1 hr. The precipitate was removed by filtration and the filtrate was concentrated. The residue was subjected to silica gel column chromatography, and (3-benzyloxy-1-methyl-1H-pyrazol-4-yl)methanol (23.90 g, yield 91%) was obtained as a colorless oil from a fraction eluted with ethyl acetate.

NMR(CDCl$_3$) δ: 1.74 (1H, t, J=5.4 Hz), 3.72 (3H, s), 4.47 (2H, d, J=5.4 Hz), 5.24 (2H, s), 7.17 (1H, s), 7.28–7.47 (5H, m).

REFERENCE EXAMPLE 15

A mixture of (3-benzyloxy-1-methyl-1H-pyrazol-4-yl)methanol (18.40 g), active manganese dioxide (40.00 g) and tetrahydrofuran (200 ml) was stirred at room temperature for 9 hrs. Manganese dioxide was filtered off and the filtrate was concentrated. The residue was subjected to silica gel column chromatography, and 3-benzyloxy-1-methyl-1H-pyrazole-4-carbaldehyde (14.80 g, yield 81%) was obtained as a colorless oil from a fraction eluted with ethyl acetate-hexane (2:1, volume ratio).

NMR(CDCl$_3$) δ: 3.78 (3H, s), 5.32 (2H, s), 7.29–7.50 (5H, m), 7.69 (1H, s), 9.76 (1H, s).

REFERENCE EXAMPLE 16

To a mixture of potassium t-butoxide (2.24 g) and dimethoxyethane (10 ml) was added a solution of p-toluenesulfonylmethyl isocyanide (2.05 g) in dimethoxyethane (10 ml) and the mixture was stirred at −78° C. for 5 min. Then a solution of 3-benzyloxy-1-methyl-1H-pyrazole-4-carbaldehyde (2.16 g) in dimethoxyethane (10 ml) was added. After stirring at said temperature for 1 hr, the mixture was stirred for 1 hr. while raising the temperature to room temperature. To the obtained mixture was added methanol (380 ml), and the mixture was refluxed for 1 hr. After cooling, the reaction solution was poured into saturated aqueous ammonium chloride solution and the mixture was extracted with ethyl acetate. The ethyl acetate layer was washed with saturated brine, dried (MgSO$_4$) and concentrated. The residue was subjected to silica gel column chromatography, and 3-benzyloxy-1-methyl-1H-pyrazol-4-ylacetonitrile (1.86 g, yield 82%) was obtained as a colorless oil from a fraction eluted with ethyl acetate-hexane (1:2, volume ratio).

NMR(CDCl$_3$) δ: 3.43 (2H, s), 3.74 (3H, s), 5.22 (2H, s), 7.21 (1H, s), 7.29–7.47 (5H, m).

REFERENCE EXAMPLE 17

A mixture of 3-benzyloxy-1-methyl-1H-pyrazol-4-ylacetonitrile (12.0 g), 4N aqueous sodium hydroxide solution (100 ml), tetrahydrofuran (100 ml) and ethanol (100 ml) was refluxed for 21 hrs. After cooling, the mixture was neutralized with dilute hydrochloric acid and extracted with ethyl acetate. The ethyl acetate layer was washed with saturated brine, dried (MgSO$_4$) and concentrated. A mixture of the residue, methyl iodide (4.95 ml), potassium carbonate (14.7 g) and N,N-dimethylformamide (100 ml) was stirred overnight at room temperature. The reaction solution was poured into water, and the mixture was extracted with ethyl acetate. The ethyl acetate layer was washed with saturated brine, dried (MgSO$_4$) and concentrated. The residue was subjected to silica gel column chromatography, and methyl 3-benzyloxy-1-methyl-1H-pyrazol-4-ylacetate (12.2 g, yield 88%) was obtained as a yellow oil from a fraction eluted with ethyl acetate-hexane (1:1, volume ratio).

NMR(CDCl$_3$) δ: 3.41 (2H, s), 3.68 (3H, s), 3.73 (3H, s), 5.22 (2H, s), 7.19 (1H, s), 7.30–7.46 (5H, m).

REFERENCE EXAMPLE 18

A mixture of methyl 3-benzyloxy-1-methyl-1H-pyrazol-4-ylacetate (12.2 g), 5% palladium-carbon (25.0 g), tetrahydrofuran (100 ml) and ethanol (100 ml) was stirred under hydrogen atmosphere for 5 hrs. Palladium-carbon was filtered off and the filtrate was concentrated to give methyl 3-hydroxy-1-methyl-1H-pyrazol-4-ylacetate (6.33 g, yield 79%) as colorless crystals. The crystals were recrystallized from tetrahydrofuran-hexane. melting point: 118–119° C.

REFERENCE EXAMPLE 19

To a solution of 2-(5-methyl-2-phenyl-4-oxazolylmethoxy)pyridine-5-carbaldehyde (13.0 g) in tetrahydrofuran (150 ml)-methanol (10 ml) was gradually added sodium borohydride (835 mg) at 0° C. After stirring for 30 min., water was added to the reaction mixture and the mixture was extracted with ethyl acetate. The organic layer was washed with water, dried over anhydrous magnesium sulfate and concentrated to give 2-(5-methyl-2-phenyl-4-oxazolylmethoxy)pyridine-5-methanol as crystals. The crystals were recrystallized from acetone-isopropyl ether to give colorless prism crystals (12.4 g, yield 95%). melting point: 121–122° C.

REFERENCE EXAMPLE 20

To a mixture of 2-(5-methyl-2-phenyl-4-oxazolylmethoxy)pyridine-5-methanol (12.2 g)land toluene (200 ml) was added thionyl chloride (5.39 g) and the mixture was stirred at room temperature for 1 hr. Ice water was added to the reaction mixture and the mixture was neutralized with saturated aqueous sodium hydrogen carbonate and extracted with ethyl acetate. The organic layer was washed with water, dried over anhydrous magnesium sulfate and concentrated. The residue was subjected to silica gel column chromatography, and 5-chloromethyl-2-(5-methyl-2-phenyl-4-oxazolylmethoxy)pyridine (11.7 g, yield 90%) was obtained as a colorless crystals from a fraction eluted with ethyl acetate-hexane (1:3, volume ratio). The crystals were recrystallized from ethyl acetate-hexane to give colorless prism crystals. melting point: 86–87° C.

REFERENCE EXAMPLE 21

To a solution of 5-methyl-2-phenyl-4-oxazolylmethanol (9.46 g) in N,N-dimethylformamide (50 ml) was added, sodium hydride (60% in oil, 2.40 g) at 0° C. and the mixture was stirred for 15 min. Then a solution (50 ml) of methyl 2-chloro-4-pyridinecarboxylate (8.58 g) in tetrahydrofuran was added. After stirring at room temperature for 1 hr., the reaction mixture was poured into water and the mixture was extracted with ethyl acetate. The ethyl acetate layer was washed with saturated brine, dried (MgSO$_4$) and concentrated. The residue was subjected to silica gel column chromatography, and methyl 2-(5-methyl-2-phenyl-4-oxazolylmethoxy)-4-pyridinecarboxylate (2190 mg, yield 14%) was obtained as colorless crystals from a fraction eluted with ethyl acetate-hexane (1:3, volume ratio). The crystals were recrystallized from ethyl acetate-hexane. melting point: 106–107° C.

REFERENCE EXAMPLE 22

To a solution of methyl 2-(5-methyl-2-phenyl-4-oxazolylmethoxy)-4-pyridinecarboxylate (1.95 g) in tetrahydrofuran (20 ml) was added aluminum lithium hydride (228 mg) at 0° C. and the mixture was stirred at room temperature for 30 min. Sodium sulfate 10 hydrate (1.93 g) was added to the reaction mixture and the mixture was stirred at room temperature for 30 min. The precipitate was filtered off and the filtrate was concentrated. The obtained colorless crystals were collected by filtration to give 2-(5-methyl-2-phenyl-4-oxazolylmethoxy)-4-pyridylmethanol (1.37 g, yield 77%). The crystals were recrystallized from ethyl acetate-hexane. melting point: 100–101° C.

REFERENCE EXAMPLE 23

A mixture of 2-(5-methyl-2-phenyl-4-oxazolylmethoxy)-4-pyridylmethanol (1.19 g) and thionyl chloride (4 ml) was stirred at room temperature for 1 hr. The reaction mixture was concentrated and saturated aqueous sodium hydrogen carbonate was added. The mixture was extracted with ethyl acetate. The ethyl acetate layer was washed with saturated brine, dried (MgSO$_4$) and concentrated. The residue was subjected to silica gel column chromatography, and 4-chloromethyl-2-(5-methyl-2-phenyl-4-oxazolylmethoxy)pyridine (680 mg, yield 54%) was obtained as colorless crystals from a fraction eluted with ethyl acetate-hexane (1:3, volume ratio). The crystals were recrystallized from ethyl acetate-hexane. melting point: 104–105° C.

REFERENCE EXAMPLE 24

To a solution of methyl 3-hydroxyisoxazole-5-carboxylate (5.01 g) in N,N-dimethylformamide (70 ml) was added sodium hydride (60% in oil, 1.40 g) at 0° C. and the mixture was stirred for 15 min. Then 4-chloromethyl-5-methyl-2-phenyloxazole (7.26 g) was added and the mixture was stirred at 60° C. for 2 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and methyl 3-(5-methyl-2-phenyl-4-oxazolylmethoxy)-5-isoxazolecarboxylate (7.96 g, yield 72%) was obtained as colorless crystals from a fraction eluted with tetrahydrofuran-hexane (1:1, volume ratio). The crystals were recrystallized from tetrahydrofuran-hexane. melting point: 123–124° C.

REFERENCE EXAMPLE 25

To a solution of methyl 3-(5-methyl-2-phenyl-4-oxazolylmethoxy)-5-isoxazolecarboxylate (7.86 g) in tetrahydrofuran (150 ml) was slowly added diisobutylaluminum hydride (1.0 M tetrahydrofuran solution, 60 ml) at 0° C. and the mixture was stirred at room temperature for 30 min. The reaction mixture was poured into dilute hydrochloric acid and the mixture was extracted with ethyl acetate. The ethyl acetate layer was washed with saturated brine, dried ($MgSO_4$) and concentrated to give 3-(5-methyl-2-phenyl-4-oxazolylmethoxy)-5-isoxazolylmethanol (5.93 g, yield 86%) as colorless crystals. The crystals were recrystallized from ethyl acetate-hexane. melting point: 99–100° C.

REFERENCE EXAMPLE 26

To a solution of 3-(5-methyl-2-phenyl-4-oxazolylmethoxy)-5-isoxazolylmethanol (2.86 g) in toluene (50 ml) was slowly added thionyl chloride (0.80 ml) at room temperature and the mixture was stirred under reflux for 30 min. After cooling, the reaction mixture was poured into saturated aqueous sodium hydrogen carbonate and the mixture was extracted with ethyl acetate. The ethyl acetate layer was washed with saturated brine, dried ($MgSO_4$) and concentrated to give 5-chloromethyl-3-(5-methyl-2-phenyl-4-oxazolylmethoxy)isoxazole (2.70 g, yield 89%) as colorless crystals. The crystals were recrystallized from ethyl acetate-hexane. melting point: 105–106° C.

REFERENCE EXAMPLE 27

A mixture of methyl 3-hydroxyisoxazole-5-carboxylate (5.01 g), 2-chloromethylquinoline hydrochloride (8.99 g), potassium carbonate (14.50 g) and N,N-dimethylformamide (100 ml) was stirred at 60° C. for 2 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and methyl 3-(2-quinolylmethoxy)-5-isoxazolecarboxylate (7.78 g, yield 78%) was obtained as colorless crystals from a fraction eluted with tetrahydrofuran. The crystals were recrystallized from tetrahydrofuran-hexane. melting point: 133–134° C.

REFERENCE EXAMPLE 28

To a solution of methyl 3-(2-quinolylmethoxy)-5-isoxazolecarboxylate (7.39 g) in tetrahydrofuran (150 ml) was slowly added diisobutylaluminum hydride (1.0 M tetrahydrofuran solution, 60 ml) at 0° C. and the mixture was stirred at room temperature for 30 min. The reaction mixture was poured into dilute hydrochloric acid and the mixture was extracted with ethyl acetate. The ethyl acetate layer was washed with saturated brine, dried ($MgSO_4$) and concentrated to give 3-(2-quinolylmethoxy)-5-isoxazolylmethanol (4.95 g, yield 74%) as colorless crystals. The crystals were recrystallized from tetrahydrofuran-hexane. melting point: 111–112° C.

REFERENCE EXAMPLE 29

A mixture of 3-(2-quinolylmethoxy)-5-isoxazolylmethanol (1.54 g) and thionyl chloride (5 ml) was stirred at room temperature for 1 hr. The reaction mixture was concentrated under reduced pressure and saturated aqueous sodium hydrogen carbonate was added to the residue. The mixture was extracted with ethyl acetate. The ethyl acetate layer was washed with saturated brine, dried ($MgSO_4$) and concentrated to give 2-(5-chloromethyl-3-isoxazolyloxymethyl)quinoline (1.61 g, yield 98%) as colorless crystals. The crystals were recrystallized from ethyl acetate-hexane. melting point: 126–127° C.

REFERENCE EXAMPLE 30

To a solution of 2-phenyl-4-thiazolylmethanol (6.69 g) and methyl 6-chloro-3-pyridinecarboxylate (6.01 g) in N,N-dimethylformamide (100 ml) was added sodium hydride (60% in oil, 1.40 g) at 0° C. and the mixture was stirred for 30 min. The reaction mixture was poured into water and the mixture was extracted with ethyl acetate. The ethyl acetate layer was washed with saturated brine, dried ($MgSO_4$) and concentrated. To a solution of the residue in tetrahydrofuran (150 ml) was added aluminum lithium hydride (1.33 g) at 0° C. and the mixture was stirred at room temperature for 10 min. Sodium sulfate 10 hydrate (11.3 g) was added to the reaction mixture and the mixture was stirred at room temperature for 30 min. The precipitate was filtered off and the filtrate was concentrated. The residue was subjected to silica gel column chromatography, and 2-(2-phenyl-4-thiazolylmethoxy)-5-pyridylmethanol (5.81 g, yield 56%) was obtained as colorless crystals from a fraction eluted with tetrahydrofuran. The crystals were recrystallized from tetrahydrofuran-hexane. melting point: 134–135° C.

REFERENCE EXAMPLE 31

A mixture of 2-(2-phenyl-4-thiazolylmethoxy)-5-pyridylmethanol (2.98 g) and thionyl chloride (15 ml) was stirred at room temperature for 1 hr. The reaction mixture was concentrated under reduced pressure and saturated aqueous sodium hydrogen carbonate was added to the residue. The mixture was extracted with ethyl acetate. The ethyl acetate layer was washed with saturated brine, dried ($MgSO_4$) and concentrated. The residue was subjected to silica gel column chromatography, and 5-chloromethyl-2-(2-phenyl-4-thiazolylmethoxy)pyridine (2.40 g, yield 76%) was obtained as colorless crystals from a fraction eluted with ethyl acetate. The crystals were recrystallized from tetrahydrofuran-hexane. melting point: 117–118° C.

REFERENCE EXAMPLE 32

To a mixture of 6-(5-methyl-2-phenyl-4-thiazolylmethoxy)nicotinealdehyde (4.20 g), tetrahydrofuran (50 ml) and ethanol (50 ml) was added sodium borohydride (0.51 g) at room temperature, and the mixture was stirred at room temperature for 30 min. Water was added to the reaction mixture and the mixture was extracted with ethyl acetate. The organic layer was washed with saturated brine, dried over anhydrous magnesium sulfate and concentrated to give 6-(5-methyl-2-phenyl-4-thiazolylmethoxy)-3-pyridylmethanol as colorless crystals (4.10 g, yield 97%). The crystals were recrystallized from ethyl acetate-hexane. melting point: 70–71° C.

REFERENCE EXAMPLE 33

A mixture of 6-(5-methyl-2-phenyl-4-thiazolylmethoxy)-3-pyridylmethanol (1.56 g) and thionyl chloride (10 ml) was stirred at room temperature for 1 hr. The mixture was concentrated under reduced pressure and ice water was added to the residue. The mixture was neutralized with saturated aqueous sodium hydrogen carbonate and extracted with ethyl acetate. The organic layer was washed with water, dried over anhydrous magnesium sulfate and concentrated. The residue was subjected to silica gel column chromatography, and 5-chloromethyl-2-(5-methyl-2-phenyl-4-thiazolylmethoxy)pyridine (1.53 g, yield 92%) was obtained as colorless crystals from a fraction eluted with ethyl acetate-hexane (1:2, volume ratio). The crystals were recrystallized from ethyl acetate-hexane. melting point: 78–79° C.

REFERENCE EXAMPLE 34

To a mixture of 6-[2-(2-furyl)-5-methyl-4-oxazolylmethoxy]nicotinealdehyde (3.10 g), tetrahydrofuran (50 ml) and ethanol (50 ml) was added sodium borohydride (0.41 g) at room temperature, and the mixture was stirred at room temperature for 30 min. Water was added to the reaction mixture and the mixture was extracted with ethyl acetate. The organic layer was washed with saturated brine, dried over anhydrous magnesium sulfate and concentrated to give 6-[2-(2-furyl)-5-methyl-4-oxazolylmethoxy]-3-pyridylmethanol as colorless crystals (2.86 g, yield 92%). The crystals were recrystallized from ethyl acetate-hexane. melting point: 120–121° C.

REFERENCE EXAMPLE 35

A mixture of 6-[2-(2-furyl)-5-methyl-4-oxazolylmethoxy]-3-pyridylmethanol (1.87 g) and thionyl chloride (15 ml) was stirred at room temperature for 1 hr. After concentration under reduced pressure, ice water was added to the residue. The mixture was neutralized with saturated aqueous sodium hydrogen carbonate and extracted with ethyl acetate. The organic layer was washed with water, dried over anhydrous magnesium sulfate and concentrated. The residue was subjected to silica gel column chromatography, and 5-chloromethyl-2-[2-(2-furyl)-5-methyl-4-oxazolylmethoxy]pyridine (1.41 g, yield 71%) was obtained as colorless crystals from a fraction eluted with ethyl acetate-hexane (1:3, volume ratio). The crystals were recrystallized from ethyl acetate-hexane. melting point: 95–96° C.

REFERENCE EXAMPLE 36

A mixture of ethyl 3-hydroxy-1H-pyrazole-4-carboxylate (11.53 g), benzyl bromide (18 ml), potassium carbonate (21.12 g) and N,N-dimethylformamide (300 ml) was stirred at 80° C. for 5 hrs. The reaction mixture was poured into water and the mixture was extracted with ethyl acetate. The ethyl acetate layer was dilute hydrochloric acid, then washed successively with saturated brine, dried (MgSO$_4$) and concentrated. The residue was subjected to silica gel column chromatography, and ethyl 1-benzyl-3-benzyloxy-1H-pyrazole-4-carboxylate (13.52 g, yield 95%) was obtained as colorless crystals from a fraction eluted with ethyl acetate-hexane (1:4, volume ratio). The crystals were recrystallized from ethyl acetate-hexane. melting point: 71–72° C.

REFERENCE EXAMPLE 37

To a solution of ethyl 1-benzyl-3-benzyloxy-1H-pyrazole-4-carboxylate (58.90 g) in tetrahydrofuran (500 ml) was added aluminum lithium hydride (6.64 g) at 0° C. and the mixture was stirred at room temperature for 30 min. Water was added to the reaction mixture and the precipitate was filtered off. The filtrate was extracted with ethyl acetate. The ethyl acetate layer was washed with saturated brine, dried (MgSO$_4$) and concentrated. The residue was subjected to silica gel column chromatography, and (1-benzyl-3-benzyloxy-1H-pyrazol-4-yl)methanol (45.30 g, yield 88%) was obtained as colorless crystals from a fraction eluted with ethyl acetate. The crystals were recrystallized from ethyl acetate-hexane. melting point: 79–80° C.

REFERENCE EXAMPLE 38

A mixture of (1-benzyl-3-benzyloxy-1H-pyrazol-4-yl)methanol (14.70 g), active manganese dioxide (30.00 g) and tetrahydrofuran (200 ml) was stirred at room temperature for 2 hrs. Manganese dioxide was filtered off and the filtrate was concentrated. The obtained crystals were collected by filtration to give 1-benzyl-3-benzyloxy-1H-pyrazole-4-carbaldehyde (13.10 g, yield 90%). The crystals were recrystallized from tetrahydrofuran-hexane. melting point: 85–86° C.

REFERENCE EXAMPLE 39

To a mixture of t-butoxy potassium (11.2 g) and dimethoxyethane (50 ml) was added a solution of p-toluenesulfonylmethyl isocyanide (10.3 g) in dimethoxyethane (50 ml) at −78° C. and the mixture was stirred for 5 min. Then a solution of 1-benzyl-3-benzyloxy-1H-pyrazole-4-carbaldehyde (14.6 g) in dimethoxyethane (50 ml) was added. After stirring at said temperature for 1 hr, the mixture was stirred for 1 hr. while raising the temperature to room temperature. To the obtained mixture was added methanol (150 ml), and the mixture was refluxed for 1 hr. After cooling, the reaction solution was poured into saturated aqueous ammonium chloride solution and the mixture was extracted with ethyl acetate. The ethyl acetate layer was washed with saturated brine, dried (MgSO$_4$) and concentrated. The residue was subjected to silica gel column chromatography, and 1-benzyl-3-benzyloxy-1H-pyrazol-4-ylacetonitrile (13.1 g, yield 86%) was obtained as a colorless oil from a fraction eluted with ethyl acetate-hexane (1:3, volume ratio).

NMR(CDCl$_3$) δ: 3.42 (2H, s), 5.11 (2H, s), 5.24 (2H, s), 7.18–7.24 (3H, m), 7.27–7.47 (8H, m).

REFERENCE EXAMPLE 40

A mixture of 1-benzyl-3-benzyloxy-1H-pyrazol-4-ylacetonitrile (13.0 g), 4N aqueous sodium hydroxide solution (100 ml), tetrahydrofuran (100 ml) and ethanol (100 ml) was refluxed for 3 days. After cooling, the mixture was neutralized with dilute hydrochloric acid and extracted with ethyl acetate. The ethyl acetate layer was washed with saturated brine, dried (MgSO$_4$) and concentrated. A mixture of the residue, ethyl iodide (5.2 ml), potassium carbonate (11.9 g) and N,N-dimethylformamide (100 ml) was stirred at room temperature for 3 hrs. The reaction solution was poured into water, and the mixture was extracted with ethyl acetate. The ethyl acetate layer was washed with saturated brine, dried (MgSO$_4$) and concentrated. The residue was subjected to silica gel column chromatography, and ethyl 1-benzyl-3-benzyloxy-1H-pyrazol-4-ylacetate (14.9 g, yield 99%) was obtained as a colorless oil from a fraction eluted with ethyl acetate-hexane (1:2, volume ratio).

NMR(CDCl$_3$) δ: 1.22 (3H, t, J=7.2 Hz), 3.39 (2H, s), 4.12 (2H, q, J=7.2 Hz), 5.12 (2H, s), 5.24 (2H, s), 7.17–7.26 (3H, m), 7.28–7.49 (8H, m).

REFERENCE EXAMPLE 41

A mixture of ethyl 1-benzyl-3-benzyloxy-1H-pyrazol-4-ylacetate (14.9 g), 5% palladium-carbon (15.0 g), tetrahydrofuran (150 ml) and ethanol (150 ml) was stirred under a hydrogen atmosphere for 2 hrs. Palladium-carbon was filtered off and the filtrate was concentrated to give 1-benzyl-3-hydroxy-1H-pyrazol-4-ylethyl acetate (9.76 g, yield 88%) as colorless crystals. The crystals were recrystallized from tetrahydrofuran-hexane. melting point: 156–157° C.

REFERENCE EXAMPLE 42

A mixture of ethyl 3-hydroxy-1-phenyl-1H-pyrazole-4-carboxylate (7.76 g), benzyl bromide (3.97 ml), potassium carbonate (6.91 g) and N,N-dimethylformamide (75 ml) was stirred overnight at 50° C. The reaction mixture was poured into water and the mixture was extracted with ethyl acetate. The ethyl acetate layer was dilute hydrochloric acid, and then washed successively with saturated brine, dried (MgSO$_4$) and concentrated. The residue was subjected to silica gel column chromatography, and ethyl 3-benzyloxy-1-phenyl-1H-pyrazole-4-carboxylate (8.29 g, yield 77%) was obtained as colorless crystals from a fraction eluted with ethyl acetate-hexane (1:1, volume ratio). The crystals were recrystallized from ethyl acetate-hexane. melting point: 113–114° C.

REFERENCE EXAMPLE 43

To a solution of ethyl 3-benzyloxy-1-phenyl-1H-pyrazole-4-carboxylate (8.06 g) in tetrahydrofuran (100 ml) was added aluminum lithium hydride (0.95 g) at 0° C. and the mixture was stirred at room temperature for 1 hr. Sodium sulfate 10 hydrate (8.06 g) was added to the reaction mixture and the mixture was stirred at room temperature for 1 hr. The precipitate was filtered off and the filtrate was concentrated. The residue was subjected to silica gel column chromatography, and (3-benzyloxy-1-phenyl-1H-pyrazol-4-yl)methanol (5.91 g, yield 84%) was obtained as colorless crystals from a fraction eluted with ethyl acetate. The crystals were recrystallized from ethyl acetate-hexane. melting point: 93–94° C.

REFERENCE EXAMPLE 44

To a mixture of 1-benzyl-3-benzyloxy-1H-pyrazole-4-carbaldehyde (12.90 g), diethylphosphonoethyl acetate (9.60 ml) and N,N-dimethylformamide (200 ml) was added hydride (60% in oil, 1.94 g) at 0° C., and the mixture was stirred at room temperature for 2 hrs. The reaction mixture was poured into water and the mixture was extracted with ethyl acetate. The ethyl acetate layer was dilute hydrochloric acid, washed successively with saturated brine, dried (MgSO$_4$) and concentrated. The obtained crystals were collected by filtration to give ethyl (E)-3-(1-benzyl-3-benzyloxy-1H-pyrazol-4-yl)propenoate (14.50 g, yield 91%). The crystals were recrystallized from ethyl acetate-hexane. melting point: 88–89° C.

REFERENCE EXAMPLE 45

A mixture of ethyl (E)-3-(1-benzyl-3-benzyloxy-1H-pyrazol-4-yl)propenoate (14.30 g), 5% palladium-carbon (28.00 g), ethanol (150 ml) and tetrahydrofuran (150 ml) was stirred under a hydrogen atmosphere at room temperature for 3 hrs. Palladium-carbon was filtered off and the filtrate was concentrated. The obtained crystals were collected by filtration to give ethyl 3-(1-benzyl-3-hydroxy-1H-pyrazol-4-yl)propionate (9.01 g, yield 83%). The crystals were recrystallized from ethyl acetate-hexane. melting point: 75–76° C.

REFERENCE EXAMPLE 46

A mixture of (3-benzyloxy-1-phenyl-1H-pyrazol-4-yl)methanol (5.61 g), active manganese dioxide (15.00 g) and tetrahydrofuran (75 ml) was stirred overnight at room temperature. Manganese dioxide was filtered off and the filtrate was concentrated. The residue was subjected to silica gel column chromatography, and 3-benzyloxy-1-phenyl-1H-pyrazole-4-carbaldehyde (5.03 g, yield 90%) was obtained as colorless crystals from a fraction eluted with ethyl acetate-hexane (2:1, volume ratio). The crystals were recrystallized from tetrahydrofuran-hexane. melting point: 153–154° C.

REFERENCE EXAMPLE 47

To a mixture of potassium t-butoxide (3.82 g) and dimethoxyethane (20 ml) was added a solution of p-toluenesulfonylmethyl isocyanide (3.51 g) in dimethoxyethane (20 ml) and the mixture was stirred at −78° C. for 5 min. Then a solution of 3-benzyloxy-1-phenyl-1H-pyrazole-4-carbaldehyde (4.73 g) in dimethoxyethane (80 ml) was added. After stirring at said temperature for 1 hr, the mixture was stirred for 1 hr. while raising the temperature to room temperature. To the obtained mixture was added methanol (100 ml), and the mixture was refluxed for 1 hr. After cooling, the reaction solution was poured into saturated aqueous ammonium chloride solution and the mixture was extracted with ethyl acetate. The ethyl acetate layer was washed with saturated brine, dried (MgSO$_4$) and concentrated. The residue was subjected to silica gel column chromatography, and 3-benzyloxy-1-phenyl-1H-pyrazol-4-ylacetonitrile (3.31 g, yield 67%). was obtained as colorless crystals from a fraction eluted with ethyl acetate-hexane (1:3, volume ratio). The crystals were recrystallized from tetrahydrofuran-hexane. melting point: 102–103° C.

REFERENCE EXAMPLE 48

A mixture of 3-benzyloxy-1-phenyl-1H-pyrazol-4-ylacetonitrile (3.01 g), 6N aqueous sodium hydroxide solution (25 ml), tetrahydrofuran (25 ml) and ethanol (25 ml) was refluxed for 3 days. After cooling, the mixture was neutralized with dilute hydrochloric acid and extracted with ethyl acetate. The ethyl acetate layer was washed with saturated brine, dried (MgSO$_4$) and concentrated to give 3-benzyloxy-1-phenyl-1H-pyrazol-4-ylacetic acid (2.63 g, yield 82%) as colorless crystals. The crystals were recrystallized from acetone-hexane. melting point: 105–106° C.

REFERENCE EXAMPLE 49

A mixture of 3-benzyloxy-1-phenyl-1H-pyrazol-4-ylacetic acid (2.47 g), methyl iodide (0.75 ml), potassium carbonate (2.21 g) and N,N-dimethylformamide (25 ml) was stirred at room temperature for 1 hr. The reaction solution was poured into water and the mixture was extracted with ethyl acetate. The ethyl acetate layer was washed with saturated brine, dried (MgSO$_4$) and concentrated. The residue was subjected to silica gel column chromatography, and 3-benzyloxy-1-phenyl-1H-pyrazol-4-ylmethyl acetate (2.55 g, yield 99%) was obtained as colorless crystals from a fraction eluted with ethyl acetate-hexane (1:3, volume ratio). The crystals were recrystallized from ethyl acetate-hexane. melting point: 74–75° C.

REFERENCE EXAMPLE 50

A mixture of 3-benzyloxy-1-phenyl-1H-pyrazol-4-ylmethyl acetate (2.35 g), 5% palladium-carbon (4.00 g), tetrahydrofuran (25 ml) and methanol (25 ml) was stirred under a hydrogen atmosphere for 1 hr. Palladium-carbon was filtered off and the filtrate was concentrated to give methyl 3-hydroxy-1-phenyl-1H-pyrazol-4-ylacetate (1.58 g, yield 93%) as colorless crystals. The crystals were recrystallized from ethyl acetate-hexane. melting point: 144–145° C.

REFERENCE EXAMPLE 51

To a mixture of (5-methyl-2-phenyl-4-thiazolyl)methanol (5.00 g), 6-chloro-3-cyanopyridine (3.38 g) and N,N-dimethylformamide (100 ml) was added sodium hydride (60% in oil, 1.07 g) under ice-cooling. The reaction mixture was stirred at room temperature for 1 hr. Water was poured into the reaction mixture and the mixture was extracted with ethyl acetate. The organic layer was washed with saturated brine, dried over anhydrous magnesium sulfate, and concentrated. The obtained residue was subjected to silica gel column chromatography, and 6-(5-methyl-5-phenyl-4-thiazolylmethoxy)nicotinonitrile was obtained as colorless crystals (5.55 g, yield 74%) from a fraction eluted with ethyl acetate-hexane (1:2, volume ratio). The crystals were recrystallized from ethyl acetate-hexane. melting point: 124–125° C.

REFERENCE EXAMPLE 52

To a mixture of 6-(5-methyl-5-phenyl-4-thiazolylmethoxy)nicotinonitrile (5.45 g) and absolute toluene (150 ml) was added dropwise a solution (0.95 M, 41.0 ml) of diisobutylaluminum hydride in hexane at −78° C. The reaction mixture was stirred for 1.5 hrs. until it warmed to room temperature. Saturated aqueous ammonium chloride solution (100 ml) was added dropwise and the mixture was further stirred at room temperature for 30 min. To this mixture was added ethyl acetate and the mixture was stirred at room temperature for 30 min. Insoluble materials were filtered off. The filtrate was washed with saturated brine, dried over anhydrous magnesium sulfate, and concentrated. The obtained residue was subjected to silica gel column chromatography, and 6-(5-methyl-2-phenyl-4-thiazolylmethoxy)nicotinealdehyde was obtained as colorless crystals (4.30 g, yield 78%) from a fraction eluted with ethyl acetate-hexane (1:4, volume ratio). The crystals were recrystallized from ethyl acetate-hexane. melting point: 120–121° C.

REFERENCE EXAMPLE 53

To a mixture of [2-(2-furyl)-5-methyl-4-oxazolyl]methanol (5.18 g), 6-chloro-3-cyanopyridine (4.00 g) and N,N-dimethylformamide (100 ml) was added sodium hydride (60% in oil, 1.27 g) under ice-cooling. The reaction mixture was stirred at room temperature for 1 hr. Water was poured into the reaction mixture and the mixture was extracted with ethyl acetate. The organic layer was washed successively with water and saturated brine, dried over anhydrous magnesium sulfate, and concentrated. The obtained residue was subjected to silica gel column chromatography, and 6-[2-(2-furyl)-5-methyl-4-oxazolylmethoxy]nicotinonitrile was obtained as colorless crystals (6.97 g, yield 86%) from a fraction eluted with ethyl acetate-hexane (1:2, volume ratio). The crystals were recrystallized from ethyl acetate-hexane. melting point: 105–106° C.

REFERENCE EXAMPLE 54

To a mixture of 6-[2-(2-furyl)-5-methyl-4-oxazolylmethoxy]nicotinonitrile (6.77 g) and absolute toluene (150 ml) was added dropwise a solution (0.95 M, 55.8 ml) of diisobutylaluminum hydride in hexane at −78° C. The reaction mixture was stirred for 1 hr. until warmed to room temperature. Saturated aqueous ammonium chloride solution (100 ml) was added dropwise and the mixture was further stirred at room temperature for 30 min. To this mixture was added ethyl acetate and the mixture was stirred at room temperature for 30 min. Insoluble materials were filtered off. The filtrate was washed with saturated brine, dried over anhydrous magnesium sulfate and concentrated. The obtained residue was subjected to silica gel column chromatography, and 6-[2-(2-furyl)-5-methyl-4-oxazolylmethoxy]nicotinealdehyde was obtained as colorless crystals (3.25 g, yield 47%) from a fraction eluted with ethyl acetate-hexane (1:2, volume ratio). The crystals were recrystallized from ethyl acetate-hexane. melting point: 139–140° C.

REFERENCE EXAMPLE 55

To a mixture of methyl 4-hydroxy-5-oxo-5-phenylpentanoate (4.50 g), pyridine (1.80 ml) and tetrahydrofuran (30 ml) was slowly added phenyl chlorocarbonate (2.80 ml) at 0° C. and the mixture was stirred at room temperature for 2 hrs. Water was poured into the reaction mixture and the mixture was extracted with ethyl acetate. The organic layer was washed successively with water and saturated brine, dried over anhydrous magnesium sulfate and concentrated. The obtained residue was dissolved in acetic acid (30 ml), ammonium acetate (7.79 g) was added and the mixture was refluxed for 3 hrs. The reaction mixture was concentrated and the obtained residue was dissolved in ethyl acetate, washed with saturated aqueous sodium hydrogen carbonate and then saturated brine, dried over anhydrous magnesium sulfate and concentrated. The obtained residue was subjected to silica gel column chromatography, and methyl 3-(2-oxo-4-phenyloxazolin-5-yl)propionate was obtained as colorless crystals (3.57 g, yield 71%) from a fraction eluted with ethyl acetate-hexane (1:2, volume ratio). The crystals were recrystallized from ethyl acetate-hexane. melting point: 104–105° C.

REFERENCE EXAMPLE 56

A mixture of methyl 3-(2-oxo-4-phenyloxazolin-5-yl)propionate (3.00 g), pyridine (0.98 ml) and phosphoric oxychloride (7.62 g) was stirred at 105° C. for 2 hrs. The reaction mixture was slowly poured into ice water and the mixture was extracted with ethyl acetate. The organic layer was washed successively with saturated aqueous sodium hydrogen carbonate and saturated brine, dried over anhydrous magnesium sulfate and concentrated. The obtained residue was subjected to silica gel column chromatography, and methyl 3-(2-chloro-4-phenyl-5-oxazolyl)propionate (2.40 g, yield 75%) was obtained as a colorless oil from a fraction eluted with ethyl acetate-hexane (1:7, volume ratio).

NMR(CDCl$_3$) δ: 2.74 (2H, t, J=7.6 Hz), 3.23 (2H, t, J=7.6 Hz), 3.69 (3H, s), 7.30–7.65 (5H, m).

REFERENCE EXAMPLE 57

A mixture of methyl 3-(2-chloro-4-phenyl-5-oxazolyl)propionate (500 mg), 4-hydroxythiophenol (475 mg), potassium carbonate (520 mg) and N,N-dimethylformamide (10 ml) was stirred at room temperature for 2 hrs. The reaction mixture was poured into water and the mixture was extracted with ethyl acetate. The organic layer was washed successively with dilute hydrochloric acid and saturated brine, dried over anhydrous magnesium sulfate and concentrated to give methyl 3-[2-(4-hydroxyphenylthio)-4-phenyl-5-oxazolyl]propionate as colorless crystals (637 mg, yield 95%). The crystals were recrystallized from toluene-hexane. melting point: 157–158° C.

REFERENCE EXAMPLE 58

A mixture of methyl 4-bromo-5-oxo-5-phenylpentanoate (15.0 g), thiourea (3.81 g) and methanol (200 ml) was refluxed for 2 hrs. The reaction solvent was removed under reduced pressure, and the residue was dissolved in ethyl acetate. The obtained solution was washed successively with saturated aqueous sodium hydrogen carbonate and saturated brine, dried over anhydrous magnesium sulfate and concentrated to give methyl 3-(2-amino-4-phenyl-5-thiazolyl)propionate (11.9 g, yield 90%) as pale-yellow crystals. The crystals were recrystallized from ethyl acetate-hexane. melting point: 130–131° C.

REFERENCE EXAMPLE 59

To a mixture of methyl 3-(2-amino-4-phenyl-5-thiazolyl)propionate (2.00 g), copper(II) chloride (1.54 g) and tetrahydrofuran (10 ml) was slowly added t-butyl nitrite (1.51 ml) and the mixture was stirred at room temperature for 2 hrs. The reaction mixture was poured into water and the mixture was extracted with ethyl acetate. The organic layer was washed with saturated brine, dried over anhydrous magnesium sulfate and concentrated. The obtained residue was subjected to silica gel column chromatography, and methyl 3-(2-chloro-4-phenyl-5-thiazolyl)propionate (740 mg, yield 34%) was obtained as a colorless oil from a fraction eluted with ethyl acetate-hexane (1:9, volume ratio).

NMR(CDCl$_3$) δ: 2.65 (2H, t, J=7.4 Hz), 3.23 (2H, t, J=7.4 Hz), 3.69 (3H, s), 7.30–7.58 (5H, m).

REFERENCE EXAMPLE 60

A mixture of methyl 3-(2-chloro-4-phenyl-5-thiazolyl)propionate (380 mg), 4-hydroxythiophenol (341 mg), potassium carbonate (373 mg) and N,N-dimethylformamide (7 ml) was stirred at room temperature for 5 hrs. The reaction mixture was poured into water and the mixture was extracted with ethyl acetate. The organic layer was washed successively with dilute hydrochloric acid and saturated brine, dried over anhydrous magnesium sulfate, and-concentrated to give methyl 3-[2-(4-hydroxyphenylthio)-4-phenyl-5-thiazolyl]propionate (464 mg, yield 93%) as colorless crystals. The crystals were recrystallized from toluene-hexane. melting point: 153–155° C.

REFERENCE EXAMPLE 61

A mixture of methyl 4-bromo-5-oxo-5-phenylpentanoate (5.00 g), N-propylthiourea (2.01 g) and methanol (50 ml) was refluxed for 2 hrs. The reaction solvent was removed under reduced pressure, and the residue was dissolved in ethyl acetate. The obtained solution was washed successively with saturated aqueous sodium hydrogen carbonate and saturated brine, dried over anhydrous magnesium sulfate, and concentrated to give methyl 3-[4-phenyl-2-[N-(1-propyl)amino]-5-thiazolyl]propionate (3.64 g, yield 70%) as colorless crystals. The crystals were recrystallized from ethyl acetate-hexane. melting point: 67–68° C.

REFERENCE EXAMPLE 62

To a mixture of (2-amino-4-thiazolyl)ethyl acetate (5.00 g), copper(II) chloride (5.41 g) and tetrahydrofuran (80 ml) was slowly added t-butyl nitrite (5.32 ml) at 0° C., and the mixture was stirred at said temperature for 3 hrs. The reaction mixture was poured into water and the mixture was extracted with ethyl acetate. The organic layer was washed with saturated brine, dried over anhydrous magnesium sulfate and concentrated. The obtained residue was subjected to silica gel column chromatography, and (2-chloro-4-thiazolyl)ethyl acetate (880 mg, yield 16%) was obtained as a colorless oil from a fraction eluted with ethyl acetate-hexane (1:8, volume ratio).

NMR(CDCl$_3$) δ: 1.28 (3H, t, J=7.1 Hz), 3.77 (2H, s), 4.20 (2H, q, J=7.1 Hz), 7.13 (1H, s).

REFERENCE EXAMPLE 63

To a mixture of 3-benzyloxy-1-phenyl-1H-pyrazole-4-carbaldehyde (3.00 g), diethylphosphonoethyl acetate (2.67 g) and N,N-dimethylformamide (50 ml) was added sodium hydride (60% in oil, 0.52 g) at 0° C. and the mixture was stirred at room temperature for 15 hrs. The reaction mixture was poured into water and the mixture was extracted with ethyl acetate. The ethyl acetate layer was washed successively with dilute hydrochloric acid and saturated brine, dried (MgSO$_4$) and concentrated. The obtained crystals were collected by filtration to give ethyl (E)-3-(3-benzyloxy-1-phenyl-1H-pyrazol-4-yl)propenoate (3.18 g, yield 85%), which was then recrystallized from ethyl acetate-hexane. melting point: 105–106° C.

REFERENCE EXAMPLE 64

A mixture of ethyl (E)-3-(3-benzyloxy-1-phenyl-1H-pyrazol-4-yl)propenoate (2.70 g), 5% palladium-carbon (3.00 g) and tetrahydrofuran (100 ml) was stirred under a hydrogen atmosphere at room temperature for 3 hrs. Palladium-carbon was filtered off and the filtrate was concentrated. The obtained crystals were collected by filtration to give ethyl 3-(3-benzyloxy-1-phenyl-1H-pyrazol-4-yl)propionate (1.78 g, yield 89%), which was then recrystallized from ethyl acetate-hexane. melting point: 123–124° C.

REFERENCE EXAMPLE 65

A mixture of 4-methoxymethoxymethyl-2-phenyloxazole-5-carbaldehyde (3.00 g), 4-benzyloxybenzyltriphenylphosphonium chloride (6.58 g), potassium carbonate (1.84 g) and N,N-dimethylformamide (50 ml) was stirred at room temperature for 15 hrs. The reaction mixture was poured into water and the mixture was extracted with ethyl acetate. The organic layer was washed successively with dilute hydrochloric acid and saturated brine, dried over anhydrous magnesium sulfate, and concentrated. The obtained residue was subjected to silica gel column chromatography, and a colorless oil was obtained from a fraction eluted with ethyl acetate-hexane (1:4, volume ratio). A mixture of the obtained colorless oil, 5% palladium-carbon (5.00 g) and tetrahydrofuran (200 ml) was stirred under a hydrogen atmosphere at room temperature for 3 hrs. Palladium-carbon was filtered off and the filtrate was concentrated. The obtained crystals were collected by filtration to give 5-[2–5 (4-hydroxyphenyl)ethyl]-4-methoxymethoxymethyl-2-phenyloxazole (3.24 g, yield 79%), which was then recrystallized from ethyl acetate-hexane. melting point: 102–103° C.

REFERENCE EXAMPLE 66

A mixture of 5-[2-(4-hydroxyphenyl)ethyl]-4-methoxymethoxymethyl-2-phenyloxazole (3.12 g), 4-chloromethyl-5-methyl-2-phenyloxazole (2.28 g), potassium carbonate (1.27 g) and N,N-dimethylformamide (50 ml) was stirred at 90° C. for 15 hrs. The reaction mixture was poured into water and the mixture was extracted with ethyl acetate. The organic layer was washed successively with dilute hydrochloric acid and saturated brine, dried over anhydrous magnesium sulfate, and concentrated. The obtained residue was subjected to silica gel column chromatography, and 5-[2-[4-(5-methyl-2-phenyl-4-oxazolyl)methoxyphenyl]ethyl]-4-methoxymethoxymethyl-2-phenyloxazole (4.70 g, yield 85%) as colorless crystals from a fraction eluted with ethyl acetate-hexane (1:3, volume ratio). The crystals were recrystallized from ethyl acetate-hexane. melting point: 124–125° C.

REFERENCE EXAMPLE 67

A mixture of 5-[2-[4-(5-methyl-2-phenyl-4-oxazolyl)methoxyphenyl]ethyl]-4-methoxymethoxymethyl-2-phenyloxazole (3.80 g), 10% sulfuric acid (10 ml) and tetrahydrofuran (100 ml) was refluxed for 2 hrs., and concentrated. Ethyl acetate was poured into the residue and the mixture was washed with saturated brine, dried over anhydrous magnesium sulfate, and concentrated. The obtained residue was subjected to silica gel column chromatography, and [5-[2-[4-(5-methyl-2-phenyl-4-oxazolyl)methoxyphenyl]ethyl]-2-phenyl-4-oxazolyl]methanol (2.03 g, yield 59%) was obtained as colorless crystals from a fraction eluted with ethyl acetate-hexane (1:2, volume ratio). The crystals were recrystallized from ethyl acetate-hexane. melting point: 142–143° C.

REFERENCE EXAMPLE 68

A mixture of [5-[2-[4-(5-methyl-2-phenyl-4-oxazolyl)methoxyphenyl]ethyl]-2-phenyl-4-oxazolyl]methanol (1.00 g) and thionyl chloride (2 ml) was stirred at 0° C. for 1 hr., and concentrated. Ethyl acetate was poured into the residue, the mixture was washed successively with saturated aqueous sodium hydrogen carbonate and saturated brine, dried over anhydrous magnesium sulfate, and concentrated. A mixture of the obtained residue, sodium cyanide (210 mg) and dimethyl sulfoxide (20 ml) was stirred at room temperature for 15 hrs. The reaction mixture was poured into water and the mixture was extracted with ethyl acetate. The organic layer was washed successively with dilute hydrochloric acid and saturated brine, dried over anhydrous magnesium sulfate, and concentrated. The obtained residue was subjected to silica gel column chromatography, and [5-[2-[4-(5-methyl-2-phenyl-4-oxazolyl)methoxyphenyl]ethyl]-2-phenyl-4-oxazolyl]acetonitrile (560 g, yield 56%) was obtained as colorless crystals from a fraction eluted with ethyl acetate-hexane (1:2, volume ratio). The crystals were recrystallized from ethyl acetate-hexane. melting point: 97–98° C.

REFERENCE EXAMPLE 69

A mixture of [5-[2-[4-(5-methyl-2-phenyl-4-oxazolyl)methoxyphenyl]ethyl]-2-phenyl-4-oxazolyl]methanol (0.78 g) and thionyl chloride (2 ml) was stirred at 0° C. for 30 min, and concentrated. Ethyl acetate was poured into the residue, washed successively with saturated aqueous sodium hydrogen carbonate and saturated brine, dried over anhydrous magnesium sulfate, and concentrated. To a solution of the obtained residue in tetrahydrofuran (10 ml) was added a mixture of diethyl malonate (1.36 g), sodium hydride (60% in oil, 0.33 g) and tetrahydrofuran (30 ml) at 0° C. The mixture was stirred at room temperature for 15 hrs. and refluxed for 1 hr. The reaction mixture was poured into water and the mixture was extracted with ethyl acetate. The organic layer was washed successively with dilute hydrochloric acid and saturated brine, dried over anhydrous magnesium sulfate, and concentrated. The obtained residue was subjected to silica gel column chromatography, and ethyl 2-ethoxycarbonyl-3-[5-[2-[4-(5-methyl-2-phenyl-4-oxazolyl)methoxyphenyl]ethyl]-2-phenyl-4-oxazolyl]propionate (550 g, yield 53%) was obtained as a colorless oil from a fraction eluted with ethyl acetate-hexane (1:6, volume ratio).

NMR(CDCl$_3$) δ: 1.23 (6H, t, J=7.0 Hz), 2.43 (3H, s), 2.86–2.99 (6H, m), 3.82 (1H, t, J=7.6 Hz), 4.18 (2H, q, J=7.0 Hz), 4.97 (2H, s), 6.92–6.97 (2H, m), 7.11–7.15 (2H, m), 7.40–7.45 (6H, m), 7.93–8.05 (4H, m).

REFERENCE EXAMPLE 70

A mixture of methyl 4-bromo-5-oxo-5-phenylpentanoate (2.00 g), N-methylthiourea (640 mg), sodium acetate (640 mg) and ethanol (15 ml) was heated under reflux for 30 min. The reaction mixture was poured into water and the precipitated colorless crystals of methyl 3-[2-[N-(1-methyl)amino]-4-phenyl-5-thiazolyl]propionate (1.50 g, yield 77%) were collected by filtration and recrystallized from ethyl acetate-isopropyl ether. melting point: 90–91° C.

REFERENCE EXAMPLE 71

To a solution of succinic acid monoethyl ester (22.0 g) and triethylamine (16.8 g) in tetrahydrofuran (150 ml) was added dropwise chloroethyl formate (18.0 g) at −20° C. After stirring for 30 min., pulverized thiosemicarbazide (13.7 g) was added and the mixture was stirred at room temperature for 7 hrs. Water was added to the reaction mixture, acidified with 2N hydrochloric acid and extracted with chloroform. The aqueous layer was separated and sodium chloride was added. The mixture was extracted with ethyl acetate. The ethyl acetate layer was washed with saturated brine, dried (MgSO$_4$) and concentrated. The residual crystals were recrystallized from dichloromethane-ethanol to give ethyl 4-[2-(aminocarbothioyl)hydrazino]-4-oxobutanoate as colorless prism crystals (8.23 g, 25%). melting point: 143–144° C.

REFERENCE EXAMPLE 72

A mixture of colorless prism crystals (8.00 g) of ethyl 4-[2-(aminocarbothioyl)hydrazino]-4-oxobutanoate, 28% sodium methoxide-methanol solution (1.40 g) and ethanol (30 ml) was heated under reflux for 8 hrs. The reaction mixture was poured into ice water, and acidified with 2N hydrochloric acid to precipitate ethyl 3-(5-mercapto-1H-1,2,4-triazol-3-yl)propionate as crystals (4.27 g, 58%). Recrystallization from ethanol-water gave colorless prism crystals. melting point: 178–179° C.

REFERENCE EXAMPLE 73

To a solution of ethyl 3,5-dihydroxybenzoate (15.0 g) in N,N-dimethylformamide (180 ml) was gradually added sodium hydride (60% in oil, 3.30 g) at 0° C. and the mixture was stirred for 30 min. Iodoethane (12.9 g) was added and the mixture was further stirred for 2 hrs. The reaction mixture was poured into water, acidified with 2N hydrochloric acid and the mixture was extracted with ethyl acetate. The ethyl acetate layer was washed with water, dried (MgSO$_4$) and concentrated. The obtained residue was subjected to silica gel column chromatography, and ethyl 3-ethoxy-5-hydroxybenzoate (6.75 g, yield 39%) was obtained as crystals from a fraction eluted with ethyl acetate-hexane (1:3, volume ratio). Recrystallization from diethyl ether-hexane gave colorless needle-shaped crystals. melting point: 62–63° C.

REFERENCE EXAMPLE 74

A mixture of ethyl 3-ethoxy-5-hydroxybenzoate (3.00 g), 4-chloromethyl-5-methyl-2-phenyloxazole (3.26 g), potassium carbonate (2.17 g) and N,N-dimethylformamide (60 ml) was stirred at 80° C. for 2 hrs. The reaction mixture was poured into water, acidified with 2N hydrochloric acid and the mixture was extracted with ethyl acetate. The ethyl acetate layer was washed with water, dried (MgSO$_4$) and concentrated. The obtained residue was subjected to silica gel column chromatography, and ethyl 3-ethoxy-5-(5-methyl-2-phenyl-4-oxazolylmethoxy)benzoate (5.40 g, 99%) was obtained as an oil from a fraction eluted with ethyl acetate-hexane (1:4, volume ratio).

NMR(CDCl$_3$) δ: 1.38 (3H, t, J=7 Hz), 1.41 (3H, t, J=7 Hz), 2.46 (3H, s), 4.05 (2H, q, J=7 Hz), 4.36 (2H, q, J=7 Hz), 5.01 (2H, s), 6.77 (1H, t, J=2 Hz), 7.22 (1H, dd, J=2, 1 Hz), 7.30 (1H, dd, J=2, 1 Hz), 7.4–7.5(3H, m), 7.95–8.05 (2H, m).

REFERENCE EXAMPLE 75

A mixture of methyl 3-hydroxy-1-phenyl-1H-pyrazole-5-carboxylate (5.60 g), 4-(4-chloromethyl-2-methoxyphenoxymethyl)-2-(2-furyl)-5-methyloxazole (9.45 g), potassium carbonate (3.55 g) and N,N-dimethylformamide (200 ml) was stirred at 90° C. for 15 hrs. The reaction mixture was poured into water and the mixture was extracted with ethyl acetate. The ethyl acetate layer was washed with saturated brine, dried (MgSO$_4$) and concentrated. The obtained colorless crystals were collected by filtration to give methyl 3-[4-[2-(2-furyl)-5-methyl-4-oxazolylmethoxy]-3-methoxybenzyloxy]-1-phenyl-1H-pyrazole-5-carboxylate (12.40 g, yield 94%). The crystals were recrystallized from ethyl acetate-hexane. melting point: 146–147° C.

REFERENCE EXAMPLE 76

To a solution of methyl 3-[4-[2-(2-furyl)-5-methyl-4-oxazolylmethoxy]-3-methoxybenzyloxy]-1-phenyl-1H-pyrazole-5-carboxylate (12.10 g) in tetrahydrofuran (300 ml) was added aluminum lithium hydride (890 mg) at 0° C. and the mixture was stirred at room temperature for 1 hr. Sodium sulfate 10 hydrate (7.57 g) was added to the reaction mixture and stirred at room temperature for 1 hr. The precipitate was filtered off and the filtrate was concentrated. The obtained colorless crystals were collected by filtration to give [3-[4-[2-(2-furyl)-5-methyl-4-oxazolylmethoxy]-3-methoxybenzyloxy]-1-phenyl-1H-pyrazol-5-yl]methanol (11.19 g, yield 98%), which was then recrystallized from ethyl acetate-hexane. melting point: 106–107° C.

REFERENCE EXAMPLE 77

A mixture of [3-[4-[2-(2-furyl)-5-methyl-4-oxazolylmethoxy]-3-methoxybenzyloxy]-1-phenyl-1H-pyrazol-5-yl]methanol (9.50 g), active manganese dioxide (30.00 g) and tetrahydrofuran (300 ml) was stirred at room temperature for 15 hrs. Manganese dioxide was filtered off and the filtrate was concentrated. The residue was subjected to silica gel column chromatography, and 3-[4-[2-(2-furyl)-5-methyl-4-oxazolylmethoxy]-3-methoxybenzyloxy]-1-phenyl-1H-pyrazole-5-carbaldehyde (7.27 g, yield 77%) was obtained as colorless crystals from a fraction eluted with ethyl acetate-hexane (1:1, volume ratio). The crystals were recrystallized from ethyl acetate-hexane. melting point: 103–104° C.

REFERENCE EXAMPLE 78

To a mixture of potassium t-butoxide (1.46 g) and dimethoxyethane (50 ml) was added a solution of p-toluenesulfonylmethyl isocyanide (1.33 g) in dimethoxyethane (50 ml) at −78° C. and the mixture was stirred for 5 min. Then a solution of 3-[4-[2-(2-furyl)-5-methyl-4-oxazolylmethoxy]-3-methoxybenzyloxy]-1-phenyl-1H-pyrazole-5-carbaldehyde (3.00 g) in dimethoxyethane (50 ml) was added. After stirring at said temperature for 1 hr, the mixture was stirred for 1 hr. while raising the temperature to room temperature. To the obtained mixture was added methanol (50 ml), and the mixture was refluxed for 2 hrs. After cooling, the reaction solution was poured into saturated aqueous ammonium chloride solution and the mixture was extracted with ethyl acetate. The ethyl acetate layer was washed with saturated brine, dried (MgSO$_4$) and concentrated. The residue was subjected to silica gel column chromatography, and [3-[4-[2-(2-furyl)-5-methyl-4-oxazolylmethoxy]-3-methoxybenzyloxy-]-1-phenyl-1H-pyrazol-5-yl]acetonitrile (450 mg, yield 15%) was obtained as colorless crystals from a fraction eluted with ethyl acetate-hexane (1:1, volume ratio). The crystals were recrystallized from ethyl acetate-hexane. melting point: 141–142° C.

REFERENCE EXAMPLE 79

A mixture of 3-hydroxy-1-phenyl-1H-pyrazole-5-carboxylic acid (29.55 g), benzyl bromide (35 ml), potassium carbonate (40.99 g) and N,N-dimethylformamide (300 ml) was stirred overnight at 90° C. The reaction mixture was poured into dilute hydrochloric acid and the mixture was extracted with ethyl acetate. The ethyl acetate layer was washed with saturated brine, dried (MgSO$_4$) and concentrated. The residue was subjected to silica gel column chromatography, and benzyl 3-benzyloxy-1-phenyl-1H-pyrazole-5-carboxylate (51.33 g, yield 92%) was obtained as a colorless oil from a fraction eluted with ethyl acetate-hexane (1:2, volume ratio).

$^1$H-NMR(CDCl$_3$) δ:5.20 (2H, s), 5.27 (2H, s), 6.49 (1H, s), 7.18–7.47 (15H, m).

REFERENCE EXAMPLE 80

A mixture of benzyl 3-benzyloxy-1-phenyl-1H-pyrazole-5-carboxylate (50.88 g), 1N aqueous sodium hydroxide solution (200 ml), tetrahydrofuran (200 ml) and ethanol (200 ml) was refluxed at room temperature for 5 hrs. 1N Hydrochloric acid (200 ml) was added and the mixture was extracted with ethyl acetate. The ethyl acetate layer was washed with saturated brine, dried (MgSO$_4$) and concentrated. The obtained colorless crystals were collected by filtration to give 3-benzyloxy-1-phenyl-1H-pyrazole-5-carboxylic acid (36.91 g, yield 95%), which was then recrystallized from acetone-isopropyl ether. melting point: 163–164° C.

REFERENCE EXAMPLE 81

A mixture of 3-benzyloxy-1-phenyl-1H-pyrazole-5-carboxylic acid (33.00 g), methane iodide (8.5 ml), potassium carbonate (18.88 g) and N,N-dimethylformamide (300 ml) was stirred overnight at room temperature. The reaction mixture was poured into dilute hydrochloric acid and the mixture was extracted with ethyl acetate. The ethyl acetate layer was washed with saturated brine, dried (MgSO$_4$) and concentrated. The residue was subjected to silica gel column chromatography, and methyl 3-benzyloxy-1-phenyl-1H-pyrazole-5-carboxylate (33.48 g, yield 97%) was obtained as colorless crystals from a fraction eluted with ethyl acetate-hexane (1:4, volume ratio). The crystals were recrystallized from ethyl acetate-hexane. melting point: 53–54° C.

REFERENCE EXAMPLE 82

To a mixture of methyl 3-benzyloxy-1-phenyl-1H-pyrazole-5-carboxylate (14.53 g) and tetrahydrofuran (300 ml) was slowly added aluminum lithium hydride (1.79 g) at 0° C. and the mixture was stirred at room temperature for 1 hr. Sodium sulfate 10 hydrate (15.20 g) was slowly added to the reaction mixture at 0° C. and the mixture was stirred at room temperature for 30 min. Insoluble materials were filtered off and the filtrate was concentrated. The residue was subjected to silica gel column chromatography, and (3-benzyloxy-1-phenyl-1H-pyrazol-5-yl)methanol (11.65 g, yield 88%) was obtained as colorless crystals from a fraction eluted with ethyl acetate-hexane (1:2, volume ratio). The crystals were recrystallized from ethyl acetate-hexane. melting point: 87–88° C.

REFERENCE EXAMPLE 83

A mixture of (3-benzyloxy-1-phenyl-1H-pyrazol-5-yl)methanol (11.20 g), active manganese dioxide (30.00 g) and tetrahydrofuran (300 ml) was stirred overnight at room temperature. Insoluble material was filtered off and the filtrate was concentrated. The residue was subjected to silica gel column chromatography, and 3-benzyloxy-1-phenyl-1H-pyrazole-5-carbaldehyde (10.10 g, yield 91%) was obtained as a pale-yellow oil from a fraction eluted with ethyl acetate-hexane (1:2, volume ratio).

$^1$H-NMR(CDCl$_3$) δ: 5.31 (2H, s), 6.51 (1H, s), 7.32–7.52 (10H, m), 9.78 (1H, s).

REFERENCE EXAMPLE 84

To a mixture of 3-benzyloxy-1-phenyl-1H-pyrazole-5-carbaldehyde (6.24 g), diethylphosphonoethyl acetate (5.55 g) and N,N-dimethylformamide (50 ml) was added sodium hydride (60% in oil, 960 mg) at 0° C. and the mixture was stirred overnight at room temperature. The reaction mixture was poured into water and the mixture was extracted with ethyl acetate. The ethyl acetate layer was washed successively with dilute hydrochloric acid and then saturated brine, dried (MgSO$_4$) and concentrated. The residue was subjected to silica gel column chromatography, and ethyl (E)-3-(3-benzyloxy-1-phenyl-1H-pyrazol-5-yl)propenoate (7.33 g, yield 94%) was obtained as a pale-yellow oil from a fraction eluted with ethyl acetate-hexane (1:4, volume ratio).

REFERENCE EXAMPLE 85

A mixture of ethyl (E)-3-(3-benzyloxy-1-phenyl-1H-pyrazol-5-yl)propenoate (7.33 g), 5% palladium-carbon (7.11 g) and tetrahydrofuran (50 ml) was stirred overnight under a hydrogen atmosphere at room temperature. Palladium-carbon was filtered off and the filtrate was concentrated. The residue was subjected to silica gel column chromatography, and ethyl 3-(3-hydroxy-1-phenyl-1H-pyrazol-5-yl)propionate (4.85 g, yield 89%) was obtained as colorless crystals from a fraction eluted with ethyl acetate-hexane (1:2, volume ratio). The crystals were recrystallized from acetone-hexane. melting point: 150–151° C.

EXAMPLE 1

A mixture of methyl 4-[4-(5-methyl-2-phenyl-4-oxazolylmethoxy)phenyl]acetoxy-5-oxo-5-phenylpentanoate (1.34 g), ammonium acetate (685 mg) and acetic acid (5 ml) was refluxed for 3 hrs. After cooling, ethyl acetate was added to the reaction mixture. The obtained ethyl acetate solution was washed with saturated aqueous sodium hydrogen carbonate and then saturated brine, dried (MgSO$_4$) and concentrated. The residue was subjected to silica gel column chromatography, and methyl 3-[2-[4-(5-methyl-2-phenyl-4-oxazolylmethoxy)benzyl]-4-phenyl-5-oxazolyl]propionate (1.07 g, yield 83%) was obtained as a colorless oil from a fraction eluted with ethyl acetate-hexane (2:5, volume ratio).

NMR(CDCl$_3$) δ: 2.43 (3H, s), 2.64–2.73 (2H, m), 3.14–3.22 (2H, m), 3.64 (3H, s), 4.06 (2H, s), 4.98 (2H, s), 6.98 (2H, d, J=8.8 Hz), 7.22–7.47 (8H, m), 7.59–7.66 (2H, m), 7.98–8.04 (2H, m).

EXAMPLE 2

A mixture of methyl 3-[2-[4-(5-methyl-2-phenyl-4-oxazolylmethoxy)benzyl]-4-phenyl-5-oxazolyl]propionate (1.00 g), lithium hydroxide hydrate (171 mg), tetrahydrofuran (6 ml), water (4 ml) and methanol (4 ml) was stirred at room temperature for 1 hr. 1N Hydrochloric acid (5.8 ml) was added to the reaction mixture and the mixture was extracted with ethyl acetate. The ethyl acetate layer was washed with saturated brine, dried (MgSO$_4$) and concentrated to give 3-[2-[4-(5-methyl-2-phenyl-4-oxazolylmethoxy)benzyl]-4-phenyl-5-oxazolyl]propionic acid (918 mg, yield 94%) as colorless crystals. The crystals were recrystallized from ethyl acetate-hexane. melting point: 142–143° C.

EXAMPLE 3

A mixture of methyl 4-[4-(5-methyl-2-phenyl-4-oxazolylmethoxy)phenyl]acetamide-5-oxo-5-phenylpentanoate (600 mg), ammonium acetate (307 mg) and acetic acid (5 ml) was refluxed for 4 hrs. After cooling, ethyl acetate was added to the reaction mixture. The obtained ethyl acetate solution was washed with saturated aqueous sodium hydrogen carbonate and then saturated brine, dried ($MgSO_4$) and concentrated. The residue was subjected to silica gel column chromatography, and methyl 3-[2-[4-(5-methyl-2-phenyl-4-oxazolylmethoxy)benzyl]-4-phenyl-1H-imidazol-5-yl]propionate (358 mg, yield 62%) was obtained as colorless crystals from a fraction eluted with ethyl acetate-hexane (3:1, volume ratio). The crystals were recrystallized from acetone-hexane. melting point: 128–129° C.

EXAMPLE 4

A mixture of methyl 3-[2-[4-(5-methyl-2-phenyl-4-oxazolylmethoxy)benzyl]-4-phenyl-1H-imidazol-5-yl]propionate (250 mg), lithium hydroxide hydrate (62.0 mg), tetrahydrofuran (6 ml), water (4 ml) and methanol (4 ml) was stirred at room temperature for 1 hr. 1N Hydrochloric acid (1.5 ml) was added to the reaction mixture and the mixture was extracted with ethyl acetate. The ethyl acetate layer was washed with saturated brine, dried ($MgSO_4$) and concentrated to give 3-[2-[4-(5-methyl-2-phenyl-4-oxazolylmethoxy)benzyl]-4-phenyl-1H-imidazol-5-yl]propionic acid (132 mg, yield 54%) as colorless crystals. The crystals were recrystallized from acetone. melting point: 193–196° C.

EXAMPLE 5

A mixture of methyl 4-[4-(5-methyl-2-phenyl-4-oxazolylmethoxy)phenyl]acetamide-5-oxo-5-phenylpentanoate (750 mg), phosphoric oxychloride (437 mg) and toluene (7 ml) was refluxed for 1.5 hrs. After cooling, cold saturated aqueous sodium hydrogen carbonate was added to the reaction mixture and the mixture was extracted with ethyl acetate. The ethyl acetate layer was washed with saturated brine, dried ($MgSO_4$) and concentrated. The residue was subjected to silica gel column chromatography, and methyl 3-[2-[4-(5-methyl-2-phenyl-4-oxazolylmethoxy)benzyl]-5-phenyl-4-oxazolyl]propionate (192 mg, yield 27%) was obtained as a colorless oil from a fraction eluted with ethyl acetate-hexane (2:3, volume ratio).

NMR($CDCl_3$) δ: 2.41 (3H, s), 2.73–2.82 (2H, m), 3.02–3.11 (2H, m), 3.65 (3H, s), 4.06 (2H, s), 4.97 (2H, s), 6.98 (2H, d, J=8.4 Hz), 7.22–7.47 (8H, m), 7.52–7.59 (2H, m), 7.98–8.04 (2H, m).

EXAMPLE 6

A mixture of methyl 3-[2-[4-(5-methyl-2-phenyl-4-oxazolylmethoxy)benzyl]-5-phenyl-4-oxazolyl]propionate (192 mg), lithium hydroxide hydrate (47.6 mg), tetrahydrofuran (6 ml), water (4 ml) and methanol (4 ml) was stirred at room temperature for 1.5 hrs. 1N Hydrochloric acid (1.2 ml) was added to the reaction mixture and the mixture was extracted with ethyl acetate. The ethyl acetate layer was washed with saturated brine, dried ($MgSO_4$) and concentrated to give 3-[2-[4-(5-methyl-2-phenyl-4-oxazolylmethoxy)benzyl]-5-phenyl-4-oxazolyl]propionic acid (158 mg, yield 85%) as colorless crystals. The crystals were recrystallized from ethyl acetate-hexane. melting point: 136–137° C.

EXAMPLE 7

A mixture of methyl 4-[4-(5-methyl-2-phenyl-4-oxazolylmethoxy)phenyl]acetamide-5-oxo-5-phenylpentanoate (600 mg), Lawesson's reagent (530 mg) and toluene (5 ml) was refluxed for 1 hr. After cooling, the mixture was subjected to silica gel column chromatography, and methyl 3-[2-[4-(5-methyl-2-phenyl-4-oxazolylmethoxy)benzyl]-5-phenyl-4-thiazolyl]propionate (562 mg, yield 94%) was obtained as a pale-brown oil from a fraction eluted with ethyl acetate-hexane (1:2, volume ratio).

NMR($CDCl_3$) δ: 2.43 (3H, s), 2.74–2.83 (2H, m), 3.04–3.12 (2H, m), 3.64 (3H, s), 4.23 (2H, s), 4.99 (2H, s), 7.00 (2H, d, J=8.8 Hz), 7.25–7.47 (10H, m), 7.98–8.04 (2H, m).

EXAMPLE 8

A mixture of methyl 3-[2-[4-(5-methyl-2-phenyl-4-oxazolylmethoxy)benzyl]-5-phenyl-4-thiazolyl]propionate (487 mg), lithium hydroxide hydrate (117 mg), tetrahydrofuran (6 ml), water (4 ml) and methanol (4 ml) was stirred at room temperature for 1.5 hrs. 1N Hydrochloric acid (2.8 ml) was added to the reaction mixture and the mixture was extracted with ethyl acetate. The ethyl acetate layer was washed with saturated brine, dried ($MgSO_4$) and concentrated to give 3-[2-[4-(5-methyl-2-phenyl-4-oxazolylmethoxy)benzyl]-5-phenyl-4-thiazolyl]propionic acid (434 mg, yield 92%) as colorless crystals. The crystals were recrystallized from ethyl acetate-hexane. melting point: 119–120° C.

EXAMPLE 9

A mixture of methyl 3-[2-(4-hydroxyphenylthio)-4-phenyl-5-oxazolyl]propionate (450 mg), 4-chloromethyl-5-methyl-2-phenyloxazole (263 mg), potassium carbonate (351 mg) and N,N-dimethylformamide (5 ml) was stirred at 50° C. for 3 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and methyl 3-[2-[4-(5-methyl-2-phenyl-4-oxazolylmethoxy)phenylthio]-4-phenyl-5-oxazolyl]propionate (609 mg, yield 91%) was obtained as a colorless oil from a fraction eluted with ethyl acetate-hexane (1:4, volume ratio).

NMR($CDCl_3$) δ: 2.44 (3H, s), 2.65 (2H, t, J=7.7 Hz), 3.17 (2H, t, J=7.7 Hz), 3.64 (3H, s), 5.01 (2H, s), 7.05 (2H, d, J=8.8 Hz), 7.28–7.48 (6H, m), 7.53–7.65 (4H, m), 7.98–8.05 (2H, m).

EXAMPLE 10

A mixture of methyl 3-[2-[4-(5-methyl-2-phenyl-4-oxazolylmethoxy)phenylthio]-4-phenyl-5-oxazolyl]propionate (250 mg), lithium hydroxide hydrate (61.4 mg), tetrahydrofuran (6 ml), water (4 ml) and methanol (4 ml) was stirred at room temperature for 2 hrs. 1N Hydrochloric acid (1.5 ml) was added to the reaction mixture and the mixture was extracted with ethyl acetate. The ethyl acetate layer was washed with saturated brine, dried ($MgSO_4$) and concentrated to give 3-[2-[4-(5-methyl-2-phenyl-4-oxazolylmethoxy)phenylthio]-4-phenyl-5-oxazolyl]propionic acid (200 mg, yield 82%) as colorless crystals. The crystals were recrystallized from ethyl acetate-hexane. melting point: 136–137° C.

EXAMPLE 11

A mixture of methyl 3-[2-(4-hydroxyphenylthio)-4-phenyl-5-thiazolyl]propionate (350 mg), 4-chloromethyl-5-methyl-2-phenyloxazole (196 mg), potassium carbonate (260 mg) and N,N-dimethylformamide (4 ml) was stirred at 50° C. for 2 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and methyl 3-[2-[4-(5-methyl-2-phenyl-4-oxazolylmethoxy)phenylthio]-4-phenyl-5-thiazolyl]propionate (400 mg, yield 78%) was obtained as a colorless oil from a fraction eluted with ethyl acetate-hexane (1:3, volume ratio).

NMR(CDCl$_3$) δ: 2.47 (3H, s), 2.56 (2H, t, J=7.8 Hz), 3.15 (2H, t, J=7.8 Hz), 3.63 (3H, s), 5.04 (2H, s), 7.09 (2H, d, J=8.8 Hz), 7.33–7.48 (6H, m), 7.54–7.67 (4H, m), 8.00–8.06 (2H, m).

EXAMPLE 12

A mixture of methyl 3-[2-[4-(5-methyl-2-phenyl-4-oxazolylmethoxy)phenylthio]-4-phenyl-5-thiazolyl]propionate (360 mg), lithium hydroxide hydrate (83.5 mg), tetrahydrofuran (6 ml), water (4 ml) and methanol (4 ml) was stirred at room temperature for 2 hrs. 1N Hydrochloric acid (2.1 ml) was added to the reaction mixture and the mixture was extracted with ethyl acetate. The ethyl acetate layer was washed with saturated brine, dried (MgSO$_4$) and concentrated to give 3-[2-[4-(5-methyl-2-phenyl-4-oxazolylmethoxy)phenylthio]-4-phenyl-5-thiazolyl]propionic acid (338 mg, yield 96%) as colorless crystals. The crystals were recrystallized from ethyl acetate-hexane. melting point: 121–122° C.

EXAMPLE 13

To a solution of methyl 3-[2-(N-methylamino)-4-phenyl-5-thiazolyl]propionate (400 mg) in N,N-dimethylformamide (10 ml) was added sodium hydride (60% in oil, 70 mg) at 0° C. and the mixture was stirred at said temperature for 10 min. 4-(Chloromethylphenoxymethyl)-5-methyl-2-phenyloxazole (500 mg) was added and the mixture stirred at room temperature for 1 hr. The reaction mixture was poured into ice water, neutralized with 2N hydrochloric acid and extracted with ethyl acetate. The ethyl acetate layer was washed with water, dried (MgSO$_4$) and concentrated. The residue was subjected to silica gel column chromatography, and methyl 3-[2-[N-methyl-N-[4-(5-methyl-2-phenyl-4-oxazolylmethoxy)benzyl]amino]-4-phenyl-5-thiazolyl]propionate (580 mg, yield 72%) was obtained as a colorless oil from fraction eluted with ethyl acetate-hexane (1:9, volume ratio).

NMR(CDCl$_3$) δ: 2.44 (3H, s), 2.63 (2H, t, J=7.5 Hz), 3.00 (3H, s), 3.13 (2H, t, J=7.5 Hz), 3.67 (3H, s), 4.62 (2H, s), 4.99 (2H, s), 6.99 (2H, d, J=8.8 Hz), 7.2–7.65 (10H, m), 7.95–8.1(2H, m).

EXAMPLE 14

A mixture of methyl 3-[2-[N-methyl-N-[4-(5-methyl-2-phenyl-4-oxazolylmethoxy)benzyl]amino]-4-phenyl-5-thiazolyl]propionate (570 mg), 1N aqueous sodium hydroxide solution (2 ml), tetrahydrofuran (5 ml) and methanol (5 ml) was stirred at room temperature for 1 hr. The reaction mixture was poured into water, neutralized with 2N hydrochloric acid and extracted with ethyl acetate. The ethyl acetate layer was washed with water, dried (MgSO$_4$) and concentrated. The residue was dissolved in diethyl ether (40 ml) and 10% hydrochloric acid-methanol (0.5 ml) was added. The precipitated solid was collected by filtration and recrystallized from methanol-diethyl ether to give 3-[2-[N-methyl-N-[4-(5-methyl-2-phenyl-4-oxazolylmethoxy)benzyl]amino]-4-phenyl-5-thiazolyl]propionic acid hydrochloride (270 mg, yield 46%) as colorless crystals. melting point: 106–108° C.

EXAMPLE 15

To a solution of 4-(4-chloromethylphenoxymethyl)-5-methyl-2-phenyloxazole (433 mg) and methyl 3-[4-phenyl-2-[N-(1-propyl)amino]-5-thiazolyl]propionate (400 mg) in N,N-dimethylformamide (5 ml) was added sodium hydride (60% in oil, 55.2 mg) at 0° C. and the mixture was stirred at said temperature for 1 hr. The reaction mixture was poured into water and the mixture was extracted with ethyl acetate. The ethyl acetate layer was washed with saturated brine, dried (MgSO$_4$) and concentrated. The residue was subjected to silica gel column chromatography, and methyl 3-[2-[N-[4-(5-methyl-2-phenyl-4-oxazolylmethoxy)benzyl]-N-(1-propyl)amino]-4-phenyl-5-thiazolyl]propionate (595 mg, yield 78%) was obtained as a colorless oil from a fraction eluted with ethyl acetate-hexane (1:4, volume ratio).

NMR(CDCl$_3$) δ: 0.93 (3H, t, J=7.3 Hz), 1.55–1.75 (2H, m), 2.43 (3H, s), 2.62 (2H, t, J=7.7 Hz), 3.13 (2H, t, J=7.7 Hz), 3.27–3.36 (2H, m), 3.66 (3H, s), 4.64 (2H, s), 4.98 (2H, s), 6.98 (2H, d, J=8.8 Hz), 7.22–7.48 (8H, m), 7.56–7.62 (2H, m), 7.99–8.04 (2H, m).

EXAMPLE 16

A mixture of methyl 3-[2-[N-[4-(5-methyl-2-phenyl-4-oxazolylmethoxy)benzyl]-N-(1-propyl)amino]-4-phenyl-5-thiazolyl]propionate (537 mg), lithium hydroxide hydrate (116 mg), tetrahydrofuran (6 ml), water (4 ml) and methanol (4 ml) was stirred at room temperature for 2 hrs. 1N Hydrochloric acid (2.8 ml) was added to the reaction mixture and the mixture was extracted with ethyl acetate. The ethyl acetate layer was washed with saturated brine, dried (MgSO$_4$) and concentrated. A mixture of the obtained colorless oil, 10% hydrochloric acid-methanol (3 ml) and diethyl ether (30 ml) was stirred at room temperature for 10 min. and concentrated to give 3-[2-[N-[4-(5-methyl-2-phenyl-4-oxazolylmethoxy)benzyl]-N-(1-propyl)amino]-4-phenyl-5-thiazolyl]propionic acid hydrochloride (576 mg, yield 97%) as a colorless amorphous form.

NMR(CDCl$_3$) δ: 1.01 (3H, t, J=7.3 Hz), 1.65–1.85 (2H, m), 2.55–2.63 (5H, m), 2.95 (2H, t, J=7.2 Hz), 3.60–3.80 (2H, m), 5.10 (2H, s), 5.40 (2H, s), 7.09 (2H, d, J=8.4 Hz), 7.26–7.32 (2H, m), 7.42–7.73 (8H, m), 8.38–8.45 (2H, m).

EXAMPLE 17

A mixture of ethyl 3-(5-mercapto-1H-1,2,4-triazol-3-yl)propionate (450 mg), 4-(4-chloromethylphenoxymethyl)-5-methyl-2-phenyloxazole (700 mg), potassium carbonate (370 mg) and N,N-dimethylformamide (20 ml) was stirred at room temperature for 2 hrs. The reaction mixture was poured into water and the mixture was extracted with ethyl acetate. The ethyl acetate layer was washed with water, dried (MgSO$_4$) and concentrated. The residue was subjected to silica gel column chromatography, and ethyl 3-[5-[4-(5-methyl-2-phenyl-4-oxazolylmethoxy)benzylthio]-1H-1,2,4- triazol-3-yl]propionate was obtained as crystals (600 mg, yield 56%) from a fraction eluted with ethyl acetate-hexane (3:2, volume ratio). The crystals were recrystallized from ethyl acetate-hexane. melting point: 114–115° C.

EXAMPLE 18

A mixture of ethyl 3-[5-[4-(5-methyl-2-phenyl-4-oxazolylmethoxy)benzylthio]-1H-1,2,4-triazol-3-yl]propionate (550 mg), 1N aqueous sodium hydroxide solution (3 ml), tetrahydrofuran (5 ml) and ethanol (5 ml) was stirred at room temperature for 3 hrs. The reaction mixture was poured into water, neutralized with 2N hydrochloric acid and extracted with ethyl acetate. The ethyl acetate layer was washed with water, dried (MgSO$_4$) and concentrated to give 3-[5-[4-(5-methyl-2-phenyl-4-oxazolylmethoxy)benzylthio]-1H-1,2,4-triazol-3-yl]propionic acid as crystals. Recrystallization from methanol-ethyl acetate gave colorless prism crystals (410 mg, yield 79%). melting point: 170–171° C.

EXAMPLE 19

A mixture of ethyl [2-[4-(5-methyl-2-phenyl-4-oxazolylmethoxy)phenylthio]-4-thiazolylacetate (330 mg), lithium hydroxide hydrate (89.0 mg), tetrahydrofuran (3 ml), water (2 ml) and methanol (2 ml) was stirred at room temperature for 4 hrs. 1N Hydrochloric acid (2.2 ml) was added to the reaction mixture and the mixture was extracted with ethyl acetate. The ethyl acetate layer was washed with saturated brine, dried (MgSO$_4$) and concentrated to give [2-[4-(5-methyl-2-phenyl-4-oxazolylmethoxy)phenylthio]-4-thiazolyl]acetic acid (215 mg, yield 69%) as colorless crystals. The crystals were recrystallized from ethyl acetate-hexane. melting point: 180–181° C.

EXAMPLE 20

A mixture of ethyl 3-(1-benzyl-3-hydroxy-1H-pyrazol-4-yl)propionate (900 mg), 4-(4-chloromethylphenoxymethyl)-5-methyl-2-phenyloxazole (1.06 g), potassium carbonate (690 mg) and N,N-dimethylformamide (10 ml) was stirred at 60° C. for 5 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 1N aqueous sodium hydroxide solution (5 ml), tetrahydrofuran (5 ml) and ethanol (5 ml) was stirred at room temperature for 2 hrs. 1N Hydrochloric acid (5 ml) was added to the reaction mixture and the mixture was extracted with ethyl acetate. The ethyl acetate layer was washed with saturated brine, dried (MgSO$_4$) and concentrated. The obtained colorless crystals were collected by filtration to give 3-[1-benzyl-3-[-4-(5-methyl-2-phenyl-4-oxazolylmethoxy)benzyloxy]-1H-pyrazol-4-yl]propionic acid (1.53 g, yield 89%). The crystals were recrystallized from acetone-hexane. melting point: 125–126° C.

EXAMPLE 21

A mixture of methyl (3-hydroxy-1-methyl-1H-pyrazol-4-yl)acetate (255 mg), 4-[2-(4-chloromethylphenoxy)ethyl]-5-methyl-2-phenyloxazole (492 mg), potassium carbonate (415 mg) and N,N-dimethylformamide (10 ml) was stirred at 60° C. for 8 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and methyl [1-methyl-3-[4-[2-(5-methyl-2-phenyl-4-oxazolyl)ethoxy]benzyloxy]-1H-pyrazol-4-yl]acetate (397 mg, yield 57%) was obtained as a colorless oil from a fraction eluted with ethyl acetate-hexane (1:1, volume ratio).

NMR(CDCl$_3$) δ: 2.38 (3H, s), 2.98 (2H, t, J=6.8 Hz), 3.37 (2H, s), 3.66 (3H, s), 3.72 (3H, s), 4.25 (2H, t, J=6.8 Hz), 5.12 (2H, s), 6.89 (2H, d, J=8.4 Hz), 7.17 (1H, s), 7.30–7.48 (5H, m), 7.94–8.01 (2H, m).

EXAMPLE 22

A mixture of methyl [1-methyl-3-[4-[2-(5-methyl-2-phenyl-4-oxazolyl)ethoxy]benzyloxy]-1H-pyrazol-4-ylacetate (379 mg), 1N aqueous sodium hydroxide solution (2 ml), tetrahydrofuran (4 ml) and ethanol (4 ml) was stirred at room temperature for 2 hrs. 1N Hydrochloric acid (2 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [1-methyl-3-[4-[2-(5-methyl-2-phenyl-4-oxazolyl)ethoxy]benzyloxy]-1H-pyrazol-4-yl]acetic acid (333 mg, yield 91%), which was then recrystallized from ethanol-hexane. melting point: 148–149° C.

EXAMPLE 23

A mixture of methyl 3-hydroxy-1-methyl-1H-pyrazol-4-ylacetate (245 mg), 4-(4-chloromethylphenoxymethyl)-5-methyl-2-phenyloxazole (452 mg), potassium carbonate (398 mg) and N,N-dimethylformamide (10 ml) was stirred at 60° C. for 6 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and methyl 1-methyl-3-[4-(5-methyl-2-phenyl-4-oxazolylmethoxy)benzyloxy]-1H-pyrazol-4-ylacetate (382 mg, yield 59%) was obtained as a colorless oil from a fraction eluted with ethyl acetate-hexane (2:1, volume ratio).

NMR(CDCl$_3$) δ: 2.44 (3H, s), 3.39 (2H, s), 3.67 (3H, s), 3.74 (3H, s), 5.00 (2H, s), 5.15 (2H, s), 7.02 (2H, d, J=8.8 Hz), 7.19 (1H, s), 7.29–7.52 (5H, m), 7.98–8.08 (2H, m).

EXAMPLE 24

A mixture of methyl [1-methyl-3-[4-(5-methyl-2-phenyl-4-oxazolylmethoxy)benzyloxy]-1H-pyrazol-4-yl]acetate (662 mg), 1N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [1-methyl-3-[4-(5-methyl-2-phenyl-4-oxazolylmethoxy)benzyloxy]-1H-pyrazol-4-yl]acetic acid (601 mg, yield 94%), which was then recrystallized from ethanol-hexane. melting point: 133–134° C.

EXAMPLE 25

A mixture of methyl 3-hydroxy-1-methyl-1H-pyrazol-4-ylacetate (298 mg), 5-chloromethyl-2-(5-methyl-2-phenyl-4-oxazolylmethoxy)pyridine (551 mg), potassium carbonate (484 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and methyl 1-methyl-3-[6-(5-methyl-2-phenyl-4-oxazolylmethoxy)-3-pyridylmethoxy]-1H-pyrazol-4-ylacetate (670 mg, yield 85%) was obtained as a colorless oil from a fraction eluted with ethyl acetate-hexane (2:1, volume ratio).

NMR($CDCl_3$) δ: 2.48 (3H, s), 3.37 (2H, s), 3.67 (3H, s), 3.73 (3H, s), 5.15 (2H, s), 5.31 (2H, s), 6.82 (1H, d, J=8.8 Hz), 7.18 (1H, s), 7.39–7.49 (3H, m), 7.67 (1H, dd, J=2.6, 8.8 Hz), 7.98–8.05 (2H, m), 8.23 (1H, d, J=2.6 Hz).

EXAMPLE 26

A mixture of methyl [1-methyl-3-[6-(5-methyl-2-phenyl-4-oxazolylmethoxy)-3-pyridylmethoxy]-1H-pyrazol-4-yl]acetate (668 mg), 1N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried ($MgSO_4$) and concentrated. The obtained colorless crystals were collected by filtration to give [1-methyl-3-[6-(5-methyl-2-phenyl-4-oxazolylmethoxy)-3-pyridylmethoxy]-1H-pyrazol-4-yl]acetic acid (585 mg, yield 90%), which was then recrystallized from ethanol-hexane. melting point: 139–140° C.

EXAMPLE 27

A mixture of methyl (3-hydroxy-1-methyl-1H-pyrazol-4-yl)acetate (298 mg), 4-chloromethyl-2-(5-methyl-2-phenyl-4-oxazolylmethoxy)pyridine (551 mg), potassium carbonate (484 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and methyl [1-methyl-3-[2-(5-methyl-2-phenyl-4-oxazolylmethoxy)-4-pyridylmethoxy]-1H-pyrazol-4-yl]acetate (689 mg, yield 88%) was obtained as a colorless oil from a fraction eluted with ethyl acetate-hexane (2:1, volume ratio).

NMR($CDCl_3$) δ: 2.48 (3H, s), 3.42 (2H, s), 3.69 (6H, s), 5.20 (2H, s), 5.30 (2H, s), 6.88 (1H, s), 6.92 (1H, d, J=5.2 Hz), 7.18 (1H, s), 7.39–7.49 (3H, m), 7.98–8.05 (2H, m), 8.14 (1H, d, J=5.2 Hz).

EXAMPLE 28

A mixture of methyl [1-methyl-3-[2-(5-methyl-2-phenyl-4-oxazolylmethoxy)-4-pyridylmethoxy]-1H-pyrazol-4-yl]acetate (686 mg), 1N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried ($MgSO_4$) and concentrated. The obtained colorless crystals were collected by filtration to give [1-methyl-3-[2-(5-methyl-2-phenyl-4-oxazolylmethoxy)-4-pyridylmethoxy]-1H-pyrazol-4-yl]acetic acid (471 mg, yield 71%), which was then recrystallized from acetone-hexane. melting point: 126–127° C.

EXAMPLE 29

A mixture of methyl (3-hydroxy-1-methyl-1H-pyrazol-4-yl)acetate (298 mg), 5-chloromethyl-3-(5-methyl-2-phenyl-4-oxazolylmethoxy)isoxazole (533 mg), potassium carbonate (484 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and methyl [1-methyl-3-[3-(5-methyl-2-phenyl-4-oxazolylmethoxy)-5-isoxazolylmethoxy]-1H-pyrazol-4-yl]acetate (701 mg, yield 91%) was obtained as a colorless oil from a fraction eluted with ethyl acetate-hexane (2:1, volume ratio).

NMR($CDCl_3$) δ: 2.48 (3H, s), 3.37 (2H, s), 3.69 (3H, s), 3.70 (3H, s), 5.19 (2H, s), 5.20 (2H, s), 6.01 (1H, s), 7.17 (1H, s), 7.42–7.49 (3H, m), 7.98–8.04 (2H, m).

EXAMPLE 30

A mixture of methyl [1-methyl-3-[3-(5-methyl-2-phenyl-4-oxazolylmethoxy)-5-isoxazolylmethoxy]-1H-pyrazol-4-yl]acetate (701 mg), 1N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried ($MgSO_4$) and concentrated. The obtained colorless crystals were collected by filtration to give [1-methyl-3-[3-(5-methyl-2-phenyl-4-oxazolylmethoxy)-5-isoxazolylmethoxy]-1H-pyrazol-4-yl]acetic acid (547 mg, yield 81%), which was then recrystallized from acetone-hexane. melting point: 149–150° C.

EXAMPLE 31

A mixture of methyl (3-hydroxy-1-methyl-1H-pyrazol-4-yl)acetate (298 mg), 2-(5-chloromethyl-3-isoxazolyloxymethyl)quinoline (481 mg), potassium carbonate (484 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and methyl [1-methyl-3-[3-(2-quinolylmethoxy)-5-isoxazolylmethoxy]-1H-pyrazol-4-yl]acetate (676 mg, yield 95%) was obtained as a colorless oil from a fraction eluted with ethyl acetate-hexane (2:1, volume ratio).

NMR($CDCl_3$) δ: 3.38 (2H, s), 3.69 (3H, s), 3.71 (3H, s), 5.21 (2H, s), 5.57 (2H, s), 6.10 (1H, s), 7.18 (1H, s), 7.55 (1H, ddd, J=1.0, 6.8, 8.2 Hz), 7.61 (1H, d, J=8.8 Hz), 7.74 (1H, ddd, J=1.6, 6.8, 8.4 Hz), 7.84 (1H, dd, J=1.6, 8.2 Hz), 8.08–8.14 (1H, m), 8.21 (1H, d, J=8.8 Hz).

EXAMPLE 32

A mixture of methyl [1-methyl-3-[3-(2-quinolylmethoxy)-5-isoxazolylmethoxy]-1H-pyrazol-4-yl]acetate (674 mg), 1N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [1-methyl-3-[3-(2-quinolylmethoxy)-5-isoxazolylmethoxy]-1H-pyrazol-4-yl]acetic acid (532 mg, yield 82%), which was then recrystallized from tetrahydrofuran-hexane. melting point: 124–125° C.

EXAMPLE 33

A mixture of methyl (3-hydroxy-1-methyl-1H-pyrazol-4-yl)acetate (255 mg), 5-chloromethyl-2-(2-phenyl-4-thiazolylmethoxy)pyridine (475 mg), potassium carbonate (415 mg) and N,N-dimethylformamide (10 ml) was stirred at 60° C. for 5 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and methyl [1-methyl-3-[6-(2-phenyl-4-thiazolylmethoxy)-3-pyridylmethoxy]-1H-pyrazol-4-yl]acetate (581 mg, yield 86%) was obtained as colorless crystals from a fraction eluted with ethyl acetate-hexane (2:1, volume ratio). The crystals were recrystallized from ethyl acetate-hexane. melting point: 85–86° C.

EXAMPLE 34

A mixture of methyl [1-methyl-3-[6-(2-phenyl-4-thiazolylmethoxy)-3-pyridylmethoxy]-1H-pyrazol-4-yl]acetate (496 mg), 1N aqueous sodium hydroxide solution (3 ml), tetrahydrofuran (6 ml) and ethanol (6 ml) was stirred at room temperature for 3 hrs. 1N Hydrochloric acid (3 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [1-methyl-3-[6-(2-phenyl-4-thiazolylmethoxy)-3-pyridylmethoxy]-1H-pyrazol-4-yl]acetic acid (432 mg, yield 90%), which was then recrystallized from ethanol-hexane. melting point: 156–157° C.

EXAMPLE 35

A mixture of methyl (3-hydroxy-1-methyl-1H-pyrazol-4-yl)acetate (255 mg), 5-chloromethyl-2-(5-methyl-2-phenyl-4-thiazolylmethoxy)pyridine (496 mg), potassium carbonate (415 mg) and N,N-dimethylformamide (10 ml) was stirred at 60° C. for 5 hrs. The reaction mixture was poured into water and the mixture was extracted with ethyl acetate. The ethyl acetate layer was washed with saturated brine, dried (MgSO$_4$) and concentrated. The residue was subjected to silica gel column. chromatography, and methyl [1-methyl-3-[6-(5-methyl-2-phenyl-4-thiazolylmethoxy)-3-pyridylmethoxy]-1H-pyrazol-4-yl]acetate (501 mg, yield 72%) was obtained as a colorless oil from a fraction eluted with ethyl acetate-hexane (2:1, volume ratio).

NMR(CDCl$_3$) δ: 2.57 (3H, s), 3.37 (2H, s), 3.68 (3H, s), 3.73 (3H, s), 5.16 (2H, s), 5.45 (2H, s), 6.83 (1H, d, J=8.8 Hz), 7.19 (1H, s), 7.37–7.47 (3H, m), 7.68 (1H, dd, J=2.2, 8.8 Hz), 7.86–7.93 (2H, m), 8.24 (1H, d, J=2.2 Hz).

EXAMPLE 36

A mixture of methyl [1-methyl-3-[6-(5-methyl-2-phenyl-4-thiazolylmethoxy)-3-pyridylmethoxy]-1H-pyrazol-4-yl] acetate (497 mg), 1N aqueous sodium hydroxide solution (2 ml), tetrahydrofuran (4 ml) and ethanol (4 ml) was stirred at room temperature for 2 hrs. 1N Hydrochloric acid (2 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [1-methyl-3-[6-(5-methyl-2-phenyl-4-thiazolylmethoxy)-3-pyridylmethoxy]-1H-pyrazol-4-yl]acetic acid (411 mg, yield 85%), which was then recrystallized from ethanol-hexane. melting point: 140–141° C.

EXAMPLE 37

A mixture of methyl (3-hydroxy-1-methyl-1H-pyrazol-4-yl)acetate (298 mg), 5-chloromethyl-2-[2-(2-furyl)-5-methyl-4-oxazolylmethoxy]pyridine (533 mg), potassium carbonate (484 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and methyl [3-[6-[2-(2-furyl)-5-methyl-4-oxazolylmethoxy]-3-pyridylmethoxy]-1-methyl-1H-pyrazol-4-yl]acetate (623 mg, yield 81%) was obtained as a colorless oil from a fraction eluted with ethyl acetate-hexane (2:1, volume ratio).

NMR(CDCl$_3$) δ: 2.46 (3H, s), 3.37 (2H, s), 3.67 (3H, s), 3.73 (3H, s), 5.14 (2H, s), 5.28 (2H, s), 6.51 (1H, dd, J=1.6, 3.6 Hz), 6.80 (1H, d, J=8.6 Hz), 6.98 (1H, d, J=3.6 Hz), 7.18 (1H, s), 7.52 (1H, d, J=1.6 Hz), 7.67 (1H, dd, J=2.4, 8.6 Hz), 8.22 (1H, d, J=2.4 Hz).

EXAMPLE 38

A mixture of methyl [3-[6-[2-(2-furyl)-5-methyl-4-oxazolylmethoxy]-3-pyridylmethoxy]-1-methyl-1H-pyrazol-4-yl]acetate (623 mg), 1N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [3-[6-[2-(2-furyl)-5-methyl-4-oxazolylmethoxy]-3-pyridylmethoxy]-1-methyl-1H-pyrazol-4-yl] acetic acid (580 mg, yield 96%), which was then recrystallized from ethanol-hexane. melting point: 155–156° C.

EXAMPLE 39

A mixture of ethyl (1-benzyl-3-hydroxy-1H-pyrazol-4-yl) acetate (390 mg), 5-chloromethyl-2-(5-methyl-2-phenyl-4-oxazolylmethoxy)pyridine (472 mg), potassium carbonate (414 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and ethyl [1-benzyl-3-[6-(5-methyl-2-phenyl-4-oxazolylmethoxy)-3-pyridylmethoxy]-1H-pyrazol-4-yl]acetate (649 mg, yield 80%) was obtained as a colorless oil from a fraction eluted with ethyl acetate-hexane (1:1, volume ratio).

NMR(CDCl$_3$) δ: 1.22 (3H, t, J=7.2 Hz), 2.48 (3H, s), 3.35 (2H, s), 4.12 (2H, q, J=7.2 Hz), 5.12 (2H, s), 5.17 (2H, s), 5.30 (2H, s), 6.79 (1H, d, J=8.4 Hz), 7.17–7.47 (9H, m), 7.66 (1H, dd, J=2.6, 8.4 Hz), 7.98–8.08 (2H, m), 8.22 (1H, d, J=2.6 Hz).

EXAMPLE 40

A mixture of ethyl [1-benzyl-3-[6-(5-methyl-2-phenyl-4-oxazolylmethoxy)-3-pyridylmethoxy]-1H-pyrazol-4-yl]acetate (648 mg), 1 N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried ($MgSO_4$) and concentrated. The obtained colorless crystals were collected by filtration to give [1-benzyl-3-[6-(5-methyl-2-phenyl-4-oxazolylmethoxy)-3-pyridylmethoxy]-1H-pyrazol-4-yl]acetic acid (539 mg, yield 88%), which was then recrystallized from ethyl acetate-hexane. melting point: 87–88° C.

EXAMPLE 41

A mixture of methyl (3-hydroxy-1-methyl-1H-pyrazol-4-yl)acetate (340 mg), 4-(4-chloromethyl-2-methoxyphenoxymethyl)-5-methyl-2-phenyloxazole (687 mg), potassium carbonate (553 mg) and N,N-dimethylformamide (10 ml) was stirred at 60° C. for 5 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and methyl [3-[3-methoxy-4-(5-methyl-2-phenyl-4-oxazolylmethoxy)benzyloxy]-1-methyl-1H-pyrazol-4-yl]acetate (546 mg, yield 57%) was obtained as a colorless oil from a fraction eluted with ethyl acetate-hexane (2:1, volume ratio).

NMR($CDCl_3$) δ: 2.42 (3H, s), 3.40 (2H, s), 3.67 (3H, s), 3.74 (3H, s), 3.89 (3H, s), 5.06 (2H, s), 5.15 (2H, s), 6.95 (1H, dd, J=2.0, 8.6 Hz), 7.01 (1H, d, J=2.0 Hz), 7.03 (1H, d, J=8.6 Hz), 7.19 (1H, s), 7.40–7.50 (3H, m), 7.97–8.06 (2H, m).

EXAMPLE 42

A mixture of methyl [3-[3-methoxy-4-(5-methyl-2-phenyl-4-oxazolylmethoxy)benzyloxy]-1-methyl-1H-pyrazol-4-yl]acetate (544 mg), 1N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried ($MgSO_4$) and concentrated. The obtained colorless crystals were collected by filtration to give [3-[3-methoxy-4-(5-methyl-2-phenyl-4-oxazolylmethoxy)benzyloxy]-1-methyl-1H-pyrazol-4-yl]acetic acid (482 mg, yield 91%), which was then recrystallized from acetone-hexane. melting point: 153–154° C.

EXAMPLE 43

A mixture of ethyl (1-benzyl-3-hydroxy-1H-pyrazol-4-yl)acetate (521 mg), 4-(4-chloromethylphenoxymethyl)-5-methyl-2-phenyloxazole (628 mg), potassium carbonate (553 mg) and N,N-dimethylformamide (10 ml) was stirred at 60° C. for 5 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and ethyl [1-benzyl-3-[4-(5-methyl-2-phenyl-4-oxazolylmethoxy)benzyloxy]-1H-pyrazol-4-yl]acetate (731 mg, yield 68%) was obtained as a colorless oil from a fraction eluted with ethyl acetate-hexane (1:3, volume ratio).

NMR($CDCl_3$) δ: 1.22 (3H, t, J=7.0 Hz), 2.44 (3H, s), 3.37 (2H, s), 4.12 (2H, q, J=7.0 Hz), 5.00 (2H, s), 5.12 (2H, s), 5.17 (2H, s), 6.96–7.03 (2H, m), 7.17–7.50 (11H, m), 7.98–8.06 (2H, m).

EXAMPLE 44

A mixture of ethyl [1-benzyl-3-[4-(5-methyl-2-phenyl-4-oxazolylmethoxy)benzyloxy]-1H-pyrazol-4-yl]acetate (731 mg), 1N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried ($MgSO_4$) and concentrated. The obtained colorless crystals were collected by filtration to give [1-benzyl-3-[4-(5-methyl-2-phenyl-4-oxazolylmethoxy)benzyloxy]-1H-pyrazol-4-yl]acetic acid (580 mg, yield 84%), which was then recrystallized from acetone-hexane. melting point: 91–92° C.

EXAMPLE 45

A mixture of ethyl (1-benzyl-3-hydroxy-1H-pyrazol-4-yl)acetate (521 mg), 4-(4-chloromethyl-2-methoxyphenoxymethyl)-5-methyl-2-phenyloxazole (687 mg), potassium carbonate (553 mg) and N,N-dimethylformamide (10 ml) was stirred at 60° C. for 5 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and ethyl [1-benzyl-3-[3-methoxy-4-(5-methyl-2-phenyl-4-oxazolylmethoxy)benzyloxy]-1H-pyrazol-4-yl]acetate (632 mg, yield 56%) was obtained as colorless crystals from a fraction eluted with ethyl acetate-hexane (1:2, volume ratio). The crystals were recrystallized from ethyl acetate-hexane. melting point: 86–87° C.

EXAMPLE 46

A mixture of ethyl [1-benzyl-3-[3-methoxy-4-(5-methyl-2-phenyl-4-oxazolylmethoxy)benzyloxy]-1H-pyrazol-4-yl]acetate (539 mg), 1N aqueous sodium hydroxide solution (2 ml), tetrahydrofuran (4 ml) and ethanol (4 ml) was stirred at room temperature for 2 hrs. 1N Hydrochloric acid (2 ml) was added to the reaction mixture and the mixture was extracted with ethyl acetate. The ethyl acetate layer was washed with saturated brine, dried ($MgSO_4$) and concentrated. The obtained colorless crystals were collected by filtration to give [1-benzyl-3-[3-methoxy-4-(5-methyl-2-phenyl-4-oxazolylmethoxy)benzyloxy]-1H-pyrazol-4-yl]acetic acid (423 mg, yield 83%). The crystals were recrystallized from ethanol-hexane. melting point: 99–100° C.

EXAMPLE 47

A mixture of ethyl 3-(1-benzyl-3-hydroxy-1H-pyrazol-4-yl)propionate (411 mg), 5-chloromethyl-2-(5-methyl-2-phenyl-4-oxazolylmethoxy)pyridine (472 mg), potassium carbonate (414 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and ethyl 3-[1-benzyl-3-[6-(5-methyl-2-phenyl-4-oxazolylmethoxy)-3-pyridylmethoxy]-1H-pyrazol-4-yl]propionate (748 mg, yield 91%) was obtained as a colorless oil from a fraction eluted with ethyl acetate-hexane (1:2, volume ratio).

NMR(CDCl$_3$) δ: 1.19 (3H, t, J=7.2 Hz), 2.45–2.53 (5H, m), 2.60–2.68 (2H, m), 4.07 (2H, q, J=7.2 Hz), 5.08 (2H, s), 5.16 (2H, s), 5.31 (2H, s), 6.81 (1H, d, J=8.4 Hz), 7.00 (1H, s), 7.14–7.22 (2H, m), 7.28–7.46 (6H, m), 7.68 (1H, dd, J=2.2, 8.4 Hz), 7.98–8.07 (2H, m), 8.24 (1H, d, J=2.2 Hz).

EXAMPLE 48

A mixture of ethyl 3-[1-benzyl-3-[6-(5-methyl-2-phenyl-4-oxazolylmethoxy)-3-pyridylmethoxy]-1H-pyrazol-4-yl]propionate (746 mg), 1N aqueous sodium hydroxide solution (3 ml), tetrahydrofuran (6 ml) and ethanol (6 ml) was stirred at room temperature. 1N Hydrochloric acid (3 ml) was added to the reaction mixture and the mixture was extracted with ethyl acetate. The ethyl acetate layer was washed with saturated brine, dried (MgSO$_4$) and concentrated. The obtained colorless crystals were collected by filtration to give 3-[1-benzyl-3-[6-(5-methyl-2-phenyl-4-oxazolylmethoxy)-3-pyridylmethoxy]-1H-pyrazol-4-yl]propionic acid (639 mg, yield 90%), which was then recrystallized from acetone-hexane. melting point: 130–131° C.

EXAMPLE 49

A mixture of methyl (3-hydroxy-1-phenyl-1H-pyrazol-4-yl)acetate (464 mg), 4-(4-chloromethylphenoxymethyl)-5-methyl-2-phenyloxazole (628 mg), potassium carbonate (553 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried (MgSO) and concentrated. The residue was subjected to silica gel column chromatography, and methyl [3-[4-(5-methyl-2-phenyl-4-oxazolylmethoxy)benzyloxy]-1-phenyl-1H-pyrazol-4-yl]acetate (767 mg, yield 75%) was obtained as colorless crystals from a fraction eluted with ethylacetate. The crystals were recrystallized from ethyl acetate-hexane. melting point: 113–114° C.

EXAMPLE 50

A mixture of methyl [3-[4-(5-methyl-2-phenyl-4-oxazolylmethoxy)benzyloxy]-1-phenyl-1H-pyrazol-4-yl]acetate (662 mg), 1N aqueous sodium hydroxide solution (3 ml), tetrahydrofuran (6 ml) and ethanol (6 ml) was stirred at room temperature for 1 hr. 1N Hydrochloric acid (3 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [3-[4-(5-methyl-2-phenyl-4-oxazolylmethoxy)benzyloxy]-1-phenyl-1H-pyrazol-4-yl]acetic acid (583 mg, yield 91%), which was then recrystallized from acetone-hexane. melting point: 151–152° C.

EXAMPLE 51

A mixture of methyl (3-hydroxy-1-phenyl-1H-pyrazol-4-yl)acetate (406 mg), 4-(4-chloromethyl-2-methoxyphenoxymethyl)-5-methyl-2-phenyloxazole (551 mg), potassium carbonate (484 mg) and N,N-dimethylformamide (10 ml) was stirred at 60° C. for 4 hrs. The reaction mixture was poured into water and the mixture was extracted with ethyl acetate. The ethyl acetate-layer was washed with saturated brine, dried (MgSO$_4$) and concentrated. The obtained colorless crystals were collected by filtration to give methyl [3-[3-methoxy-4-(5-methyl-2-phenyl-4-oxazolylmethoxy)benzyloxy]-1-phenyl-1H-pyrazol-4-yl]acetate (595 mg, yield 55%), which was then recrystallized from ethyl acetate-hexane. melting point: 107–108° C.

EXAMPLE 52

A mixture of methyl [3-[3-methoxy-4-(5-methyl-2-phenyl-4-oxazolylmethoxy)benzyloxy]-1-phenyl-1H-pyrazol-4-yl]acetate (496 mg), 1 N aqueous sodium hydroxide solution (2 ml), tetrahydrofuran (4 ml) and ethanol (4 ml) was stirred at room temperature for 1 hr. 1N Hydrochloric acid (2 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [3-[3-methoxy-4-(5-methyl-2-phenyl-4-oxazolylmethoxy)benzyloxy]-1-phenyl-1H-pyrazol-4-yl]acetic acid (438 mg, yield 90%), which was then recrystallized from ethanol-water. melting point: 147–148° C.

EXAMPLE 53

A mixture of methyl (3-hydroxy-1-phenyl-1H-pyrazol-4-yl)acetate (406 mg), 5-chloromethyl-2-(5-methyl-2-phenyl-4-oxazolylmethoxy)pyridine (551 mg), potassium carbonate (484 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried (MgSO$_4$) and concentrated. The obtained colorless crystals were collected by filtration to give methyl [3-[6-(5-methyl-2-phenyl-4-oxazolylmethoxy)-3-pyridylmethoxy]-1-phenyl-1H-pyrazol-4-yl]acetate (690 mg, yield 77%), which was then recrystallized from ethyl acetate-hexane. melting point: 96–97° C.

EXAMPLE 54

A mixture of methyl [3-[6-(5-methyl-2-phenyl-4-oxazolylmethoxy)-3-pyridylmethoxy]-1-phenyl-1H-pyrazol-4-yl]acetate (587 mg), 1N aqueous sodium hydroxide solution (3 ml), tetrahydrofuran (6 ml) and ethanol (6 ml) was stirred at room temperature for 1 hr. 1N Hydrochloric acid (3 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [3-[6-(5-methyl-2-phenyl-4-oxazolylmethoxy)-3-pyridylmethoxy]-1-phenyl-1H-pyrazol-4-yl]acetic acid (502 mg, yield 88%), which was then recrystallized from ethanol-hexane. melting point: 164–165° C.

EXAMPLE 55

A mixture of ethyl 3-(3-hydroxy-1-phenyl-1H-pyrazol-4-yl)propionate (0.40 g), 4-(4-chloromethyl-2-methoxyphenoxymethyl)-2-(2-furyl)-5-methyloxazole (0.57 g), potassium carbonate (276 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and ethyl 3-[3-[4-[2-(2-furyl)-5-methyl-4-oxazolylmethoxy]-3-methoxybenzyloxy]-1-phenyl-1H-pyrazol-4-yl]propionate (420 mg, yield 44%) was obtained as colorless crystals from a fraction eluted with ethyl acetate-hexane (1:2, volume ratio). The crystals were recrystallized from ethyl acetate-hexane. melting point: 97–98° C.

EXAMPLE 56

A mixture of ethyl 3-[3-[4-[2-(2-furyl)-5-methyl-4-oxazolylmethoxy]-3-methoxybenzyloxy]-1-phenyl-1H-pyrazol-4-yl]propionate (340 mg), 1N aqueous sodium hydroxide solution (3 ml), tetrahydrofuran (6 ml) and ethanol (6 ml) was stirred at room temperature for 2 hrs. 1N Hydrochloric acid (3 ml) was added to the reaction mixture and the mixture was extracted with ethyl acetate. The ethyl acetate layer was washed with saturated brine, dried ($MgSO_4$) and concentrated. The obtained colorless crystals were collected by filtration to give 3-[3-[4-[2-(2-furyl)-5-methyl-4-oxazolylmethoxy]-3-methoxybenzyloxy]-1-phenyl-1H-pyrazol-4-yl]propionic acid (300 mg, yield 94%), which was then recrystallized from ethyl acetate-hexane. melting point: 161–162° C.

EXAMPLE 57

A mixture of methyl (2-mercapto-4-methylthiazol-5-yl)acetate (385 mg), 4-(4-chloromethylphenoxymethyl)-5-methyl-2-phenyloxazole (600 mg), potassium carbonate (400 mg) and N,N-dimethylformamide (20 ml) was stirred at room temperature for 2 hrs. The reaction mixture was poured into water and the mixture was extracted with ethyl acetate. The ethyl acetate layer was washed with water, dried ($MgSO_4$) and concentrated. The residue was subjected to silica gel column chromatography, and methyl [4-methyl-2-[4-(5-methyl-2-phenyl-4-oxazolylmethoxy)benzylthio]thiazol-5-yl]acetate (750 mg, yield 82%) was obtained as an oil from a fraction eluted with ethyl acetate-hexane (1:3, volume ratio).

NMR($CDCl_3$) δ: 2.33 (3H, s), 2.43 (3H, s), 3.69 (2H, s), 3.73 (3H, s), 4.33 (2H, s), 4.98 (2H, s), 6.96 (2H, d, J=8.7 Hz), 7.30 (2H, d, J=8.7 Hz), 7.4–7.5(3H, m), 7.95–8.05 (2H, m).

EXAMPLE 58

A mixture of methyl [4-methyl-2-[4-(5-methyl-2-phenyl-4-oxazolylmethoxy)benzylthio]thiazol-5-yl]acetate (740 mg), 1N aqueous sodium hydroxide solution (5 ml), tetrahydrofuran (5 ml) and methanol (5 ml) was stirred at room temperature for 2 hrs. The reaction mixture was poured into water, neutralized with 2N hydrochloric acid and the precipitated crystals (705 mg, 98%) of [4-methyl-2-[4-(5-methyl-2-phenyl-4-oxazolylmethoxy)benzylthio]thiazol-5-yl]acetic acid were collected by filtration. Recrystallization from tetrahydrofuran-ethyl acetate gave colorless prism crystals. melting point: 192–193° C.

EXAMPLE 59

A mixture of methyl (2-mercapto-4-methylthiazol-5-yl)acetate (385 mg), 4-(3-chloromethylphenoxymethyl)-5-methyl-2-phenyloxazole (600 mg), potassium carbonate (400 mg) and N,N-dimethylformamide (20 ml) was stirred at room temperature for 2 hrs. The reaction mixture was poured into water and the mixture was extracted with ethyl acetate. The ethyl acetate layer was washed with water, dried ($MgSO_4$) and concentrated. The residue was subjected to silica gel column chromatography, and methyl [4-methyl-2-[3-(5-methyl-2-phenyl-4-oxazolylmethoxy)benzylthio]thiazol-5-yl]acetate (665 mg, yield 72%) was obtained as an oil from a fraction eluted with ethyl acetate-hexane (1:3 volume ratio).

NMR($CDCl_3$) δ: 2.33 (3H, s), 2.44 (3H, s), 3.68 (2H, s), 3.72 (3H, s), 4.35 (2H, s), 4.97 (2H, s), 6.9–7.1(3H, m), 7.22 (1H, d, J=8.1 Hz), 7.4–7.5(3H, m), 8.0–8.05 (2H, m).

EXAMPLE 60

A mixture of methyl [4-methyl-2-[3-(5-methyl-2-phenyl-4-oxazolylmethoxy)benzylthio]thiazol-5-yl]acetate (660 mg), 1N aqueous sodium hydroxide solution (5 ml), tetrahydrofuran (5 ml) and methanol (5 ml) was stirred at room temperature for 2 hrs. The reaction mixture was poured into water, neutralized with 2N hydrochloric acid and extracted with 5% methanol-ethyl acetate. The organic layer was washed with water, dried ($MgSO_4$) and concentrated. The precipitated crystals (620 mg, 97%) of [4-methyl-2-[3-(5-methyl-2-phenyl-4-oxazolylmethoxy)benzylthio]thiazol-5-yl]acetic acid were collected by filtration with ethyl acetate-isopropyl ether. Recrystallization from methanol-ethyl acetate gave colorless prism crystals. melting point: 154–155° C.

EXAMPLE 61

To a mixture of 4-(5-methyl-2-phenyl-4-oxazolylmethoxy)benzoic acid (2.00 g), N,N-dimethylformamide (0.1 ml) and tetrahydrofuran (5 ml) was slowly added oxalyl chloride (0.21 ml) and the mixture was stirred at room temperature for 30 min. The reaction solvent was removed under reduced pressure and the obtained residue was dissolved in N,N-dimethylacetamide (10 ml). Methyl 3-(2-amino-4-phenyl-5-thiazolyl)propionate (425 mg) was added and the mixture was stirred at room temperature for 2 hrs. The reaction mixture was poured into water and the mixture was extracted with ethyl acetate. The organic layer was washed with saturated brine, dried over anhydrous magnesium sulfate, and concentrated. The obtained residue was subjected to silica gel column chromatography, and methyl 3-[2-[4-(5-methyl-2-phenyl-4-oxazolylmethoxy)benzamide]-4-phenyl-5-thiazolyl]propionate (609 mg, yield 68%) was obtained as colorless crystals from a fraction eluted with ethyl acetate-hexane (1:1, volume ratio). The crystals were recrystallized from ethyl acetate-hexane. melting point: 165–166° C.

EXAMPLE 62

A mixture of methyl 3-[2-[4-(5-methyl-2-phenyl-4-oxazolylmethoxy)benzamide]-4-phenyl-5-thiazolyl]propionate (440 mg), lithium hydroxide hydrate (100 mg), tetrahydrofuran (6 ml), water (4 ml) and methanol (4 ml) was stirred at room temperature for 2 hrs. 1N Hydrochloric acid (2.4 ml) was added to the reaction mixture and the mixture was extracted with ethyl acetate. The ethyl acetate layer was washed with saturated brine, dried ($MgSO_4$) and concentrated to give 3-[2-[4-(5-methyl-2-phenyl-4-oxazolylmethoxy)benzamide]-4-phenyl-5-thiazolyl]propionic acid (370 mg, yield 86%) as colorless crystals. The crystals were recrystallized from ethyl acetate. melting point: 244–245° C.

EXAMPLE 63

A mixture of ethyl 3-[2-amino-4-(5,6,7,8-tetrahydro-2-naphthyl)-5-thiazolyl]propionate (270 mg), [4-[2-(2-furyl)-5-methyl-4-oxazolylmethoxy]phenyl]acetic acid (250 mg), WSC (170 mg), HOBt (135 mg) and N,N-dimethylformamide (10 ml) was stirred for 3 days. The reaction mixture was poured into water, neutralized with 2N hydrochloric acid and extracted with ethyl acetate. The ethyl acetate layer was washed with water, dried ($MgSO_4$) and concentrated. The residue was dissolved in ethanol (9 ml)-tetrahydrofuran (1 ml) and 1N aqueous sodium hydroxide solution (2 ml) was added at 0° C. The mixture was stirred at room temperature for 2 hrs. The reaction mixture was poured into water, neutralized with 2N hydrochloric acid and extracted with ethyl acetate. The ethyl acetate layer was washed with water, dried ($MgSO_4$) and concentrated. The residue was subjected to silica gel column chromatography, and 3-[2-[[4-[2-(2-furyl)-5-methyl-4-oxazolylmethoxy]phenyl]acetylamino]-4-(5,6,7,8-tetrahydro-2-naphthyl)-5-thiazolyl]propionic acid (270 mg, 57%) was obtained as an amorphous oil from a fraction eluted with acetone-hexane (3:2, volume ratio).

NMR($CDCl_3$) δ: 1.7–1.9(4H, m), 2.40 (3H, s), 2.6–2.8 (6H, m), 3.16 (2H, t, J=7.5 Hz), 3.66 (2H, s), 4.96 (2H, s), 6.51 (1H, dd, J=3.5, 1.5 Hz), 6.9–7.2(6H, m), 7.21 (2H, d, J=8.5 Hz), 7.5–7.55 (1H, m).

EXAMPLE 64

A mixture of [5-[2-[4-(5-methyl-2-phenyl-4-oxazolyl) methoxyphenyl]ethyl]-2-phenyl-4-oxazolyl]acetonitrile (450 mg), 2N aqueous sodium hydroxide solution (5 ml), tetrahydrofuran (1 ml) and ethanol (5 ml) was refluxed for 5 hrs. 1N Hydrochloric acid (10 ml) was added to the reaction mixture and the mixture was extracted with ethyl acetate. The ethyl acetate layer was washed with saturated brine, dried ($MgSO_4$) and concentrated. The obtained colorless crystals were collected by filtration to give [5-[2-[4-(5-methyl-2-phenyl-4-oxazolyl)methoxyphenyl]ethyl]-2-phenyl-4-oxazolyl]acetic acid (440 mg, yield 94%), which was then recrystallized from ethyl acetate-hexane. melting point: 180–181° C.

EXAMPLE 65

A mixture of ethyl 2-ethoxycarbonyl-3-[5-[2-[4-(5-methyl-2-phenyl-4-oxazolyl)methoxyphenyl]ethyl]-2-phenyl-4-oxazolyl]propionate (530 mg), 4N aqueous potassium hydroxide solution (3 ml) and ethanol (5 ml) was refluxed for 1 hr. 1N Hydrochloric acid (15 ml) was added and the mixture was extracted with ethyl acetate. The ethyl acetate layer was washed with saturated brine, dried ($MgSO_4$) and concentrated.

The obtained residue was dissolved in pyridine (5 ml) and the mixture was stirred at 110° C. for 2 hrs., and concentrated. The obtained residue was dissolved in ethyl acetate, washed successively with dilute hydrochloric acid and saturated brine, dried ($MgSO_4$) and concentrated. The obtained colorless crystals were collected by filtration to give 3-[5-[2-[4-(5-methyl-2-phenyl-4-oxazolyl)methoxyphenyl] ethyl]-2-phenyl-4-oxazolyl]propionic acid (400 mg, yield 91%). The crystals were recrystallized from ethyl acetate-hexane. melting point: 110–111° C.

EXAMPLE 66

A mixture of methyl 4-[4-[2-(2-furyl)-5-methyl-4-oxazolylmethoxy]phenyl]acetamide-5-oxo-5-phenylpentanoate (900 mg), phosphoric oxychloride (900 mg) and toluene (7 ml) was refluxed for 0.5 hr. After cooling, cold saturated aqueous sodium hydrogen carbonate was added to the reaction mixture and the mixture was extracted with ethyl acetate. The ethyl acetate layer was washed with saturated brine, dried ($MgSO_4$) and concentrated. The residue was subjected to silica gel column chromatography, and methyl 3-[2-[4-[2-(2-furyl)-5-methyl-4-oxazolylmethoxy] benzyl]-5-phenyl-4-oxazolyl]propionate (557 mg, yield 64%) was obtained as a pale-yellow oil from a fraction eluted with ethyl acetate-hexane (1:1, volume ratio).

NMR($CDCl_3$) δ: 2.41 (3H, s), 2.73–2.82 (2H, m), 3.02–3.11 (2H, m), 3.65 (3H, s), 4.06 (2H, s), 4.97 (2H, s), 6.50–6.54 (1H, m), 6.93–7.00 (3H, m), 7.23–7.46 (5H, m), 7.52–7.60 (3H, m).

EXAMPLE 67

A mixture of methyl 3-[2-[4-[2-(2-furyl)-5-methyl-4-oxazolylmethoxy]benzyl]-5-phenyl-4-oxazolyl]propionate (489 mg), lithium hydroxide hydrate (127 mg), tetrahydrofuran (6 ml), water (4 ml) and methanol (4 ml) was stirred at room temperature for 2 hrs. 1N Hydrochloric acid (3.1 ml) was added to the reaction mixture and the mixture was extracted with ethyl acetate. The ethyl acetate layer was washed with saturated brine, dried ($MgSO_4$) and concentrated to give 3-[2-[4-[2-(2-furyl)-5-methyl-4-oxazolylmethoxy]benzyl]-5-phenyl-4-oxazolyl]propionic acid (448 mg, yield 94%) as colorless crystals. The crystals were recrystallized from ethyl acetate-hexane. melting point: 154–155° C.

EXAMPLE 68

A mixture of methyl 4-[4-[2-(2-furyl)-5-methyl-4-oxazolylmethoxy]phenyl]acetoxy-5-oxo-5-phenylpentanoate (1.49 g), ammonium acetate (777 mg) and acetic acid (5 ml) was refluxed for 3 hrs. After cooling, ethyl acetate was added to the reaction mixture. The obtained ethyl acetate solution was washed with saturated aqueous sodium hydrogen carbonate and then saturated brine, dried ($MgSO_4$) and concentrated. The residue was subjected to silica gel column chromatography, and methyl 3-[2-[4-[2-(2-furyl)-5-methyl-4-oxazolylmethoxy]benzyl]-4-phenyl-5-oxazolyl]propionate (1.11 g, yield 77%) was obtained as a colorless oil from a fraction eluted with ethyl acetate-hexane (2:3, volume ratio).

NMR($CDCl_3$) δ: 2.41 (3H, s), 2.64–2.73 (2H, m), 3.14–3.23 (2H, m), 3.64 (3H, s), 4.06 (2H, s), 4.97 (2H, s), 6.50–6.54 (1H, m), 6.93–6.99 (3H, m), 7.17–7.46 (5H, m), 7.52–7.55 (1H, m), 7.60–7.66 (2H, m).

EXAMPLE 69

A mixture of methyl 3-[2-[4-[2-(2-furyl)-5-methyl-4-oxazolylmethoxy]benzyl]-4-phenyl-5-oxazolyl]propionate (1.01 g), lithium hydroxide hydrate (255 mg), tetrahydrofuran (6 ml), water (4 ml) and methanol (4 ml) was stirred at room temperature for 1 hr. 1N Hydrochloric acid (6.1 ml) was added to the reaction mixture and the mixture was extracted with ethyl acetate. The ethyl acetate layer was washed with saturated brine, dried ($MgSO_4$) and concentrated to give 3-[2-[4-[2-(2-furyl)-5-methyl-4-oxazolylmethoxy]benzyl]-4-phenyl-5-oxazolyl]propionic acid (881 mg, yield 92%) as colorless crystals. The crystals were recrystallized from ethyl acetate-hexane. melting point: 74–76° C.

EXAMPLE 70

A mixture of (2-chloro-4-thiazolyl)ethyl acetate (440 mg), 4-hydroxythiophenol (540 mg), potassium carbonate (591 mg) and N,N-dimethylformamide (4 ml) was stirred at room temperature for 15 hrs. The reaction mixture was poured into water and the mixture was extracted with ethyl acetate. The organic layer was washed successively with dilute hydrochloric acid and saturated brine, dried over anhydrous magnesium sulfate, and concentrated. A mixture of the obtained residue, 4-chloromethyl-5-methyl-2-phenyloxazole (1.66 g), potassium carbonate (1.66 g) and N,N-dimethylformamide (5 ml) was stirred at 50° C. for 2 hrs. The reaction mixture was poured into water and the mixture was extracted with ethyl acetate. The ethyl acetate layer was washed with saturated brine, dried ($MgSO_4$) and concentrated. The residue was subjected to silica gel column chromatography, and ethyl [2-[4-(5-methyl-2-phenyl 4-oxazolylmethoxy)phenylthio]-4-thiazolyl]acetate (400 mg, yield 78%) was obtained as colorless crystals from a fraction eluted with ethyl acetate-hexane (1:3, volume ratio), which was then recrystallized from ethyl acetate-hexane. melting point: 95–96° C.

EXAMPLE 71

A mixture of methyl (2-mercapto-4-methylthiazol-5-yl) acetate (455 mg), 4-(3-chloromethyl-5-ethoxyphenoxymethyl)-5-methyl-2-phenyloxazole (800 mg), potassium carbonate (465 mg) and N,N-dimethylformamide (20 ml) was stirred at room temperature for 2 hrs. The reaction mixture was poured into water, neutralized with 2N hydrochloric acid and extracted with ethyl acetate. The ethyl acetate layer was washed with water, dried ($MgSO_4$) and concentrated. The residue was subjected to silica gel column chromatography, and methyl [2-[3-ethoxy-5-(5-methyl-2-phenyl-4-oxazolylmethoxy)benzylthio]-4-methylthiazol-5-yl]acetate (1.02 g, yield 87%) was obtained as an oil from a fraction eluted with ethyl acetate-hexane (1:3, volume ratio).

NMR($CDCl_3$) δ: 1.39 (3H, t, J=7 Hz), 2.33 (3H, s), 2.44 (3H, s), 3.69 (2H, s), 3.72 (3H, s), 3.99 (2H, q, J=7 Hz), 4.30 (2H, s), 4.94 (2H, s), 6.45–6.65 (3H, m), 7.4–7.5(3H, m), 7.95–8.05 (2H, m).

EXAMPLE 72

A mixture of methyl [2-[3-ethoxy-5-(5-methyl-2-phenyl-4-oxazolylmethoxy)benzylthio]-4-methylthiazol-5-yl]acetate (1.01 g), 1N aqueous sodium hydroxide solution (10 ml), tetrahydrofuran (10 ml) and methanol (10 ml) was stirred at room temperature for 2 hrs. The reaction mixture was poured into water, neutralized with 2N hydrochloric acid and extracted with ethyl acetate. The ethyl acetate layer was washed with water, dried ($MgSO_4$) and concentrated. The precipitated crystals of [2-[3-ethoxy-5-(5-methyl-2-phenyl-4-oxazolylmethoxy)benzylthio]-4-methylthiazol-5-yl]acetic acid were collected by filtration. Recrystallization from ethyl acetate-hexane gave colorless prism crystals (910 mg, 93%). melting point: 115–116° C.

EXAMPLE 73

A mixture of methyl (3-hydroxy-1-phenyl-1H-pyrazol-4-yl)acetate (406 mg), 4-(4-chloromethyl-2-methoxyphenoxymethyl)-2-(2-furyl)-5-methyloxazole (551 mg), potassium carbonate (484 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried ($MgSO_4$) and concentrated. A mixture of the obtained colorless crystals, 1N aqueous sodium hydroxide solution (2 ml), tetrahydrofuran (4 ml) and methanol (4 ml) was stirred at room temperature for 1 hr. 1N Hydrochloric acid (2 ml) was added to the reaction mixture and the mixture was extracted with ethyl acetate. The ethyl acetate layer was washed with saturated brine, dried ($MgSO_4$) and concentrated. The obtained colorless crystals were collected by filtration to give [3-[4-[2-(2-furyl)-5-methyl-4-oxazolylmethoxy]-3-methoxybenzyloxy]-1-phenyl-1H-pyrazol-4-yl]acetic acid (748 mg, yield 88%). The crystals were recrystallized from ethyl acetate-hexane. melting point: 179–180° C.

EXAMPLE 74

A mixture of [3-[4-[2-(2-furyl)-5-methyl-4-oxazolylmethoxy]-3-methoxybenzyloxy]-1-phenyl-1H-pyrazol-4-yl]acetic acid (400 mg), 1-hydroxybenzotriazole hydrate (180 mg), WSC (230 mg), morpholine (100 mg) and N,N-dimethylformamide (10 ml) was stirred at room temperature for 15 hrs. The reaction mixture was poured into water and the mixture was extracted with ethyl acetate. The ethyl acetate layer was washed with saturated brine, dried ($MgSO_4$) and concentrated. The obtained colorless crystals were collected by filtration to give 4-[3-[4-[2-(2-furyl)-5-methyl1–4-oxazolylmethoxy]-3-methoxybenzyloxy]-1-phenyl-1H-pyrazol-4-yl]acetylmorpholine (440 mg, yield 96%), which was then recrystallized from ethyl acetate-hexane. melting point: 132–133° C.

EXAMPLE 75

A mixture of [3-[4-[2-(2-furyl)-5-methyl-4-oxazolylmethoxy]-3-methoxybenzyloxy]-1-phenyl-1H-pyrazol-4-yl]acetic acid (400 mg), 1-hydroxybenzotriazole hydrate (140 mg), WSC (180 mg), N-methylpiperazine (100 mg) and N,N-dimethylformamide (20 ml) was stirred at room temperature for 15 hrs. The reaction mixture was poured into water and the mixture was extracted with ethyl acetate. The ethyl acetate layer was washed with saturated brine, dried ($MgSO_4$) and concentrated. The obtained colorless crystals were collected by filtration to give 1-[3-[4-[2-(2-furyl)-5-methyl-4-oxazolylmethoxy]-3-methoxybenzyloxy]-1-phenyl-1H-pyrazol-4-yl]acetyl-4-methylpiperazine (320 mg, yield 68%), which was then recrystallized from ethyl acetate-hexane. melting point: 116–117° C.

EXAMPLE 76

A mixture of [3-[4-[2-(2-furyl)-5-methyl-4-oxazolylmethoxy]-3-methoxybenzyloxy]-1-phenyl-1H-pyrazol-4-yl]acetic acid (400 mg), 1-hydroxybenzotriazolehydrate (140 mg), WSC (180 mg), N-ethylpiperazine (110 mg) and N,N-dimethylformamide (20 ml) was stirred at room temperature for 15 hrs. The reaction mixture was poured into water and the mixture was extracted with ethyl acetate. The ethyl acetate layer was washed with saturated brine, dried (MgSO$_4$) and concentrated. The obtained colorless crystals were collected by filtration to give 4-ethyl-1-[3-[4-[2-(2-furyl)-5-methyl-4-oxazolylmethoxy]-3-methoxybenzyloxy]-1-phenyl-1H-pyrazol-4-yl]acetylpiperazine (350 mg, yield 73%). The crystals were recrystallized from ethyl acetate-hexane. melting point: 112–113° C.

EXAMPLE 77

A mixture of [3-[4-[2-(2-furyl)-5-methyl-4-oxazolylmethoxy]-3-methoxybenzyloxy]-1-phenyl-1H-pyrazol-5-yl]acetonitrile (500 mg), 2N aqueous sodium hydroxide solution (10 ml) and ethanol (10 ml) was refluxed for 4 hrs. 1N Hydrochloric acid (20 ml) was added to the reaction mixture and the mixture was extracted with ethyl acetate. The ethyl acetate layer was washed with saturated brine, dried (MgSO$_4$) and concentrated. The obtained colorless crystals were collected by filtration to give [3-[4-[2-(2-furyl)-5-methyl-4-oxazolylmethoxy]-3-methoxybenzyloxy]-1-phenyl-1H-pyrazol-5-yl]acetic acid (200 mg, yield 38%), which was then recrystallized from ethyl acetate-hexane. melting point: 145–146° C. (decomposition).

EXAMPLE 78

A mixture of ethyl 3-(3-hydroxy-1-phenyl-1H-pyrazol-5-yl)propionate (700 mg), 4-(4-chloromethyl-2-methoxyphenoxymethyl)-5-methyl-2-phenyloxazole (930 mg), potassium carbonate (750 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and ethyl 3-[3-[3-methoxy-4-(5-methyl-2-phenyl-4-oxazolylmethoxy)benzyloxy]-1-phenyl-1H-pyrazol-5-yl]propionate (1.35 g, yield 88%) was obtained as a colorless oil from a fraction eluted with ethyl acetate-hexane (1:1, volume ratio).

$^1$H-NMR(CDCl$_3$) δ:1.23 (3H, t, J=7.2 Hz), 2.41 (3H, s), 2.53–2.63 (2H, m), 2.89–2.99 (2H, m), 3.88 (3H, s), 4.11 (2H, q, J=7.2 Hz), 5.06 (2H, s), 5.17 (2H, s), 5.70 (1H, s), 6.90–7.08 (3H, m), 7.30–7.50 (8H, m), 7.96–8.05 (2H, m).

EXAMPLE 79

A mixture of ethyl 3-[3-[3-methoxy-4-(5-methyl-2-phenyl-4-oxazolylmethoxy)benzyloxy]-1-phenyl-1H-pyrazol-5-yl]propionate (1.33 g), 1N aqueous sodium hydroxide solution (5 ml), tetrahydrofuran (5 ml) and ethanol (5 ml) was stirred at room temperature for 1 hr. 1N Hydrochloric acid (5 ml) was added to the reaction mixture and the mixture was extracted with ethyl acetate. The ethyl acetate layer was washed with saturated brine, dried (MgSO$_4$) and concentrated. The obtained colorless crystals were collected by filtration to give 3-[3-[3-methoxy-4-(5-methyl-2-phenyl-4-oxazolylmethoxy)benzyloxy]-1-phenyl-1H-pyrazol-5-yl]propionic acid (1.17 g, yield 93%), which was then recrystallized from tetrahydrofuran-hexane. melting point: 157–158° C.

EXAMPLE 80

A mixture of ethyl 3-(3-hydroxy-1-phenyl-1H-pyrazol-5-yl)propionate (500 mg), 4-(4-chloromethylphenoxymethyl)-5-methyl-2-phenyloxazole (600 mg), potassium carbonate (530 mg) and N,N-dimethylformamide (10 ml) was stirred at 60° C. for 4 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and ethyl 3-[3-[4-(5-methyl-2-phenyl-4-oxazolylmethoxy)benzyloxy]-1-phenyl-1H-pyrazol-5-yl]propionate (980 mg, yield 95%) was obtained as a colorless oil from a fraction eluted with ethyl acetate-hexane (1:1, volume ratio).

$^1$H-NMR(CDCl$_3$) δ:1.23 (3H, t, J=7.0 Hz), 2.44 (3H, s), 2.52–2.64 (2H, m), 2.87–3.01 (2H, m), 4.12 (2H, q, J=7.0 Hz), 5.01 (2H, s), 5.18 (2H, s), 5.69 (1H, s), 6.96–7.08 (2H, m), 7.30–7.52 (10H, m), 7.98–8.06 (2H, m).

EXAMPLE 81

A mixture of ethyl 3-[3-[4-(5-methyl-2-phenyl-4-oxazolylmethoxy)benzyloxy]-1-phenyl-1H-pyrazol-5-yl]propionate (950 mg), 1N aqueous sodium hydroxide solution (4 ml), tetrahydrofuran (4 ml) and ethanol (4 ml) was stirred at room temperature for 1 hr. 1N Hydrochloric acid (4 ml) was added to the reaction mixture and the mixture was extracted with ethyl acetate. The ethyl acetate layer was washed with saturated brine, dried (MgSO$_4$) and concentrated. The obtained colorless crystals were collected by filtration to give 3-[3-[4-(5-methyl-2-phenyl-4-oxazolylmethoxy)benzyloxy]-1-phenyl-1H-pyrazol-5-yl]propionic acid (770 mg, yield 81%), which was then recrystallized from acetone-hexane. melting point: 154–155° C.

EXAMPLE 82

A mixture of ethyl 3-(3-hydroxy-1-phenyl-1H-pyrazol-5-yl)propionate (460 mg), 4-(3-chloromethylphenoxymethyl)-5-methyl-2-phenyloxazole (550 mg), potassium carbonate (350 mg) and N,N-dimethylformamide. (10 ml) was stirred at 60° C. for 4 hrs. The reaction mixture was poured into water and the mixture was extracted with ethyl acetate. The ethyl acetate layer was washed with saturated brine, dried (MgSO$_4$) and concentrated. The residue was subjected to silica gel column chromatography, and ethyl 3-[3-[3-(5-methyl-2-phenyl-4-oxazolylmethoxy)benzyloxy]-1-phenyl-1H-pyrazol-5-yl]propionate (850 mg, yield 90%) was obtained as a colorless oil from a fraction eluted with ethyl acetate-hexane (1:1, volume ratio).

$^1$H-NMR(CDCl$_3$) δ:1.23 (3H, t, J=7.2 Hz), 2.44 (3H, s), 2.54–2.62 (2H, m), 2.91–2.99 (2H, m), 4.12 (2H, q, J=7.2 Hz), 5.01 (2H, s), 5.23 (2H, s), 5.70 (1H, s), 6.95–7.01 (1H, m), 7.04–7.09 (1H, m), 7.12–7.18 (1H, m), 7.24–7.49 (9H, m), 7.98–8.06 (2H, m).

EXAMPLE 83

A mixture of ethyl 3-[3-[3-(5-methyl-2-phenyl-4-oxazolylmethoxy)benzyloxy]-1-phenyl-1H-pyrazol-5-yl]propionate (830 mg), 1N aqueous sodium hydroxide solution (3 ml), tetrahydrofuran (5 ml) and ethanol (5 ml) was stirred at room temperature for 2 hrs. 1N Hydrochloric acid (3 ml) was added to the reaction mixture and the mixture was extracted with ethyl acetate. The ethyl acetate layer was washed with saturated brine, dried (MgSO$_4$) and concentrated. The obtained colorless crystals were collected by filtration to give 3-[3-[3-(5-methyl-2-phenyl-4-oxazolylmethoxy)benzyloxy]-1-phenyl-1H-pyrazol-5-yl]propionic acid (490 mg, yield 62%), which was then recrystallized from acetone-isopropyl ether. melting point: 137–138° C.

| (1) Compound of Example 1 | 30 mg |
|---|---|
| (2) Microcrystalline cellulose | 10 mg |
| (3) Lactose | 19 mg |
| (4) Magnesium stearate | 1 mg |
| total | 60 mg |

Formulation Example 1

(Production of Capsules)

(1), (2) and (3) and (4) are admixed and filled in a gelatin capsule.

| (1) Compound of Example 1 | 30 g |
|---|---|
| (2) Lactose | 50 g |
| (3) Corn starch | 15 g |
| (4) Carboxymethylcellulose calcium | 44 g |
| (5) Magnesium stearate | 1 g |
| 1000 tablets total | 140 g |

Formulation Example 2

(Production of Tablets)

The entire amount of 1), 2) and 3) and 30 g of 4) are admixed with water. After drying in vacuo, the mixture is granulated. Thereto are added 14 g of (4) and 1 g of (5) and the mixture is tableted with a tableting machine. In this way, 1,000 tablets containing 30 mg of the compound of Example 1 per tablet are obtained.

INDUSTRIAL APPLICABILITY

The compound of the present invention has low toxicity and can be used as, for example, a prophylactic or therapeutic agent of diabetes mellitus (e.g., type 1 diabetes mellitus, type 2 diabetes mellitus, gestational diabetes mellitus etc.); a prophylactic or therapeutic agent of hyperlipidemia (e.g., hypertriglyceridemia, hypercholesterolemia, hypo-high-density-lipoproteinemia, postprandial hyperlipidemia etc.); an insulin sensitizer; an agent for improving insulin resistance; a prophylactic or therapeutic agent of impaired glucose tolerance (IGT), and an agent for preventing progress from impaired glucose tolerance to diabetes mellitus.

The compound of the present invention can be also used as a prophylactic or therapeutic agent of diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, dermal soft tissue infection, lower limb infection etc.), diabetic gangrene, xerostomia, decreased sense of hearing, cerebrovascular disease, peripheral circulatory disturbance etc.), obesity, osteoporosis, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disorder etc.), muscular dystrophy, myocardiac infarction, angina pectoris, cerebrovascular diseases (e.g., cerebral infarction, cerebral apoplexy), insulin resistant syndrome, syndrome X, hyperinsulinemia, hyperinsulinemia-induced sensory disorder, tumors (e.g., leukemia, breast cancer, prostate cancer, skin cancer etc.), irritable bowel syndrome, acute or chronic diarrhea, inflammatory diseases (e.g., chronic rheumatoid arthritis, spondylitis deformans, osteoarthritis, lumbago, gout, post-operative or traumatic inflammation, remission of swelling, neuralgia, pharyngolaryngitis, cystitis, hepatitis (including non-alcoholic steatohepatitis), pneumonia, pancreatitis, inflammatory colitis, ulcerative colitis etc.), visceral obesity syndrome, arteriosclerosis (e.g., atherosclerosis) and the like.

Also, the compound of the present invention can be used for ameliorating bellyache, nausea, vomiting, or dysphoria in epigastrium, each of which is accompanied by gastrointestinal ulcer, acute or chronic gastritis, biliary dyskinesia or cholecystitis.

Further, the compound of the present invention can control (enhance or inhibit) appetite, and therefore, can be used as a therapeutic agent of leanness and cibophobia (the weight increase in administration subjects suffering from leanness or cibophobia) or a therapeutic agent of obesity.

This application is based on a patent application No. 85572/2001 filed in Japan, the contents of which are hereby all incorporated by reference. The references cited in this specification, including patents and patent applications, are hereby incorporated in their entireties by reference, to the extent that they have been disclosed herein.

The invention claimed is:

1. A compound represented by the formula:

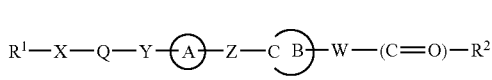

(I)

wherein

R$^1$ is an optionally substituted oxazolyl group;

X is a bond, an oxygen atom, a sulfur atom, —CO—, —CS—, —CR$^3$(OR$^4$)— or —NR$^5$— (R$^3$ is a hydrogen atom or an optionally substituted hydrocarbon group, R$^4$ is a hydrogen atom or a hydroxy-protecting group and R$^5$ is a hydrogen atom, an optionally substituted hydrocarbon group or an amino-protecting group);

Q is a divalent hydrocarbon group having 1 to 20 carbon atoms;

Y is a bond, an oxygen atom, a sulfur atom, —SO—, —SO$_2$—, —NR$^6$—, —CONR$^6$— or —NR$^6$CO— (R$^6$ is a hydrogen atom or an optionally substituted hydrocarbon group);

ring A
is an aromatic ring optionally further having 1 to 3 substituents;

Z is —(CH$_2$)$_n$—Z$^1$— or —Z$^1$—(CH$_2$)$_n$— (n is an integer of 0 to 8, Z$^1$ is a bond, an oxygen atom, a sulfur atom, —SO—, —SO$_2$—, —NR$^7$—, —CONR$^7$— or —NR$^7$CO— (R$^7$ is a hydrogen atom or an optionally substituted hydrocarbon group));

ring B
is a pyrazole ring optionally further having 1 to 3 substituents;

W is a divalent saturated hydrocarbon group having 1 to 20 carbon atoms; and

R$^2$ is —OR$^8$ (R$^8$ is a hydrogen atom or an optionally substituted hydrocarbon group) provided that ring B does not have, on the ring-constituting N atom, a substituent represented by the formula:

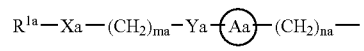

wherein

R$^{1a}$ is an optionally substituted hydrocarbon group or an optionally substituted heterocyclic group;

Xa is a bond, an oxygen atom, a sulfur atom, —CO—, —CS—, —CR$^{2a}$(OR$^{3a}$)— or —NR$^{4a}$— (R$^{2a}$ and R$^{4a}$ are each a hydrogen atom or an optionally substituted hydrocarbon group and R$^{3a}$ is a hydrogen atom or a hydroxy-protecting group);

ma is an integer of 0 to 3;

Ya is an oxygen atom, a sulfur atom, —SO—, —SO$_2$—, —NR$^{5a}$—, —CONR$^{5a}$— or —NR$^{5a}$CO— (R$^{5a}$ is a hydrogen atom or an optionally substituted hydrocarbon group);

ring Aa
is an aromatic ring optionally further having 1 to 3 substituents; and na is an integer of 1 to 8, or a salt thereof, or a prodrug thereof.

2. The compound of claim 1, wherein X is a bond or —NR$^5$— (R$^5$ is a hydrogen atom, an optionally substituted hydrocarbon group or an amino-protecting group).

3. The compound of claim 1, wherein Q is C$_{1-6}$ alkylene or C$_{2-6}$ alkenylene.

4. The compound of claim 1, wherein Y is an oxygen atom or —NR$^6$— (R$^6$ is a hydrogen atom or an optionally substituted hydrocarbon group).

5. The compound of claim 1, wherein n is an integer of 0 to 3, Z$^1$ is a bond, an oxygen atom, a sulfur atom, —NR$^7$—, —CONR⁷— or —NR⁷CO— (R⁷ is a hydrogen atom or an optionally substituted hydrocarbon group).

6. The compound of claim 1, wherein W is a divalent saturated hydrocarbon group having 1 to 6 carbon atoms.

7. The compound of claim 1, wherein the substituent that the ring B optionally further has is a hydrocarbon group.

8. The compound of claim 1, which is [1-methyl-3-[4-(5-methyl-2-phenyl-4-oxazolylmethoxy)benzyloxy]-1H-pyrazol-4-yl]acetic acid,

[3-[4-(5-methyl-2-phenyl-4-oxazolylmethoxy)benzyloxy]-1-phenyl-1H-pyrazol-4-yl]acetic acid, 3-[3-[3-methoxy-4-(5-methyl-2-phenyl-4-oxazolylmethoxy)benzyloxy]-1-phenyl-1H-pyrazol-5-yl]propionic acid, 3-[3-[4-(5-methyl-2-phenyl-4-oxazolylmethoxy)benzyloxy]-1-phenyl-1H-pyrazol-5-yl]propionic acid, or 3-[3-[3-(5-methyl-2-phenyl-4-oxazolylmethoxy)benzyloxy]-1-phenyl-1H-pyrazol-5-yl]propionic acid.

9. A pharmaceutical composition comprising the compound of claim 1 or a salt thereof or a prodrug thereof and a phamaceutically acceptable carrier, excipient or diluent.

10. The pharmaceutical composition of claim 9, which is a therapeutic agent of diabetes mellitus.

11. The pharmaceutical composition of claim 9, which is a therapeutic agent of hyperlipidemia.

12. The pharmaceutical composition of claim 9, which is a therapeutic agent of impaired glucose tolerance.

* * * * *